US012622946B2

(12) United States Patent
Do et al.

(10) Patent No.: US 12,622,946 B2
(45) Date of Patent: May 12, 2026

(54) HLA-DR/CII PEPTIDE COMPLEXES FOR TREATING ARTHRITIS

(71) Applicant: FRAUNHOFER-GESELLSCHAFT ZUR FÖRDERUNG DER ANGEWANDTEN FORSCHUNG E.V., Munich (DE)

(72) Inventors: Nhu-Nguyen Do, Langen (DE); Vilma Urbonaviciute, Spånga (SE); Sylvia Cienciala, Nidderau (DE); Rikard Holmdahl, Stockholm (SE); Harald Burkhardt, Frankfurt am Main (DE)

( * ) Notice: Subject to any disclaimer, the term of this patent is extended or adjusted under 35 U.S.C. 154(b) by 1033 days.

(21) Appl. No.: 17/633,894

(22) PCT Filed: Aug. 7, 2020

(86) PCT No.: PCT/EP2020/072280
§ 371 (c)(1),
(2) Date: Feb. 8, 2022

(87) PCT Pub. No.: WO2021/028347
PCT Pub. Date: Feb. 18, 2021

(65) Prior Publication Data
US 2022/0280599 A1 Sep. 8, 2022

(30) Foreign Application Priority Data
Aug. 9, 2019 (EP) ..................................... 19191077

(51) Int. Cl.
| | |
|---|---|
| *A61K 38/17* | (2006.01) |
| *A61K 39/00* | (2006.01) |
| *A61P 19/02* | (2006.01) |
| *A61P 29/00* | (2006.01) |
| *A61P 37/00* | (2006.01) |
| *C07K 14/74* | (2006.01) |
| *C07K 14/78* | (2006.01) |

(52) U.S. Cl.
CPC .......... *A61K 38/17* (2013.01); *A61K 38/1774* (2013.01); *A61K 39/0008* (2013.01); *A61P 19/02* (2018.01); *A61P 29/00* (2018.01); *A61P 37/00* (2018.01); *C07K 14/70539* (2013.01); *C07K 14/78* (2013.01)

(58) Field of Classification Search
CPC .............. C07K 14/70539; C07K 14/78; A61K 38/1774; A61K 38/17
See application file for complete search history.

(56) References Cited

U.S. PATENT DOCUMENTS

| | | |
|---|---|---|
| 6,106,840 A | 8/2000 | Clark |
| 6,451,314 B1 | 9/2002 | Clark |
| 6,632,604 B2 | 10/2003 | Mach |
| 2007/0161545 A1 | 7/2007 | Holmdahl |

| | | | | |
|---|---|---|---|---|
| 2009/0227516 A1* | 9/2009 | Holmdahl | ............... | A61P 19/02 |
| | | | | 530/328 |
| 2010/0015644 A1 | 1/2010 | Gerarda Havenith | | |
| 2010/0168390 A1 | 7/2010 | Brix et al. | | |
| 2010/0226854 A1 | 9/2010 | Scholler | | |
| 2013/0309229 A1 | 11/2013 | Yang et al. | | |

FOREIGN PATENT DOCUMENTS

| | | |
|---|---|---|
| EP | 1332760 A1 | 8/2003 |
| JP | 08151396 A | 6/1996 |
| WO | 1996040944 A2 | 12/1996 |
| WO | 1998005684 A2 | 2/1998 |
| WO | 2001036448 A2 | 5/2001 |
| WO | 2003/050542 A2 | 6/2003 |
| WO | 2007/017556 A1 | 2/2007 |
| WO | 2007/058587 A1 | 5/2007 |
| WO | 2007/123976 A2 | 11/2007 |
| WO | 2008/090360 A1 | 7/2008 |
| WO | 2012/138294 A1 | 10/2012 |

OTHER PUBLICATIONS

Jones et al., Nat. Rev. Immunol., 2006, vol. 6:271-282.*
Butterfield et al., Biochemistry, 2010, vol. 49(7):1549-1555.*
Moro et al., BMC Immunol., 2005, vol. 6, Article #24.*
Benson et al. "Arthritis in space and time—To boldly go!" FEBS Letters, 2011, vol. 585, No. 23, pp. 3640-3648.
Sakurai et al. "Analog peptides of type II collagen can suppress arthritis in HLA-DR4 (DRB1*0401) transgenic mice," Arthritis Research & Therapy, Sep. 2006, vol. 8, No. 5, R150, 7 pages.
International Search Report and Written Opinion for International (PCT) Patent Application No. PCT/EP2020/072280, dated Oct. 12, 2020, 12 pages.
Du Souich et al., "Immunomodulatory and anti-inflammatory effects of chondroitin sulphate," J. Cell. Mol. Med. vol. 13, No. 8A, 2009 pp. 1451-1463, doi:10.1111/j.1582-4934.2009.00826.x.
Malmstrom et al., "T cells that are naturally tolerant to cartilage-derived type II collagen are involved in the : levelopment of collagen-induced arthritis." Arthritis Research. 2000. 2, 315-326.
Michaelsson et al., "Antigen processing and presentation of a naturally glycosylated protein elicits major histocompatibility complex class II-restricted, carbohydrate-specific T cells." European Journal of Immunology_ 1996. 26(8):1906-1910.

(Continued)

*Primary Examiner* — Xiaozhen Xie
(74) *Attorney, Agent, or Firm* — SAFFIRE IP; Daren P Nicholson

(57) ABSTRACT

The present invention relates to HLA-DR/CII peptide complexes comprising a chondroitin-binding peptide at the C-terminal end of the polypeptide comprising the HLA-DR/CII alpha chain and/or the HLA-DR/CII beta chain, wherein the CII peptide is fused to the N-terminus of the HLA-DR/CII alpha chain or the HLA-DR/CII beta chain by a linker peptide, for use in treating chronic inflammatory disease, such as arthritis, in human patients. The lysines in the CII peptide, particularly the first lysine in the CII peptide, may be post-translationally modified. The invention further relates to methods of producing said HLA-DR/CII peptide complexes in mammalian cells.

17 Claims, 19 Drawing Sheets

Specification includes a Sequence Listing.

(56)                    References Cited

OTHER PUBLICATIONS

Michaelsson et al., "Identification of an immunodominant type-II collagen peptide recognized by T cells in H-2q mice: , self tolerance at the level of determinant selection." European Journal of Immunology_ 1992. 22(7): 1819-1825.

Michaelsson et al., "T cell recognition of carbohydrates on type II collagen." Journal of Experimental Medicine. 1994. 180(2), 745-749.

Myers et al., "Characterization of a tolerogenic T cell epitope of type II collagen and its relevance to collagen-induced arthritis." Journal of Immunology_ 1992. 149: 1439-1443.

Zuo et al., "A single-chain class II MHC-IgG3 fusion protein inhibits autoimmune arthritis by induction of antigen-specific hyporesponsiveness." Journal of Immunology_2002. 168(5):2554-2559.

Broddefalk et al., "Preparation of a diglycosylated hydroxylysine building block used in solid-phase synthesis of a Glycopeptidefrom type II collagen." Journal of Organic Chemistry. 1999. 64, 8948-8953.

Myers, "Peptide-Induced Suppression of Collagen-Induced Arthritis in HLA-DR1 Transgenic Mice," American College of Rheumatology, vol. 46, No. 12, Dec. 2002, pp. 3369-3377.

Gregersen PK et al., "The Shared Epitope Hypothesis: An approach to understanding the molecular genetics of susceptibility to rheumatoid arthritis," Arthritis Rheum. 1987;30:1205-1213.

Burkhardt H et al., "Humoral immune response to citrullinated collagen type II determinants in early rheumatoid arthritis," Eur J Immunol. 2005; 35:1643-52.

Backlund et al. "Predominant selection of T cells specific for the glycosylated collagen type II epitope (263-270) in 5 humanized transgenic mice and in rheumatoid arthritis." Proceedings of the National Academy of Sciences of the USA.2002. 99(15) 9960-9965.

Holmdahl R. et al., "The molecular pathogenesis of collagen-induced arthritis in mice—a model for rheumatoid arthritis," Ageing Res Rev. 2002;1: 135-47.

Chin R. K., et al., "Lymphotoxin Pathway-Directed, Autoimmune Regulator-Independent Central Tolerance to Arthritogenic Collagen," J Immunol. 2006; 177: 290-7.

Aho, K., Palosuo, T., Raunio, V., Puska, P., Aromaa, A. & Salonen, J.T., "When does rheumatoid arthritis , start?" (1985) Arthritis Rheum 28, 485-489.

Rantapaa-Dahlqvist, S., de Jong, B. A., Berglin, E., Hallmans, G., Wadell, G., Stenlund, H., Sundin, U. & van Venrooij, W. J., "Antibodies against cyclic citrullinated peptide and IgA rheumatoid factor predict the development of rheumatoid arthritis" (2003) Arthritis Rheum 48, 2741-9.

Berglin, E., Padyukov, L., Sundin, U., Hallmans, G., Stenlund, H., Van Venrooij, W. J., Klareskog, L. & Dahlqvist, S. R., A combination of autoantibodies to cyclic citrullinated peptide (CCP) and HLA-DRB1 locus antigens is strongly associated with future onset of rheumatoid arthritis (2004) Arthritis Res Ther 6, R303-8.

Van Gaalen, F. A., van Aken, J., Huizinga, T. W., Schreuder, G. M., Breedveld, F. C., Zanelli, E., van Ven-rooij, W. J., Verweij, C. L., Toes, R. E. & de Vries, R. R., "Association between HLA class II genes and autoantibodies to cyclic citrullinated peptides (CCPs) influences the severity of rheumatoid arthritis," (2004) Arthritis Rheum 50, 2113-21.

Corrigall, V. M. et al., "The Human Endoplasmic Reticulum Molecular Chaperone BiP Is an Autoantigen for Rheumatoid Arthritis and Prevents the Induction of Experimental Arthritis," (2001) J Immunol 166, 1492-8.

Fritsch, R. et al., "Characterization of Autoreactive T Cells to the Autoantigens Heterogeneous Nuclear Ribonucleoprotein A2 (RA33) and Filaggrin in Patients with Rheumatoid Arthritis" (2002) J Immunol 169, 1068-76.

Cook, A. D., Rowley, M. J., Mackay, I. R., Gough, A. & Emery, P., "Antibodies to Type II Collagen in Early Rheumatoid Arthritis" (1996) Arthritis Rheum 39, 1720-1727.

Holm, B., Baquer, S. M., Holm, L, Holmdahl, R. & Kihlberg, J., "Role of the Galactosyl Moiety of Collagen Glycopeptides for T-Cell Stimulation in a Model for Rheumatoid Arthritis," (2003) Bioorganic and Medicinal Chemistry 11, 3981-7.

Scott, C. A., Garcia, K. C, Carbone, F. R., Wilson, I. A. & Teyton, L., "Role of Chain Pairing for the Production of Functional Soluble IA Major Histocompatibility Complex Class II Molecules" (1996) J Exp Med 183, 2087-95.

Bunch, T. A., Grinblat, Y. & Goldstein, L. S., "Characterization and use of the Drosophila metallothionein promoter in cultured Drosophila melanogaster cells" (1988) Nucleic Acids Res 16, 1043-61.

Andersson, M. & Holmdahl, R., "Analysis of type II collagen-reactive T cells in the mouse. I. Different regulation of autoreactive vs. non-autoreactive anti-type II collagen T cells in the DBA/1 mouse" (1990) Eur J Immunol 20, 1061-1066.

Broddefalk, J., Backlund, J., Almqvist, F., Johansson, M., Holmdahl, R. & Kihlberg, J., "T Cells Recognize a Glycopeptide Derived from Type II Collagen in a Model for Rheumatoid Arthritis" (1998) J Am Chem Soc 120, 7676-7683.

Holmdahl, R., Klareskog, L., Andersson, M. & Hansen, C., "High antibody response to autologous type II collagen is restricted to H-2q" (1986) Immunogenetics 24, 84-89 (Abstract only).

Raposo, Merky, et al., "T cells specific for post-translational modifications escape intrathymic tolerance induction," 2018, Nature Communications 9 (1): 353.

Ponchel et al., "CD4+ T-cell subsets in rheumatoid arthritis," Int. J. Clin. Rheumatol. (2012) 7(1), 37-53.

Van Eden et al., "Cloning of the mycobacterial epitope recognized by T lymphocytes in adjuvant arthritis," Nature 331; 171-172 Jan. 14, 1988.

Van Eden et al., "Arthritis induced by a T-lymphocyte clone that responds to Mycobacterium tuberculosis and to cartilage proteoglycan," PNAS 1985; 5117-5120, Abstract.

Vanderlugdt et al., "Epitope spreading in immune-mediated diseases: implications for immunotherapy," Nature Reviews Immunology 2, 85-95 (2002) Abstract.

Vanderlugdt et al., "Epitope Spreading," Current Opinion in Immunology, vol. 8, Issue 6, Dec. 1996, pp. 831-836, Abstract.

Bajtner et al., "Chronic development of collagen-induced arthritis is associated with arthritogenic antibodies against specific epitopes on type II collagen," Arthritis Research & Therapy vol. 7 No. 5 2005.

Bevaart et al., "Evaluation of Therapeutic Targets in Animal Models of Arthritis," Arthritis & Rheumatism. 62, 2192-2205 (2010).

Freysdottir, "Mucosal tolerance to KLH reduces BSA-induced arthritis in rats—an indication of bystander suppression," J Clin Immunol. May 2007;27(3):284-93 Abstract.

Kalandadze et al., "Expression of Recombinant HLA-DR2 Molecules," (J. Biol. Chem. 1996, 271 (33), 20156-20162) (Year: 1996).

Cresswell, P, "Assembly, Transport, and Function of MHC Class II Molecules," (Annual Rev. Immunol. 1994, 12: 259-293) (Year: 1994).

Latham et al. "Ex Vivo Characterization of the Autoimmune T Cell Response in the HLA-DRI Mouse Model of Collagen-Induced Arthritis Reveals Long-Term Activation of Type II Collagen-Specific Cells and Their Presence in Arthritic Joints," (J. Immunol. Jan. 4, 2005, 174: 3978-3985) (Year: 2005).

Batsalova et al., "Mice Producing Less Reactive Oxygen Species Are Relatively Resistant to Collagen Glycopeptide Vaccinationagainst Arthritis" J_ Immunol. (2010) 185;2701-2709.

Cecconi, V., et al., "Use of MHC Tetramers to Investigate CD4+ T Cell Responses: Problems and Solutions," Cytometry Part A, 2008; 73A:1010-1018.

Cumberbatch et al., "Chicken major histocompatibility complex class II molecules of the B19 haplotype present self and foreign peptides," Animal Genetics, No. 37, pp. 393-396, 2006.

Krco et al., "Characterization of the Antigenic Structure of Human Type II Collagen," The Journal of Immunology, No. 156, pp. 2761-2768, 1996.

Holmdahl, R. et al., "Genetic Analysis of Mouse Model" (1998) in Human Genome Methods, ed. Adolpho, K. W. (CRC press, New York), pp. 215-238.

(56)                    References Cited

OTHER PUBLICATIONS

Von Delwig et al. "The Impact of Glycosylation on HLA-DRI-Restricted T Cell Recognition of Type II Collagen in a Mouse Model," (Arthritis & Rheumatism, Feb. 1, 2006, 54(2): 482-491) (Year: 2006).

Rammensee et al., ("MHC Ligands and Peptide Motifs," 1997, Landes Bioscience, Austin, Texas, pp. 300-301) (Year: 1997).

Nelson et al. "Identification of two distinct properties of class II major histocompatibility complex associated peptides," (PNAS, 1993, 90: 1227-1231) (Year 1993).

Holm, el. al., "An Improved Synthesis of a Galactosylaled Hydroxylysine Building Block and its use in Solid-Phase Glycopeptide Synthesis," Tetrahedron, 2000, vol. 56, pp. 1579-1586.

Backlund et al. "Glycosylation of type II collagen is of major importance for T cell tolerance and pathology in collagen-nduced arthritis." European Journal of Immunology_2002. 32(12):3776-84.

Broddefalk et al. "Use of acid-labile protective groups for carbohydrate moieties in synthesis of glycopeptides related to type II collagen." Tetrahedron. 1998. 54, 12047-12070.

Corthay et al. "Epitope glycosylation plays a critical role for T cell recognition of type II collagen in collagen-induced Arthritis." European Journal of Immunology_ 1998. 28(8), 2580-2590.

Dzhambazov et al., "The major T cell epitope on type II collagen is glycosylated in normal cartilage but modified by arthritis in both rats and humans." European Journal of Immunology_2005. 35(2), 357-366.

Holm et al., "Glycopeptide specificity of helper T cells obtained in mouse models for rheumatoid arthritis." Chembiochem. 2002 3(12), 1209-1222.

Kjellen et al., "The structural basis of MHC control of collagen-induced arthritis; binding of the immunodominant type II collagen 256-270 glycopeptide to H-2Aq and H-2Ap molecules." European Journal of Immunology_ 1998. 28(2):755-767.

Arnau et al., "Current strategies for the use of affinity tags and tag removal for the purification of recombinant proteins," Protein Expression and Purification, 2006(48): 1-13.

Barozzi et al., "Affibody-Binding Ligands," International Journal of Molecular Sciences, 2020, 21, 3769.

* cited by examiner

HEK cells
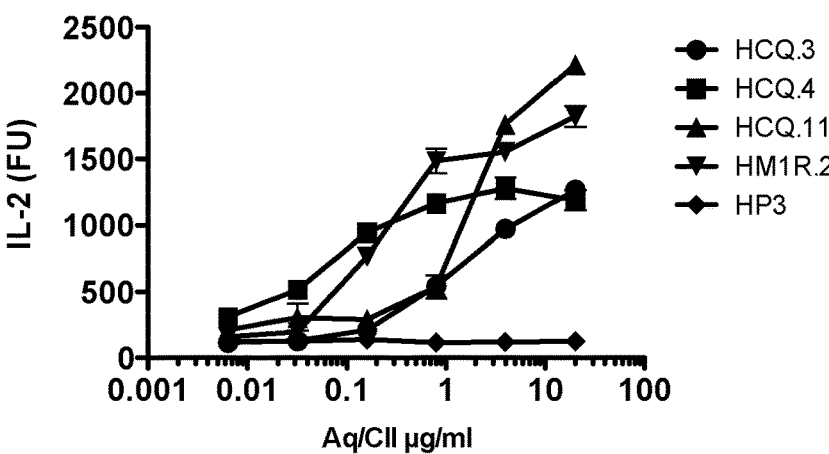
Insect S2 cells
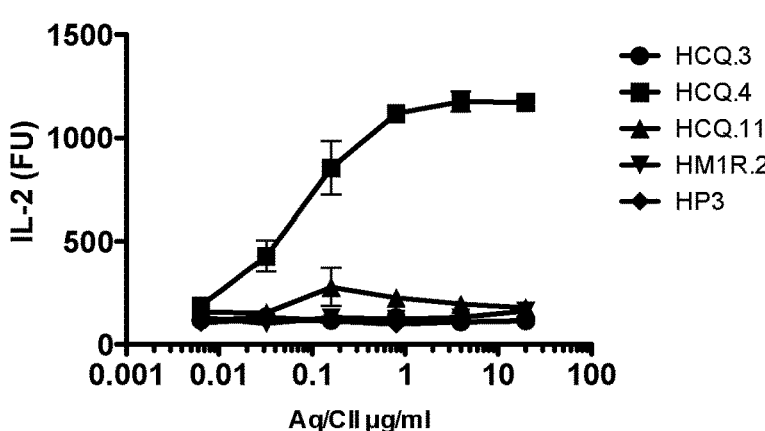
anti-CD3
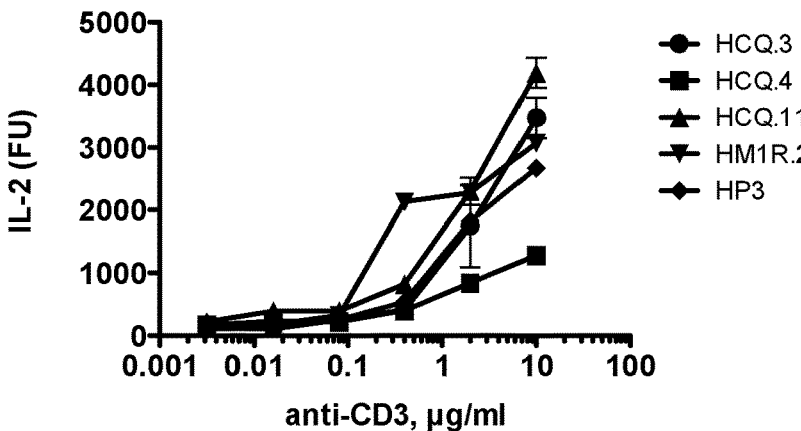
Figure 2

A)
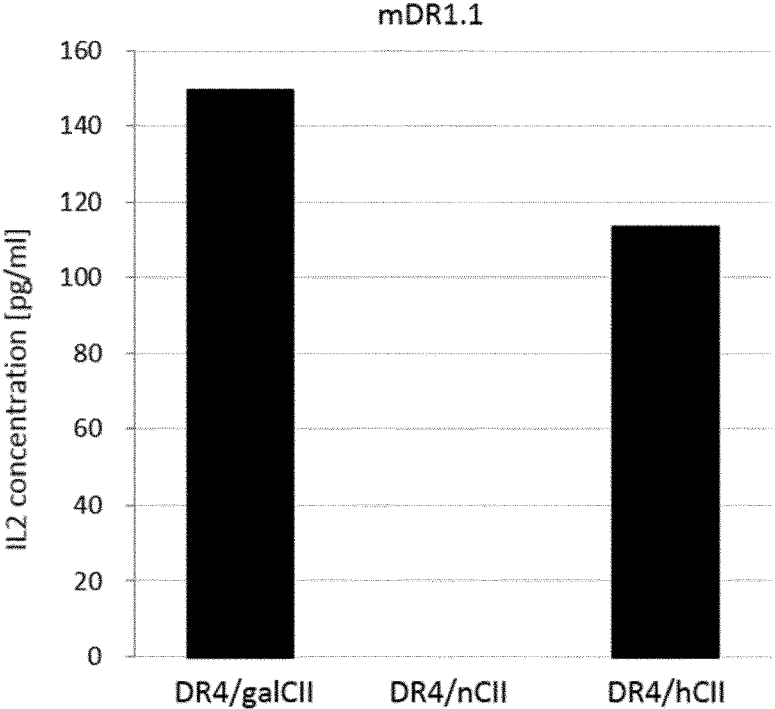
B)
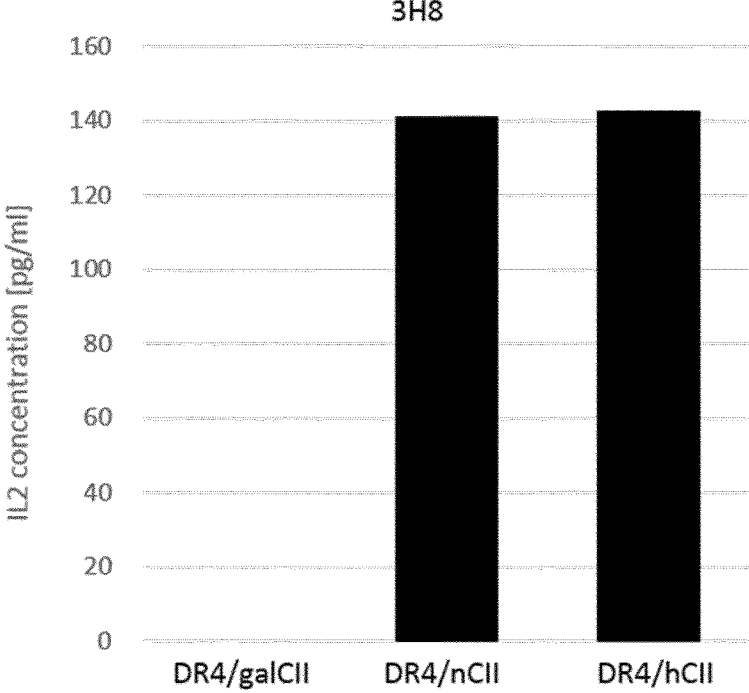
Figure 4

(A)
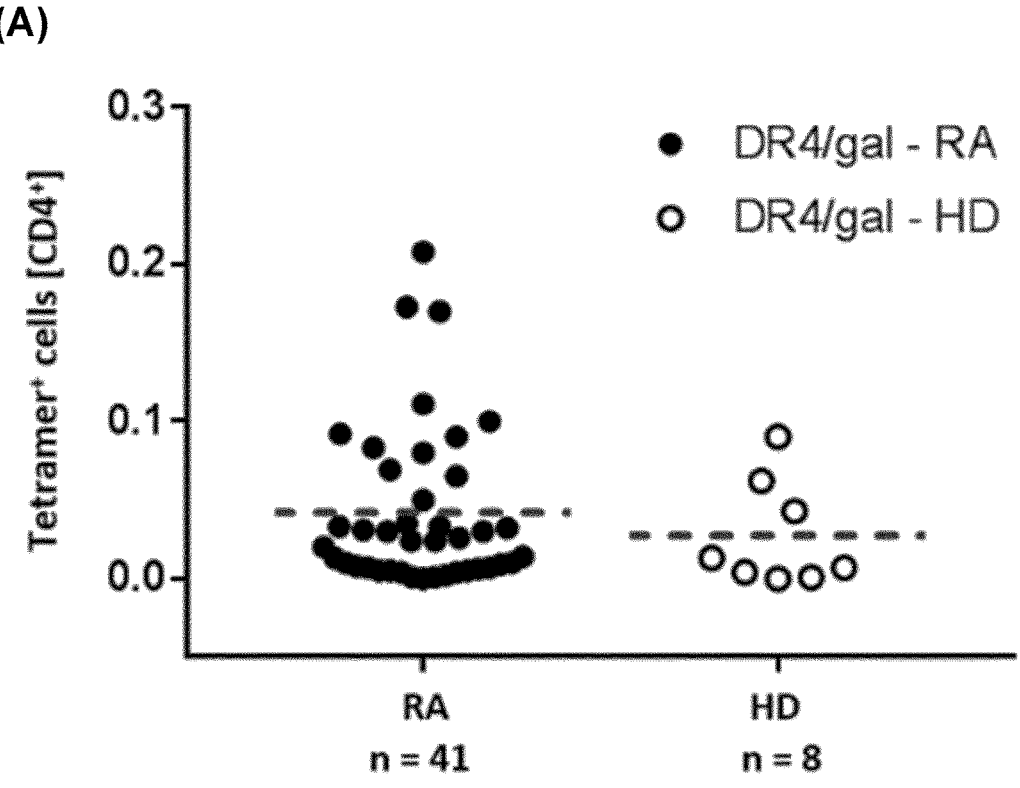
(B)
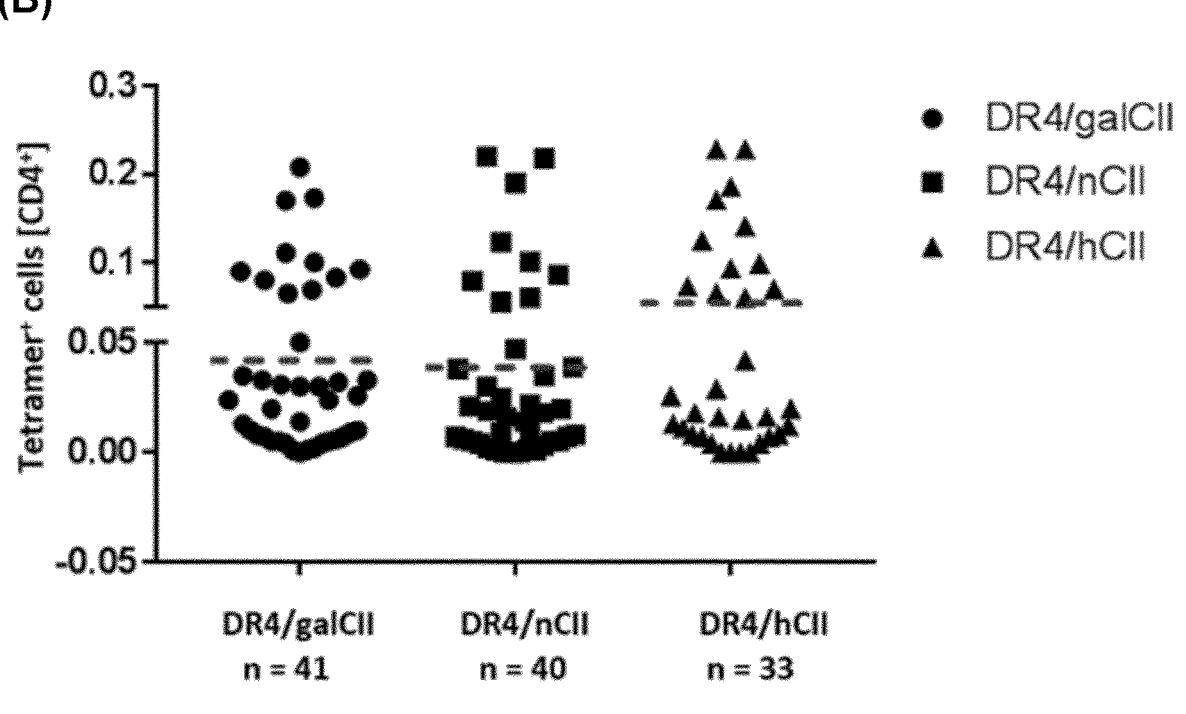
Figure 5

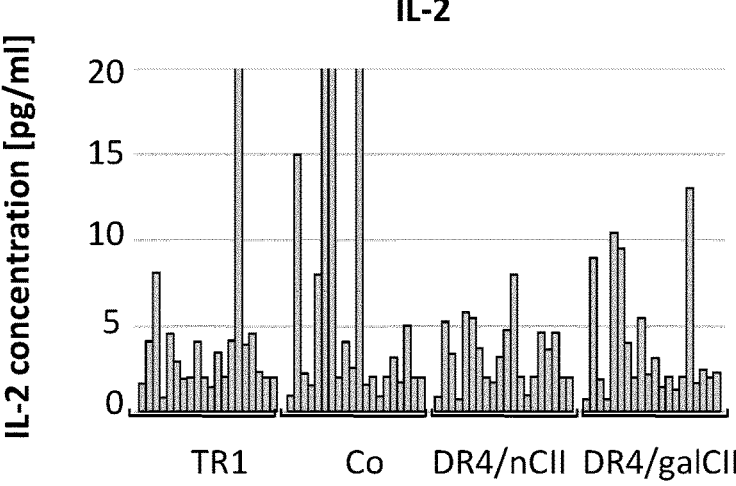
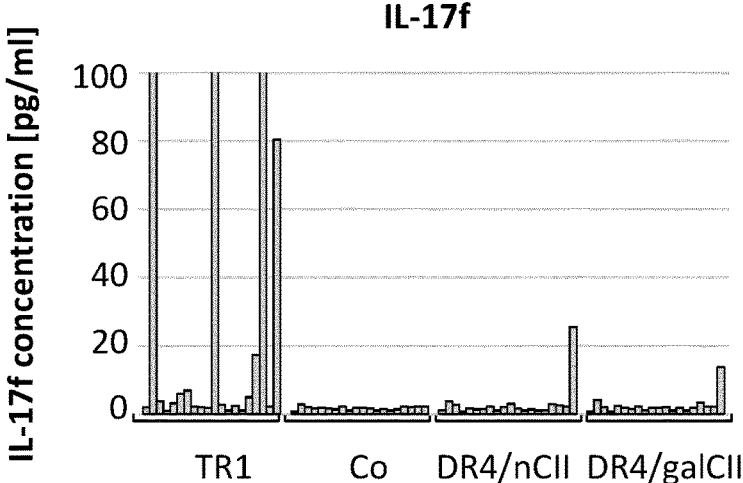
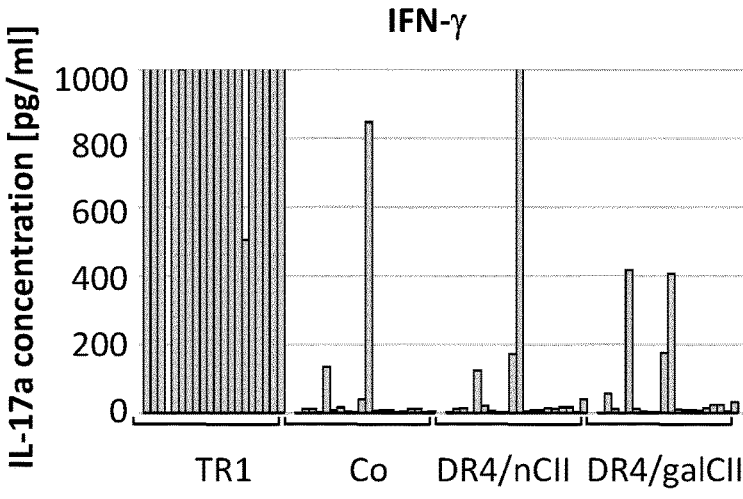
Figure 7

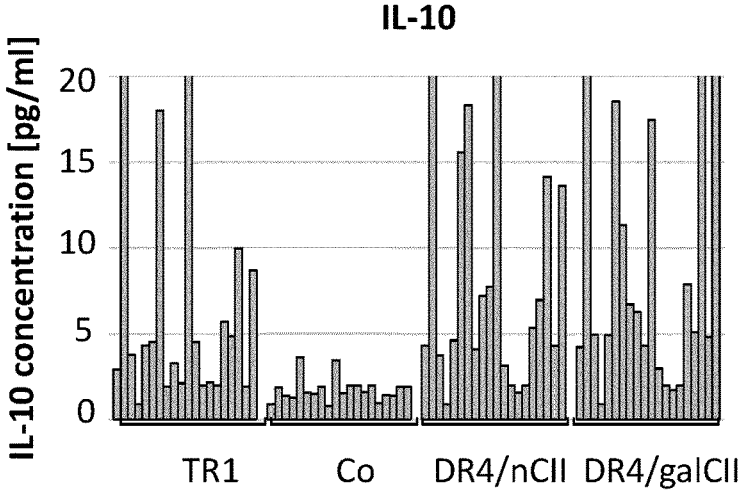
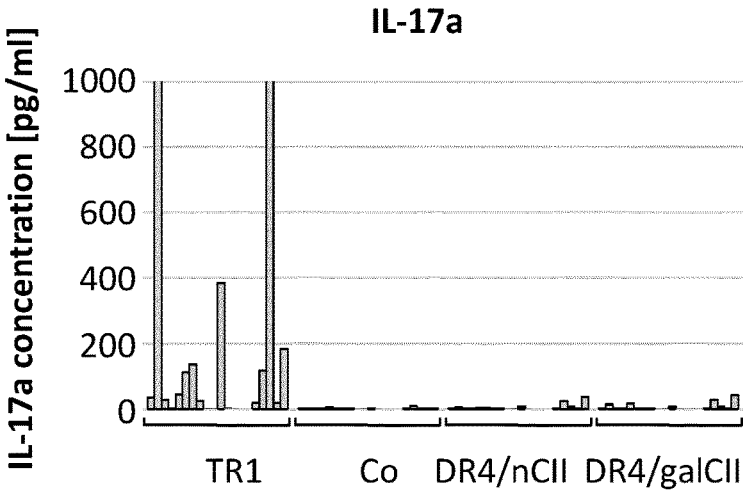
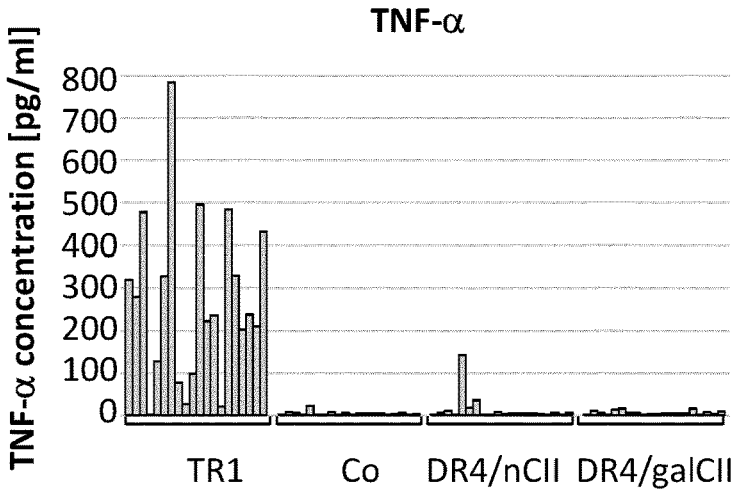
Figure 7 (cont.)

(A)
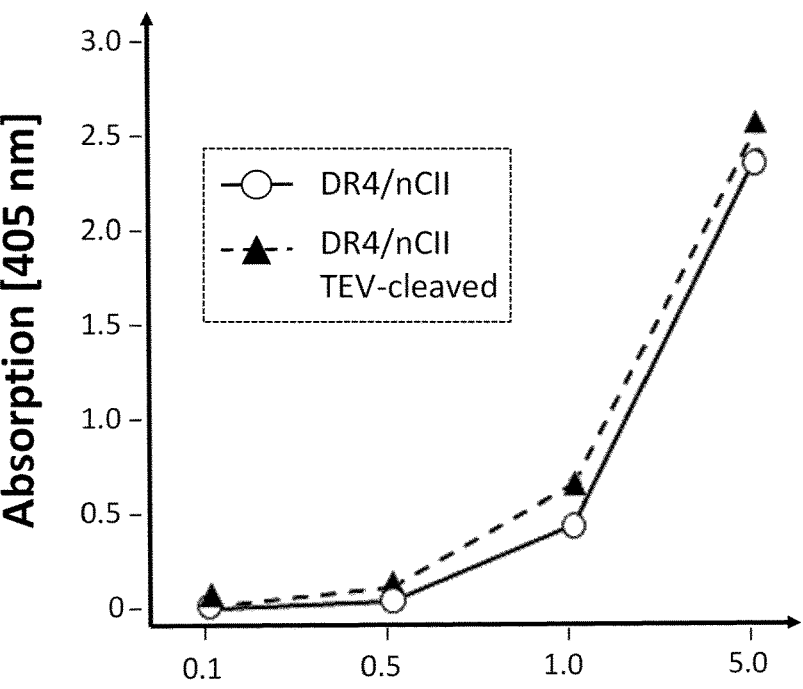
(B)
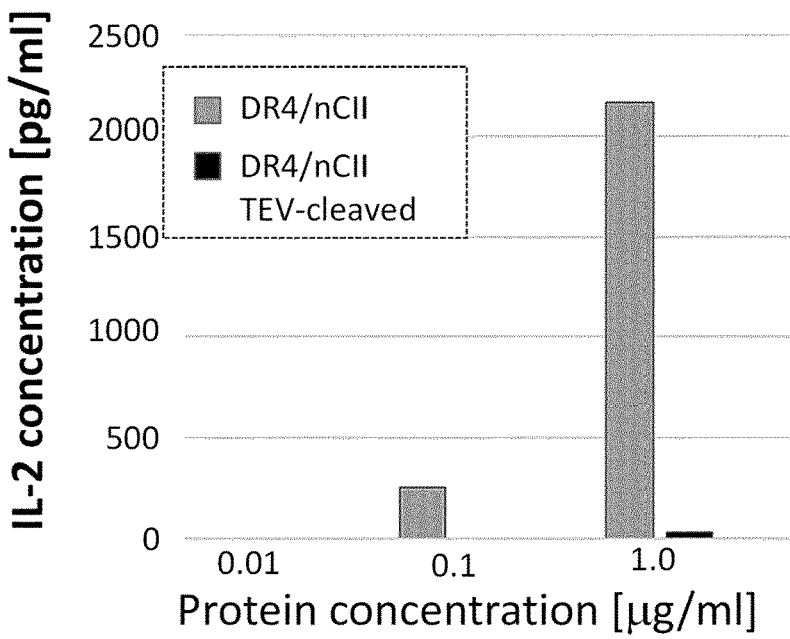
Figure 8

(A)
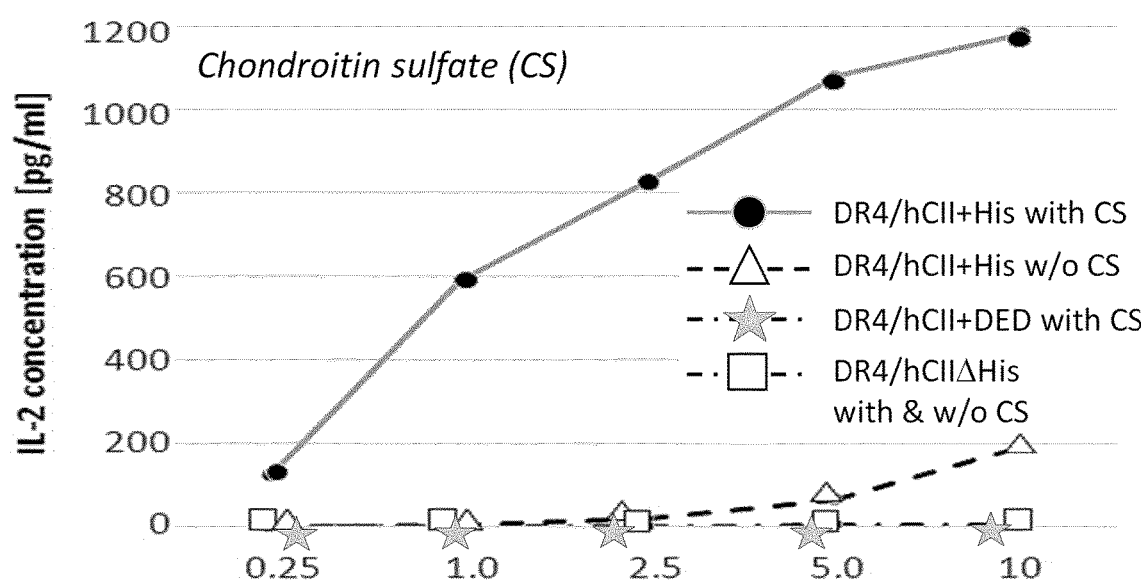
(B)
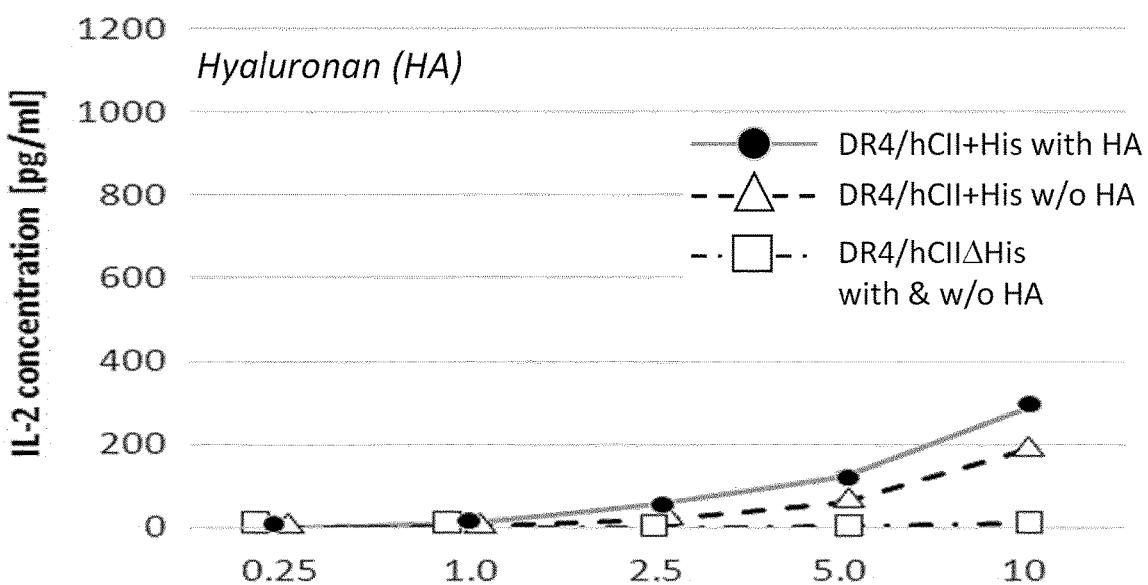
Figure 9

(C)
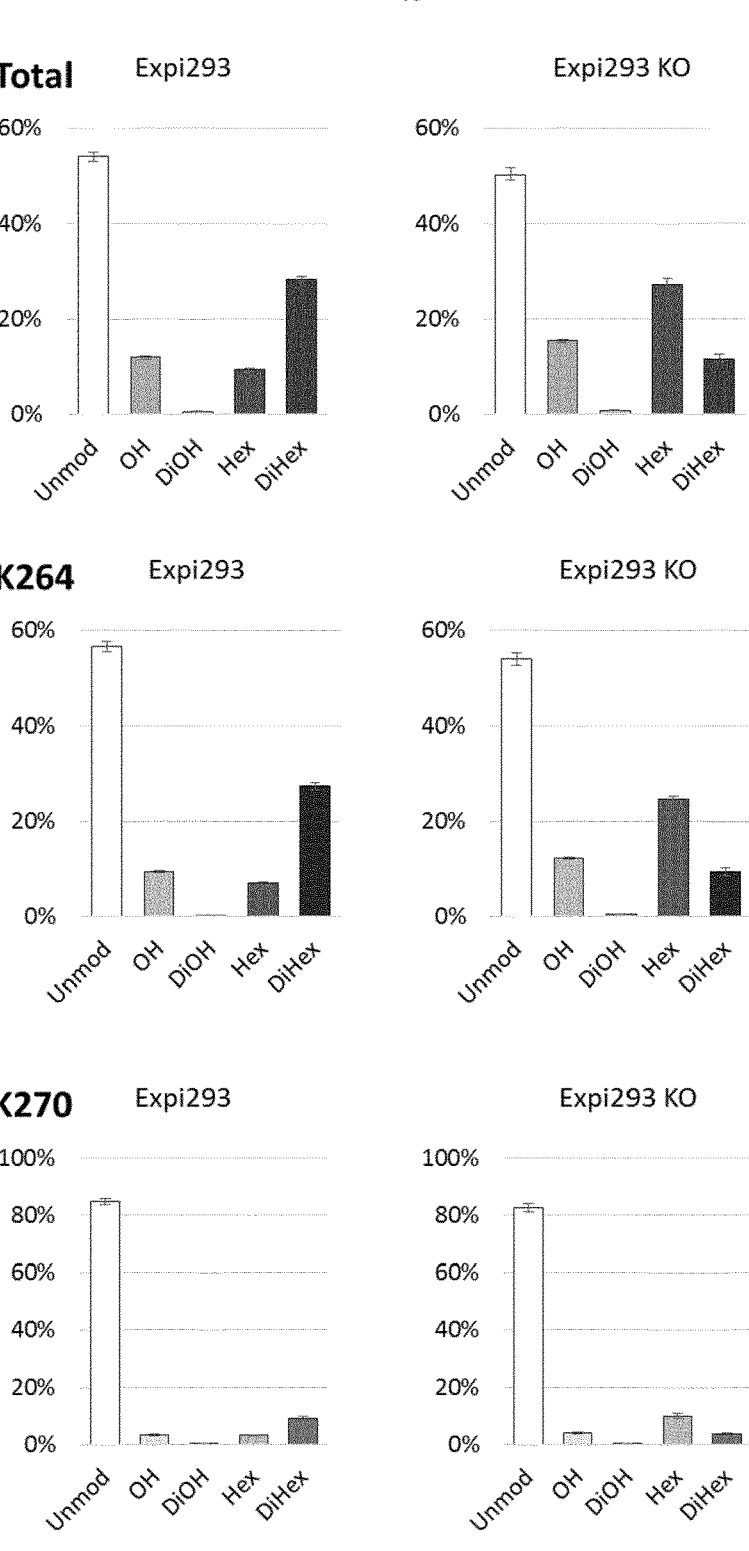
Figure 14 (cont.)

A

- H₂AN tag:    Aq-beta-SGRGRQGGKARAKAKTRSSR      Histone NT

- H₂AC tag:    Aq-beta-HKAKGK                   Histone CT

- NH tag:      Aq-beta-NHNHNHNHNHNH             modified His

B

```
H2A1_HUMAN   MSGRGKQGGKARAKAKTRSSRAGLQFPVGRVHRLLRRGNYAERVGAGAPVYLAAVLEYLT  60
H2A1P_MOUSE  MSGRGKQGGKARAKAKTRSSRAGLQFPVGRVHRLLRRGNYSERVGAGAPVYLAAVLEYLT  60
                          HISTONE NT                * *; ************************

H2A1_HUMAN   AEILELAGNAARDNKKTRIIPRHLQLAIRNDEEINKLLGKVTIAQGGVLPNIQAVLLPKK  120
H2A1P_MOUSE  AEILELAGNAARDNKKTRIIPRHLQLAIRNDEEINKLLGKVTIAQGGVLPNTQAVLLPKK  120
             ***********************************************; ************

H2A1_HUMAN   TESHHKAKGK  130
H2A1P_MOUSE  TESHHKAKGK  130
                 HISTONE CT      *****;******
```

Figure 15

SEQUENCE LISTING

```
<160> NUMBER OF SEQ ID NOS: 43

<210> SEQ ID NO 1
<211> LENGTH: 11
<212> TYPE: PRT
<213> ORGANISM: Homo sapiens
<220> FEATURE:
<223> OTHER INFORMATION: CII peptide 261-271

<400> SEQUENCE: 1

Ala Gly Phe Lys Gly Glu Gln Gly Pro Lys Gly
1               5                   10

<210> SEQ ID NO 2
<211> LENGTH: 11
<212> TYPE: PRT
<213> ORGANISM: Artificial Sequence
<220> FEATURE:
<223> OTHER INFORMATION: CII peptide 261-271
<220> FEATURE:
<221> NAME/KEY: UNSURE
<222> LOCATION: 10
<223> OTHER INFORMATION: Xaa = any proteinogenic amino acids except Lys;
      preferably Xaa = Arg, Ala, Gly or Gln

<400> SEQUENCE: 2

Ala Gly Phe Lys Gly Glu Gln Gly Pro Xaa Gly
1               5                   10

<210> SEQ ID NO 3
<211> LENGTH: 11
<212> TYPE: PRT
<213> ORGANISM: Artificial Sequence
<220> FEATURE:
<223> OTHER INFORMATION: CII peptide 261-271
<220> FEATURE:
<221> NAME/KEY: UNSURE
<222> LOCATION: 7
<223> OTHER INFORMATION: Xaa = any proteinogenic amion acid except Gln;
      preferably Xaa = Ala, Arg, His or Gly

<400> SEQUENCE: 3

Ala Gly Phe Lys Gly Glu Xaa Gly Pro Lys Gly
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CII peptide 261-271
<220> FEATURE:
<221> NAME/KEY: UNSURE
<222> LOCATION: 6
<223> OTHER INFORMATION: Xaa = any proteinogenic amino acid except Glu,
      preferably Xaa = Ala, Asp, Gln or Gly

<400> SEQUENCE: 4

Ala Gly Phe Lys Gly Xaa Gln Gly Pro Lys Gly
1               5                   10

<210> SEQ ID NO 5
<211> LENGTH: 11
<212> TYPE: PRT
<213> ORGANISM: Artificial Sequence
<220> FEATURE:
<223> OTHER INFORMATION: CII peptide 261-271
<220> FEATURE:
<221> NAME/KEY: UNSURE
<222> LOCATION: 5
```

-continued

```
<223> OTHER INFORMATION: Xaa = any proteinogenic amino acid except Gly;
      preferably Xaa = Ala, Ser, Val or Leu

<400> SEQUENCE: 5

Ala Gly Phe Lys Xaa Glu Gln Gly Pro Lys Gly
1               5                   10

<210> SEQ ID NO 6
<211> LENGTH: 11
<212> TYPE: PRT
<213> ORGANISM: Artificial Sequence
<220> FEATURE:
<223> OTHER INFORMATION: CII peptide 261-271
<220> FEATURE:
<221> NAME/KEY: UNSURE
<222> LOCATION: 7
<223> OTHER INFORMATION: Xaa = any proteinogenic amino acid except Gln;
      preferably Xaa = Ala, Arg, His or Gly
<220> FEATURE:
<221> NAME/KEY: UNSURE
<222> LOCATION: 10
<223> OTHER INFORMATION: Xaa = any proteinogenic amino acid except Lys;
      preferably Xaa = Arg, Ala, Gly or Gln

<400> SEQUENCE: 6

Ala Gly Phe Lys Gly Glu Xaa Gly Pro Xaa Gly
1               5                   10

<210> SEQ ID NO 7
<211> LENGTH: 11
<212> TYPE: PRT
<213> ORGANISM: Artificial Sequence
<220> FEATURE:
<223> OTHER INFORMATION: CII peptide 261-271
<220> FEATURE:
<221> NAME/KEY: UNSURE
<222> LOCATION: 6
<223> OTHER INFORMATION: Xaa = any proteinogenic amino acid except Glu;
      preferably Xaa = Ala, Asp, Gln or Gly
<220> FEATURE:
<221> NAME/KEY: UNSURE
<222> LOCATION: 10
<223> OTHER INFORMATION: Xaa = any proteinogenic amino acid except Lys;
      preferably Xaa = Arg, Ala, Gly or Gln

<400> SEQUENCE: 7

Ala Gly Phe Lys Gly Xaa Gln Gly Pro Xaa Gly
1               5                   10

<210> SEQ ID NO 8
<211> LENGTH: 11
<212> TYPE: PRT
<213> ORGANISM: Artificial Sequence
<220> FEATURE:
<223> OTHER INFORMATION: CII peptide 261-271
<220> FEATURE:
<221> NAME/KEY: UNSURE
<222> LOCATION: 5
<223> OTHER INFORMATION: Xaa = any proteinogenic amino acid except Gly;
      preferably Xaa = Ala, Ser, Val or Leu
<220> FEATURE:
<221> NAME/KEY: UNSURE
<222> LOCATION: 10
<223> OTHER INFORMATION: Xaa = any proteinogenic amino acid except Lys;
      preferably Xaa = Arg, Ala, Gly or Gln

<400> SEQUENCE: 8

Ala Gly Phe Lys Xaa Glu Gln Gly Pro Xaa Gly
1               5                   10

<210> SEQ ID NO 9
```

-continued

```
<211> LENGTH: 11
<212> TYPE: PRT
<213> ORGANISM: Artificial Sequence
<220> FEATURE:
<223> OTHER INFORMATION: CII peptide 261-271

<400> SEQUENCE: 9

Ala Gly Phe Lys Gly Glu Gln Gly Pro Arg Gly
1               5                   10

<210> SEQ ID NO 10
<211> LENGTH: 13
<212> TYPE: PRT
<213> ORGANISM: Homo sapiens
<220> FEATURE:
<223> OTHER INFORMATION: CII peptide 261-273

<400> SEQUENCE: 10

Ala Gly Phe Lys Gly Glu Gln Gly Pro Lys Gly Glu Pro
1               5                   10

<210> SEQ ID NO 11
<211> LENGTH: 13
<212> TYPE: PRT
<213> ORGANISM: Artificial Sequence
<220> FEATURE:
<223> OTHER INFORMATION: CII peptide 261-273
<220> FEATURE:
<221> NAME/KEY: UNSURE
<222> LOCATION: 10
<223> OTHER INFORMATION: Xaa = any proteinogenic amino acid except Lys;
      preferably Xaa = Arg, Ala, Gly or Gln

<400> SEQUENCE: 11

Ala Gly Phe Lys Gly Glu Gln Gly Pro Xaa Gly Glu Pro
1               5                   10

<210> SEQ ID NO 12
<211> LENGTH: 13
<212> TYPE: PRT
<213> ORGANISM: Artificial Sequence
<220> FEATURE:
<223> OTHER INFORMATION: CII peptide 261-273

<400> SEQUENCE: 12

Ala Gly Phe Lys Gly Glu Gln Gly Pro Arg Gly Glu Pro
1               5                   10

<210> SEQ ID NO 13
<211> LENGTH: 15
<212> TYPE: PRT
<213> ORGANISM: Homo sapiens
<220> FEATURE:
<223> OTHER INFORMATION: CII peptide 259-273

<400> SEQUENCE: 13

Gly Ile Ala Gly Phe Lys Gly Glu Gln Gly Pro Lys Gly Glu Pro
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: CII peptide 259-273
<220> FEATURE:
<221> NAME/KEY: UNSURE
<222> LOCATION: 12
<223> OTHER INFORMATION: Xaa = any proteinogenic amino acid except Lys;
```

```
     preferably Xaa = Arg, Ala, Gly or Gln

<400> SEQUENCE: 14

Gly Ile Ala Gly Phe Lys Gly Glu Gln Gly Pro Xaa Gly Glu Pro
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: CII peptide 259-273

<400> SEQUENCE: 15

Gly Ile Ala Gly Phe Lys Gly Glu Gln Gly Pro Arg Gly Glu Pro
1               5                   10                  15

<210> SEQ ID NO 16
<211> LENGTH: 275
<212> TYPE: PRT
<213> ORGANISM: Artificial Sequence
<220> FEATURE:
<223> OTHER INFORMATION: DR4 construct alpha-chain

<400> SEQUENCE: 16

Met Lys Leu Cys Ile Leu Leu Ala Val Val Ala Phe Val Gly Leu Ser
1               5                   10                  15

Leu Gly Ile Lys Glu Glu His Val Ile Ile Gln Ala Glu Phe Tyr Leu
            20                  25                  30

Asn Pro Asp Gln Ser Gly Glu Phe Met Phe Asp Phe Asp Gly Asp Glu
        35                  40                  45

Ile Phe His Val Asp Met Ala Lys Lys Glu Thr Val Trp Arg Leu Glu
        50                  55                  60

Glu Phe Gly Arg Phe Ala Ser Phe Glu Ala Gln Gly Ala Leu Ala Asn
65                  70                  75                  80

Ile Ala Val Asp Lys Ala Asn Leu Glu Ile Met Thr Lys Arg Ser Asn
                85                  90                  95

Tyr Thr Pro Ile Thr Asn Val Pro Pro Glu Val Thr Val Leu Thr Asn
            100                 105                 110

Ser Pro Val Glu Leu Arg Glu Pro Asn Val Leu Ile Cys Phe Ile Asp
        115                 120                 125

Lys Phe Thr Pro Pro Val Val Asn Val Thr Trp Leu Arg Asn Gly Lys
        130                 135                 140

Pro Val Thr Thr Gly Val Ser Glu Thr Val Phe Leu Pro Arg Glu Asp
145                 150                 155                 160

His Leu Phe Arg Lys Phe His Tyr Leu Pro Phe Leu Pro Ser Thr Glu
                165                 170                 175

Asp Val Tyr Asp Cys Arg Val Glu His Trp Gly Leu Asp Glu Pro Leu
            180                 185                 190

Leu Lys His Trp Glu Phe Asp Ala Ser Gly Gly Gly Glu Asn Leu Tyr
            195                 200                 205

Phe Gln Gly Gly Gly Gly Ser Leu Thr Asp Thr Leu Gln Ala Glu Thr
        210                 215                 220

Asp Gln Leu Glu Asp Glu Lys Ser Ala Leu Gln Thr Glu Ile Ala Asn
225                 230                 235                 240

Leu Leu Lys Glu Lys Glu Lys Leu Glu Phe Ile Leu Ala Ala His Gly
                245                 250                 255

Gly Gly Gly Ser Gly Leu Asn Asp Ile Phe Glu Ala Gln Lys Ile Glu
```

-continued

```
              260              265              270

Trp His Glu
        275

<210> SEQ ID NO 17
<211> LENGTH: 311
<212> TYPE: PRT
<213> ORGANISM: Artificial Sequence
<220> FEATURE:
<223> OTHER INFORMATION: DR4 construct beta-chain with hCII259-273
      peptide

<400> SEQUENCE: 17

Met Lys Leu Cys Ile Leu Leu Ala Val Val Ala Phe Val Gly Leu Ser
1               5                   10                  15

Leu Gly Ser Ala Trp Ser His Pro Gln Phe Glu Lys Gly Ile Ala Gly
            20                  25                  30

Phe Lys Gly Glu Gln Gly Pro Lys Gly Glu Pro Ser Gly Gly Gly Ser
        35                  40                  45

Leu Val Pro Arg Gly Ser Gly Gly Gly Ser Gly Asp Thr Arg Pro
    50                  55                  60

Arg Phe Leu Glu Gln Val Lys His Glu Cys His Phe Phe Asn Gly Thr
65                  70                  75                  80

Glu Arg Val Arg Phe Leu Asp Arg Tyr Phe Tyr His Gln Glu Glu Tyr
                85                  90                  95

Val Arg Phe Asp Ser Asp Val Gly Glu Tyr Arg Ala Val Thr Glu Leu
            100                 105                 110

Gly Arg Pro Asp Ala Glu Tyr Trp Asn Ser Gln Lys Asp Leu Leu Glu
        115                 120                 125

Gln Lys Arg Ala Ala Val Asp Thr Tyr Cys Arg His Asn Tyr Gly Val
    130                 135                 140

Gly Glu Ser Phe Thr Val Gln Arg Arg Val Tyr Pro Glu Val Thr Val
145                 150                 155                 160

Tyr Pro Ala Lys Thr Gln Pro Leu Gln His His Asn Leu Leu Val Cys
                165                 170                 175

Ser Val Asn Gly Phe Tyr Pro Gly Ser Ile Glu Val Arg Trp Phe Arg
            180                 185                 190

Asn Gly Gln Glu Glu Lys Thr Gly Val Val Ser Thr Gly Leu Ile Gln
        195                 200                 205

Asn Gly Asp Trp Thr Phe Gln Thr Leu Val Met Leu Glu Thr Val Pro
    210                 215                 220

Arg Ser Gly Glu Val Tyr Thr Cys Gln Val Glu His Pro Ser Leu Thr
225                 230                 235                 240

Ser Pro Leu Thr Val Glu Trp Arg Ala Arg Ser Gly Gly Gly Glu Asn
                245                 250                 255

Leu Tyr Phe Gln Gly Gly Gly Ser Arg Ile Ala Arg Leu Glu Glu
            260                 265                 270

Lys Val Lys Thr Leu Lys Ala Gln Asn Ser Glu Leu Ala Ser Thr Ala
        275                 280                 285

Asn Met Leu Arg Glu Gln Val Ala Gln Leu Lys Gln Lys Val Met Asn
    290                 295                 300

His His His His His His
305                 310

<210> SEQ ID NO 18
<211> LENGTH: 248
```

-continued

```
<212> TYPE: PRT
<213> ORGANISM: Artificial Sequence
<220> FEATURE:
<223> OTHER INFORMATION: Minimal DR4 construct alpha-chain

<400> SEQUENCE: 18

Met Lys Leu Cys Ile Leu Leu Ala Val Val Ala Phe Val Gly Leu Ser
1               5                   10                  15

Leu Gly Ile Lys Glu Glu His Val Ile Ile Gln Ala Glu Phe Tyr Leu
            20                  25                  30

Asn Pro Asp Gln Ser Gly Glu Phe Met Phe Asp Phe Asp Gly Asp Glu
        35                  40                  45

Ile Phe His Val Asp Met Ala Lys Lys Glu Thr Val Trp Arg Leu Glu
    50                  55                  60

Glu Phe Gly Arg Phe Ala Ser Phe Glu Ala Gln Gly Ala Leu Ala Asn
65                  70                  75                  80

Ile Ala Val Asp Lys Ala Asn Leu Glu Ile Met Thr Lys Arg Ser Asn
                85                  90                  95

Tyr Thr Pro Ile Thr Asn Val Pro Pro Glu Val Thr Val Leu Thr Asn
            100                 105                 110

Ser Pro Val Glu Leu Arg Glu Pro Asn Val Leu Ile Cys Phe Ile Asp
        115                 120                 125

Lys Phe Thr Pro Pro Val Val Asn Val Thr Trp Leu Arg Asn Gly Lys
    130                 135                 140

Pro Val Thr Thr Gly Val Ser Glu Thr Val Phe Leu Pro Arg Glu Asp
145                 150                 155                 160

His Leu Phe Arg Lys Phe His Tyr Leu Pro Phe Leu Pro Ser Thr Glu
                165                 170                 175

Asp Val Tyr Asp Cys Arg Val Glu His Trp Gly Leu Asp Glu Pro Leu
            180                 185                 190

Leu Lys His Trp Glu Phe Asp Ala Ser Gly Gly Gly Gly Gly Gly Ser
        195                 200                 205

Leu Thr Asp Thr Leu Gln Ala Glu Thr Asp Gln Leu Glu Asp Glu Lys
    210                 215                 220

Ser Ala Leu Gln Thr Glu Ile Ala Asn Leu Leu Lys Glu Lys Glu Lys
225                 230                 235                 240

Leu Glu Phe Ile Leu Ala Ala His
                245

<210> SEQ ID NO 19
<211> LENGTH: 288
<212> TYPE: PRT
<213> ORGANISM: Artificial Sequence
<220> FEATURE:
<223> OTHER INFORMATION: Minimal DR4 construct beta-chain with hCII259-
      273 peptide

<400> SEQUENCE: 19

Met Lys Leu Cys Ile Leu Leu Ala Val Val Ala Phe Val Gly Leu Ser
1               5                   10                  15

Leu Gly Gly Ile Ala Gly Phe Lys Gly Glu Gln Gly Pro Lys Gly Glu
            20                  25                  30

Pro Ser Gly Gly Gly Ser Gly Gly Gly Ser Gly Asp Thr Arg Pro
        35                  40                  45

Arg Phe Leu Glu Gln Val Lys His Glu Cys His Phe Phe Asn Gly Thr
    50                  55                  60

Glu Arg Val Arg Phe Leu Asp Arg Tyr Phe Tyr His Gln Glu Glu Tyr
```

```
                65                    70                    75                    80
Val Arg Phe Asp Ser Asp Val Gly Glu Tyr Arg Ala Val Thr Glu Leu
                    85                    90                    95

Gly Arg Pro Asp Ala Glu Tyr Trp Asn Ser Gln Lys Asp Leu Leu Glu
                    100                   105                   110

Gln Lys Arg Ala Ala Val Asp Thr Tyr Cys Arg His Asn Tyr Gly Val
                    115                   120                   125

Gly Glu Ser Phe Thr Val Gln Arg Arg Val Tyr Pro Glu Val Thr Val
                    130                   135                   140

Tyr Pro Ala Lys Thr Gln Pro Leu Gln His His Asn Leu Leu Val Cys
        145                   150                   155                   160

Ser Val Asn Gly Phe Tyr Pro Gly Ser Ile Glu Val Arg Trp Phe Arg
                    165                   170                   175

Asn Gly Gln Glu Glu Lys Thr Gly Val Val Ser Thr Gly Leu Ile Gln
                    180                   185                   190

Asn Gly Asp Trp Thr Phe Gln Thr Leu Val Met Leu Glu Thr Val Pro
                    195                   200                   205

Arg Ser Gly Glu Val Tyr Thr Cys Gln Val Glu His Pro Ser Leu Thr
        210                   215                   220

Ser Pro Leu Thr Val Glu Trp Arg Ala Arg Ser Gly Gly Gly Gly Gly
225                   230                   235                   240

Gly Ser Arg Ile Ala Arg Leu Glu Glu Lys Val Lys Thr Leu Lys Ala
                    245                   250                   255

Gln Asn Ser Glu Leu Ala Ser Thr Ala Asn Met Leu Arg Glu Gln Val
                    260                   265                   270

Ala Gln Leu Lys Gln Lys Val Met Asn His His His His His His
                    275                   280                   285

<210> SEQ ID NO 20
<211> LENGTH: 311
<212> TYPE: PRT
<213> ORGANISM: Artificial Sequence
<220> FEATURE:
<223> OTHER INFORMATION: DR4 construct beta-chain with hCLIPmut

<400> SEQUENCE: 20

Met Lys Leu Cys Ile Leu Leu Ala Val Val Ala Phe Val Gly Leu Ser
1               5                     10                    15

Leu Gly Ser Ala Trp Ser His Pro Gln Phe Glu Lys Pro Val Ser Lys
                    20                    25                    30

Ala Arg Met Ala Thr Gly Ala Leu Ala Gln Ala Ser Gly Gly Gly Ser
                    35                    40                    45

Leu Val Pro Arg Gly Ser Gly Gly Gly Ser Gly Asp Thr Arg Pro
        50                    55                    60

Arg Phe Leu Glu Gln Val Lys His Glu Cys His Phe Phe Asn Gly Thr
65                    70                    75                    80

Glu Arg Val Arg Phe Leu Asp Arg Tyr Phe Tyr His Gln Glu Glu Tyr
                    85                    90                    95

Val Arg Phe Asp Ser Asp Val Gly Glu Tyr Arg Ala Val Thr Glu Leu
                    100                   105                   110

Gly Arg Pro Asp Ala Glu Tyr Trp Asn Ser Gln Lys Asp Leu Leu Glu
                    115                   120                   125

Gln Lys Arg Ala Ala Val Asp Thr Tyr Cys Arg His Asn Tyr Gly Val
        130                   135                   140

Gly Glu Ser Phe Thr Val Gln Arg Arg Val Tyr Pro Glu Val Thr Val
```

```
145             150             155             160

Tyr Pro Ala Lys Thr Gln Pro Leu Gln His His Asn Leu Leu Val Cys
            165             170             175

Ser Val Asn Gly Phe Tyr Pro Gly Ser Ile Glu Val Arg Trp Phe Arg
            180             185             190

Asn Gly Gln Glu Glu Lys Thr Gly Val Val Ser Thr Gly Leu Ile Gln
            195             200             205

Asn Gly Asp Trp Thr Phe Gln Thr Leu Val Met Leu Glu Thr Val Pro
    210             215             220

Arg Ser Gly Glu Val Tyr Thr Cys Gln Val Glu His Pro Ser Leu Thr
225             230             235             240

Ser Pro Leu Thr Val Glu Trp Arg Ala Arg Ser Gly Gly Gly Glu Asn
                245             250             255

Leu Tyr Phe Gln Gly Gly Gly Ser Arg Ile Ala Arg Leu Glu Glu
            260             265             270

Lys Val Lys Thr Leu Lys Ala Gln Asn Ser Glu Leu Ala Ser Thr Ala
            275             280             285

Asn Met Leu Arg Glu Gln Val Ala Gln Leu Lys Gln Lys Val Met Asn
    290             295             300

His His His His His His
305             310

<210> SEQ ID NO 21
<211> LENGTH: 290
<212> TYPE: PRT
<213> ORGANISM: Artificial Sequence
<220> FEATURE:
<223> OTHER INFORMATION: Aq construct alpha-chain

<400> SEQUENCE: 21

Met Lys Leu Cys Ile Leu Leu Ala Val Val Ala Phe Val Gly Leu Ser
1               5               10              15

Leu Gly Glu Asp Asp Ile Glu Ala Asp His Val Gly Phe Tyr Gly Ile
                20              25              30

Val Val Tyr Gln Ser Pro Gly Asp Ile Gly Gln Tyr Thr His Glu Phe
            35              40              45

Asp Gly Asp Glu Trp Phe Tyr Val Asp Leu Asp Lys Lys Glu Thr Val
    50              55              60

Trp Met Leu Pro Glu Phe Gly Gln Leu Thr Ser Phe Asp Pro Gln Gly
65              70              75              80

Gly Leu Gln Asn Ile Ala Thr Gly Lys His Asn Leu Gly Gly Trp Thr
                85              90              95

Lys Arg Ser Asn Phe Thr Pro Ala Thr Asn Glu Ala Pro Gln Ala Thr
            100             105             110

Val Phe Pro Lys Ser Pro Val Leu Leu Gly Gln Pro Asn Thr Leu Ile
            115             120             125

Cys Phe Val Asp Asn Ile Phe Pro Pro Val Ile Asn Ile Thr Trp Leu
    130             135             140

Arg Asn Ser Lys Ser Val Thr Asp Gly Val Tyr Glu Thr Ser Phe Leu
145             150             155             160

Val Asn Arg Asp His Ser Phe His Lys Leu Ser Tyr Leu Thr Phe Ile
                165             170             175

Pro Ser Asp Asp Asp Ile Tyr Asp Cys Lys Val Glu His Trp Gly Leu
                180             185             190

Asp Glu Pro Val Leu Lys His Trp Glu Pro Glu Ile Pro Ala Thr Met
```

-continued

```
              195               200               205

Ser Glu Leu Thr Glu Thr Val Ser Gly Gly Gly Glu Asn Leu Tyr Phe
    210               215               220

Gln Gly Gly Gly Gly Ser Leu Thr Asp Thr Leu Gln Ala Glu Thr Asp
225               230               235               240

Gln Leu Glu Asp Glu Lys Ser Ala Leu Gln Thr Glu Ile Ala Asn Leu
              245               250               255

Leu Lys Glu Lys Glu Lys Leu Glu Phe Ile Leu Ala Ala His Gly Gly
              260               265               270

Gly Gly Ser Gly Leu Asn Asp Ile Phe Glu Ala Gln Lys Ile Glu Trp
              275               280               285

His Glu
    290

<210> SEQ ID NO 22
<211> LENGTH: 316
<212> TYPE: PRT
<213> ORGANISM: Artificial Sequence
<220> FEATURE:
<223> OTHER INFORMATION: Aq construct beta-chain with rat CII259-273
      peptide

<400> SEQUENCE: 22

Met Lys Leu Cys Ile Leu Leu Ala Val Val Ala Phe Val Gly Leu Ser
1               5               10                15

Leu Gly Ser Ala Trp Ser His Pro Gln Phe Glu Lys Gly Ile Ala Gly
              20               25                30

Phe Lys Gly Glu Gln Gly Pro Lys Gly Glu Thr Ser Gly Gly Gly Ser
              35               40                45

Leu Val Pro Arg Gly Ser Gly Gly Gly Ser Glu Arg His Phe Val
    50               55               60

Ala Gln Leu Lys Gly Glu Cys Tyr Phe Thr Asn Gly Thr Gln Arg Ile
65                70               75                80

Arg Ser Val Asn Arg Tyr Ile Tyr Asn Arg Glu Glu Trp Val Arg Phe
              85               90                95

Asp Ser Asp Val Gly Glu Tyr Arg Ala Val Thr Glu Leu Gly Arg Pro
              100              105               110

Asp Ala Glu Tyr Trp Asn Ser Gln Pro Glu Ile Leu Glu Arg Thr Arg
              115              120               125

Ala Glu Val Asp Thr Val Cys Arg His Asn Tyr Glu Gly Val Glu Thr
    130              135               140

His Thr Ser Leu Arg Arg Leu Glu Gln Pro Asn Val Ala Ile Ser Leu
145              150               155               160

Ser Arg Thr Glu Ala Leu Asn His His Asn Thr Leu Val Cys Ser Val
              165              170               175

Thr Asp Phe Tyr Pro Ala Lys Ile Lys Val Arg Trp Phe Arg Asn Gly
              180              185               190

Gln Glu Glu Thr Val Gly Val Ser Ser Thr Gln Leu Ile Arg Asn Gly
              195              200               205

Asp Trp Thr Phe Gln Val Leu Val Met Leu Glu Met Thr Pro His Gln
    210              215               220

Gly Glu Val Tyr Thr Cys His Val Glu His Pro Ser Leu Lys Ser Pro
225              230               235               240

Ile Thr Val Glu Trp Arg Ala Gln Ser Glu Ser Ala Arg Ser Lys Ser
              245              250               255
```

-continued

```
Gly Gly Gly Glu Asn Leu Tyr Phe Gln Gly Gly Gly Ser Arg Ile
            260                 265                 270

Ala Arg Leu Glu Glu Lys Val Lys Thr Leu Lys Ala Gln Asn Ser Glu
        275                 280                 285

Leu Ala Ser Thr Ala Asn Met Leu Arg Glu Gln Val Ala Gln Leu Lys
    290                 295                 300

Gln Lys Val Met Asn His His His His His His
305                 310                 315

<210> SEQ ID NO 23
<211> LENGTH: 310
<212> TYPE: PRT
<213> ORGANISM: Artificial Sequence
<220> FEATURE:
<223> OTHER INFORMATION: Aq construct beta-chain with rat CII259-273
      peptide without His-tag

<400> SEQUENCE: 23

Met Lys Leu Cys Ile Leu Leu Ala Val Val Ala Phe Val Gly Leu Ser
1               5                   10                  15

Leu Gly Ser Ala Trp Ser His Pro Gln Phe Glu Lys Gly Ile Ala Gly
            20                  25                  30

Phe Lys Gly Glu Gln Gly Pro Lys Gly Glu Thr Ser Gly Gly Gly Ser
        35                  40                  45

Leu Val Pro Arg Gly Ser Gly Gly Gly Ser Glu Arg His Phe Val
    50                  55                  60

Ala Gln Leu Lys Gly Glu Cys Tyr Phe Thr Asn Gly Thr Gln Arg Ile
65                  70                  75                  80

Arg Ser Val Asn Arg Tyr Ile Tyr Asn Arg Glu Glu Trp Val Arg Phe
                85                  90                  95

Asp Ser Asp Val Gly Glu Tyr Arg Ala Val Thr Glu Leu Gly Arg Pro
            100                 105                 110

Asp Ala Glu Tyr Trp Asn Ser Gln Pro Glu Ile Leu Glu Arg Thr Arg
        115                 120                 125

Ala Glu Val Asp Thr Val Cys Arg His Asn Tyr Glu Gly Val Glu Thr
    130                 135                 140

His Thr Ser Leu Arg Arg Leu Glu Gln Pro Asn Val Ala Ile Ser Leu
145                 150                 155                 160

Ser Arg Thr Glu Ala Leu Asn His His Asn Thr Leu Val Cys Ser Val
                165                 170                 175

Thr Asp Phe Tyr Pro Ala Lys Ile Lys Val Arg Trp Phe Arg Asn Gly
            180                 185                 190

Gln Glu Glu Thr Val Gly Val Ser Ser Thr Gln Leu Ile Arg Asn Gly
        195                 200                 205

Asp Trp Thr Phe Gln Val Leu Val Met Leu Glu Met Thr Pro His Gln
    210                 215                 220

Gly Glu Val Tyr Thr Cys His Val Glu His Pro Ser Leu Lys Ser Pro
225                 230                 235                 240

Ile Thr Val Glu Trp Arg Ala Gln Ser Glu Ser Ala Arg Ser Lys Ser
                245                 250                 255

Gly Gly Gly Glu Asn Leu Tyr Phe Gln Gly Gly Gly Gly Ser Arg Ile
            260                 265                 270

Ala Arg Leu Glu Glu Lys Val Lys Thr Leu Lys Ala Gln Asn Ser Glu
        275                 280                 285

Leu Ala Ser Thr Ala Asn Met Leu Arg Glu Gln Val Ala Gln Leu Lys
    290                 295                 300
```

-continued

```
Gln Lys Val Met Asn His
305                 310

<210> SEQ ID NO 24
<211> LENGTH: 316
<212> TYPE: PRT
<213> ORGANISM: Artificial Sequence
<220> FEATURE:
<223> OTHER INFORMATION: Aq construct beta-chain with mCLIP peptide

<400> SEQUENCE: 24

Met Lys Leu Cys Ile Leu Leu Ala Val Val Ala Phe Val Gly Leu Ser
1               5                   10                  15

Leu Gly Ser Ala Trp Ser His Pro Gln Phe Glu Lys Pro Val Ser Gln
                20                  25                  30

Ala Arg Met Ala Thr Pro Leu Leu Met Arg Pro Ser Gly Gly Gly Ser
            35                  40                  45

Leu Val Pro Arg Gly Ser Gly Gly Gly Ser Glu Arg His Phe Val
        50                  55                  60

Ala Gln Leu Lys Gly Glu Cys Tyr Phe Thr Asn Gly Thr Gln Arg Ile
65                  70                  75                  80

Arg Ser Val Asn Arg Tyr Ile Tyr Asn Arg Glu Glu Trp Val Arg Phe
                85                  90                  95

Asp Ser Asp Val Gly Glu Tyr Arg Ala Val Thr Glu Leu Gly Arg Pro
            100                 105                 110

Asp Ala Glu Tyr Trp Asn Ser Gln Pro Glu Ile Leu Glu Arg Thr Arg
            115                 120                 125

Ala Glu Val Asp Thr Val Cys Arg His Asn Tyr Glu Gly Val Glu Thr
        130                 135                 140

His Thr Ser Leu Arg Arg Leu Glu Gln Pro Asn Val Ala Ile Ser Leu
145                 150                 155                 160

Ser Arg Thr Glu Ala Leu Asn His His Asn Thr Leu Val Cys Ser Val
                165                 170                 175

Thr Asp Phe Tyr Pro Ala Lys Ile Lys Val Arg Trp Phe Arg Asn Gly
            180                 185                 190

Gln Glu Glu Thr Val Gly Val Ser Ser Thr Gln Leu Ile Arg Asn Gly
            195                 200                 205

Asp Trp Thr Phe Gln Val Leu Val Met Leu Glu Met Thr Pro His Gln
        210                 215                 220

Gly Glu Val Tyr Thr Cys His Val Glu His Pro Ser Leu Lys Ser Pro
225                 230                 235                 240

Ile Thr Val Glu Trp Arg Ala Gln Ser Glu Ser Ala Arg Ser Lys Ser
                245                 250                 255

Gly Gly Gly Glu Asn Leu Tyr Phe Gln Gly Gly Gly Ser Arg Ile
            260                 265                 270

Ala Arg Leu Glu Glu Lys Val Lys Thr Leu Lys Ala Gln Asn Ser Glu
            275                 280                 285

Leu Ala Ser Thr Ala Asn Met Leu Arg Glu Gln Val Ala Gln Leu Lys
        290                 295                 300

Gln Lys Val Met Asn His His His His His His
305                 310                 315

<210> SEQ ID NO 25
<211> LENGTH: 310
<212> TYPE: PRT
<213> ORGANISM: Artificial Sequence
```

-continued

```
<220> FEATURE:
<223> OTHER INFORMATION: Aq construct beta-chain with mCLIP peptide
     without His-tag

<400> SEQUENCE: 25

Met Lys Leu Cys Ile Leu Leu Ala Val Val Ala Phe Val Gly Leu Ser
1               5                   10                  15

Leu Gly Ser Ala Trp Ser His Pro Gln Phe Glu Lys Pro Val Ser Gln
            20                  25                  30

Ala Arg Met Ala Thr Pro Leu Leu Met Arg Pro Ser Gly Gly Gly Ser
        35                  40                  45

Leu Val Pro Arg Gly Ser Gly Gly Gly Ser Glu Arg His Phe Val
    50                  55                  60

Ala Gln Leu Lys Gly Glu Cys Tyr Phe Thr Asn Gly Thr Gln Arg Ile
65                  70                  75                  80

Arg Ser Val Asn Arg Tyr Ile Tyr Asn Arg Glu Glu Trp Val Arg Phe
                85                  90                  95

Asp Ser Asp Val Gly Glu Tyr Arg Ala Val Thr Glu Leu Gly Arg Pro
            100                 105                 110

Asp Ala Glu Tyr Trp Asn Ser Gln Pro Glu Ile Leu Glu Arg Thr Arg
            115                 120                 125

Ala Glu Val Asp Thr Val Cys Arg His Asn Tyr Glu Gly Val Glu Thr
    130                 135                 140

His Thr Ser Leu Arg Arg Leu Glu Gln Pro Asn Val Ala Ile Ser Leu
145                 150                 155                 160

Ser Arg Thr Glu Ala Leu Asn His His Asn Thr Leu Val Cys Ser Val
                165                 170                 175

Thr Asp Phe Tyr Pro Ala Lys Ile Lys Val Arg Trp Phe Arg Asn Gly
            180                 185                 190

Gln Glu Glu Thr Val Gly Val Ser Ser Thr Gln Leu Ile Arg Asn Gly
            195                 200                 205

Asp Trp Thr Phe Gln Val Leu Val Met Leu Glu Met Thr Pro His Gln
    210                 215                 220

Gly Glu Val Tyr Thr Cys His Val Glu His Pro Ser Leu Lys Ser Pro
225                 230                 235                 240

Ile Thr Val Glu Trp Arg Ala Gln Ser Glu Ser Ala Arg Ser Lys Ser
            245                 250                 255

Gly Gly Gly Glu Asn Leu Tyr Phe Gln Gly Gly Gly Ser Arg Ile
            260                 265                 270

Ala Arg Leu Glu Glu Lys Val Lys Thr Leu Lys Ala Gln Asn Ser Glu
        275                 280                 285

Leu Ala Ser Thr Ala Asn Met Leu Arg Glu Gln Val Ala Gln Leu Lys
    290                 295                 300

Gln Lys Val Met Asn His
305                 310

<210> SEQ ID NO 26
<211> LENGTH: 40
<212> TYPE: PRT
<213> ORGANISM: Homo sapiens
<220> FEATURE:
<223> OTHER INFORMATION: cFos domain

<400> SEQUENCE: 26

Leu Thr Asp Thr Leu Gln Ala Glu Thr Asp Gln Leu Glu Asp Glu Lys
1               5                   10                  15
```

```
Ser Ala Leu Gln Thr Glu Ile Ala Asn Leu Leu Lys Glu Lys Glu Lys
            20                  25                  30

Leu Glu Phe Ile Leu Ala Ala His
        35                  40

<210> SEQ ID NO 27
<211> LENGTH: 40
<212> TYPE: PRT
<213> ORGANISM: Homo sapiens
<220> FEATURE:
<223> OTHER INFORMATION: cJun domain

<400> SEQUENCE: 27

Arg Ile Ala Arg Leu Glu Glu Lys Val Lys Thr Leu Lys Ala Gln Asn
1               5                   10                  15

Ser Glu Leu Ala Ser Thr Ala Asn Met Leu Arg Glu Gln Val Ala Gln
            20                  25                  30

Leu Lys Gln Lys Val Met Asn His
        35                  40

<210> SEQ ID NO 28
<211> LENGTH: 15
<212> TYPE: PRT
<213> ORGANISM: Homo sapiens
<220> FEATURE:
<223> OTHER INFORMATION: mutated human CLIP-peptide

<400> SEQUENCE: 28

Pro Val Ser Lys Ala Arg Met Ala Thr Gly Ala Leu Ala Gln Ala
1               5                   10                  15

<210> SEQ ID NO 29
<211> LENGTH: 15
<212> TYPE: PRT
<213> ORGANISM: Homo sapiens
<220> FEATURE:
<223> OTHER INFORMATION: rat CII-peptide 259-273

<400> SEQUENCE: 29

Gly Ile Ala Gly Phe Lys Gly Glu Gln Gly Pro Lys Gly Glu Thr
1               5                   10                  15

<210> SEQ ID NO 30
<211> LENGTH: 10
<212> TYPE: PRT
<213> ORGANISM: Artificial Sequence
<220> FEATURE:
<223> OTHER INFORMATION: streptavidin-tag

<400> SEQUENCE: 30

Ser Ala Trp Ser His Pro Gln Phe Glu Lys
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Chondroitin-binding peptide

<400> SEQUENCE: 31

Glu Lys Arg Ile Trp Phe Pro Tyr Arg Arg Phe
1               5                   10

<210> SEQ ID NO 32
```

```
<211> LENGTH: 11
<212> TYPE: PRT
<213> ORGANISM: Artificial Sequence
<220> FEATURE:
<223> OTHER INFORMATION: chondroitin-binding peptide

<400> SEQUENCE: 32

Tyr Lys Thr Asn Phe Arg Arg Tyr Tyr Arg Phe
1               5                   10

<210> SEQ ID NO 33
<211> LENGTH: 11
<212> TYPE: PRT
<213> ORGANISM: Artificial Sequence
<220> FEATURE:
<223> OTHER INFORMATION: chondroitin-binding peptide

<400> SEQUENCE: 33

Val Leu Ile Arg His Phe Arg Lys Arg Tyr Tyr
1               5                   10

<210> SEQ ID NO 34
<211> LENGTH: 20
<212> TYPE: PRT
<213> ORGANISM: Artificial Sequence
<220> FEATURE:
<223> OTHER INFORMATION: Histone NT tag

<400> SEQUENCE: 34

Ser Gly Arg Gly Lys Gln Gly Gly Lys Ala Arg Ala Lys Ala Lys Thr
1               5                   10                  15

Arg Ser Ser Arg
            20

<210> SEQ ID NO 35
<211> LENGTH: 12
<212> TYPE: PRT
<213> ORGANISM: Artificial Sequence
<220> FEATURE:
<223> OTHER INFORMATION: modified his-tag

<400> SEQUENCE: 35

Asn His Asn His Asn His Asn His Asn His Asn His
1               5                   10

<210> SEQ ID NO 36
<211> LENGTH: 19
<212> TYPE: PRT
<213> ORGANISM: Artificial Sequence
<220> FEATURE:
<223> OTHER INFORMATION: HAT-tag

<400> SEQUENCE: 36

Lys Asp His Leu Ile His Asn Val His Lys Glu Glu His Ala His Ala
1               5                   10                  15

His Asn Lys

<210> SEQ ID NO 37
<211> LENGTH: 130
<212> TYPE: PRT
<213> ORGANISM: Homo sapiens

<400> SEQUENCE: 37

Met Ser Gly Arg Gly Lys Gln Gly Gly Lys Ala Arg Ala Lys Ala Lys
1               5                   10                  15
```

```
Thr Arg Ser Ser Arg Ala Gly Leu Gln Phe Pro Val Gly Arg Val His
        20                  25                  30

Arg Leu Leu Arg Lys Gly Asn Tyr Ala Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Lys Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130
```

```
<210> SEQ ID NO 38
<211> LENGTH: 130
<212> TYPE: PRT
<213> ORGANISM: Mus musculus

<400> SEQUENCE: 38
```

```
Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
        20                  25                  30

Arg Leu Leu Arg Lys Gly Asn Tyr Ser Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Arg Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130
```

```
<210> SEQ ID NO 39
<211> LENGTH: 30
<212> TYPE: PRT
<213> ORGANISM: Artificial Sequence
<220> FEATURE:
<223> OTHER INFORMATION: hCII259-273 with N-terminal and C-terminal
      sequence

<400> SEQUENCE: 39
```

```
Ser Ala Trp Ser His Pro Gln Phe Glu Lys Gly Ile Ala Gly Phe Lys
1               5                   10                  15

Gly Glu Gln Gly Pro Lys Gly Glu Pro Ser Gly Gly Gly Ser
            20                  25                  30
```

```
<210> SEQ ID NO 40
<211> LENGTH: 6
```

-continued

```
<212> TYPE: PRT
<213> ORGANISM: Artificial Sequence
<220> FEATURE:
<223> OTHER INFORMATION: H2AC tag

<400> SEQUENCE: 40

His Lys Ala Lys Gly Lys
1               5

<210> SEQ ID NO 41
<211> LENGTH: 6
<212> TYPE: PRT
<213> ORGANISM: Artificial Sequence
<220> FEATURE:
<223> OTHER INFORMATION: 6XHis

<400> SEQUENCE: 41

His His His His His His
1               5

<210> SEQ ID NO 42
<211> LENGTH: 7
<212> TYPE: PRT
<213> ORGANISM: Artificial Sequence
<220> FEATURE:
<223> OTHER INFORMATION: 7xHis

<400> SEQUENCE: 42

His His His His His His His
1               5

<210> SEQ ID NO 43
<211> LENGTH: 6
<212> TYPE: PRT
<213> ORGANISM: Artificial Sequence
<220> FEATURE:
<223> OTHER INFORMATION: Histone CT tag

<400> SEQUENCE: 43

His Lys Ala Lys Gly Lys
1               5
```

HLA-DR/CII PEPTIDE COMPLEXES FOR TREATING ARTHRITIS

CROSS REFERENCE TO RELATED APPLICATIONS

This application is a national stage application under 35 U.S.C. 371 and claims the benefit of PCT Application No. PCT/EP2020/072280 having an international filing date of 7 Aug. 2020, which designated the United States, and which PCT application claimed the benefit of Europe patent application Ser. No. 19/191,077.7 filed 9 Aug. 2019, the contents of each of which are incorporated herein by reference in their entireties.

TECHNICAL FIELD

The present invention relates to HLA-DR/CII peptide complexes comprising a chondroitin-binding peptide at the C-terminal end of the polypeptide comprising the HLA-DR alpha chain and/or the HLA-DR beta chain, wherein the CII peptide is fused to the N-terminus of the HLA-DR alpha chain or the HLA-DR beta chain by a linker peptide, for use in treating chronic inflammatory diseases, such as arthritis, in human patients. The lysines in the CII peptide, particularly the first lysine in the CII peptide, may be post-translationally modified. The invention further relates to methods of producing said HLA-DR/CII peptide complexes in mammalian cells.

SEQUENCE LISTING

The instant application contains a Sequence Listing, which has been submitted electronically in XML format and is hereby incorporated by reference in its entirety. Said XML copy, created on Apr. 9, 2025, is named Updated_SL_9Apr2025 and is 37,233 bytes in size.

TECHNOLOGICAL BACKGROUND

Rheumatoid arthritis (RA) is a common, severe disease representing a major health concern with 4-7 million affected people in Europe. It is caused by an aberrant autoimmune inflammation of joints associated with pain, progressive cartilage and bone destruction leading to functional disability and ultimately immobility/invalidity if not adequately treated. Today's pharmaceutical treatment is initiated immediately upon establishment of the clinical diagnosis and is effective in 60-70% of the cases, but does not achieve cure from the disease. Drug treatment predominantly targets common effector pathways of inflammation thereby causing broad immunosuppressive effects associated with an increased risk for infection.

The immunogenetics of RA suggests a key role for aberrant pathways of T-cell activation in the initiation and/or perpetuation of disease. In the T-cell activation process, CD4+ T-cells are engaged by antigenic peptide fragments complexed with human major histocompatibility complex (MHC) class II (such as human leukocyte antigen-DR isotype (HLA-DR)), leading to their activation in the context of co-stimulatory signals provided by professional antigen presenting cells. The strongest evidence supporting a role for CD4+ T cells in disease pathogenesis is the genetic association between RA and certain alleles of the HLA-DRB1 locus coding for an amino acid consensus motif Q/R R/K R A A on the beta-chain of the peptide binding pocket of the MHC class II molecule HLA-DR (amino acid position 70-74, the so called "shared epitope") (Gregersen P K et al., Arthritis Rheum. 1987; 30:1205-1213). Compelling evidence for a pathogenic role of T cells in RA is further provided by their frequent detectability in inflammatory synovial infiltrates of moderate to severe disease indicating their collaboration with B cells in local immune reactions to promote the maturation of specific autoantibody responses. Moreover, an impaired CD4+CD25 (hi) regulatory T cell (Treg) function has been suggested to be involved in the pathogenesis of RA. Accordingly, the dysregulated chronically activated T cell compartment in RA represents a key target for therapeutic immunomodulatory intervention.

RA is today believed to start many years before clinical onset. RA as polygenetic disease with the above mentioned shared-epitope encoding alleles at the HLA-DRB1 locus as the strongest risk factor, develops in respectively predisposed individuals. However, yet ill-defined environmental and/or life style factors (smoking) are also involved in triggering an autoimmune response associated with the generation of antibodies to IgG (rheumatoid factors) and to citrullinated proteins (ACPA) that can persist in arthritis prone but still healthy individuals for a preclinical period of up to two decades. Around clinical onset, an immune response to type II collagen (CII) and to citrullinated CII is detectable (Burkhardt H et al., Eur J Immunol. 2005; 35:1643-52). CII is the major protein component in joint cartilage. RA patients that carry the DRB1*0401 allele (50% of Caucasian RA-patients) have been demonstrated to harbor T cells in their repertoire that specifically respond to a major CII epitope corresponding to the amino acid sequence 259-273 of the triple helical CII region. The T cell determinant critical for activation of the T cell receptor (TCR) has been described to be dependent on the physiologically galactosylated hydroxylysine residue at position 264 (Baecklund J. et al., Proc Natl Acad Sci USA. 2002; 99:9960-5). However, in humans this dependency may be less strict compared to established mouse models and autoreactive T cells recognizing the naked, not post-translationally modified CII peptide and the post-translationally modified CII peptide seem to be detectable to a larger relative extent in human patients with RA as compared with CII immunized mice.

The most commonly used animal model for RA is collagen-induced arthritis (CIA) in mice. Experimental arthritis is MHC class II dependent, associated with the murine class II allele Aq and dependent on T cell recognition of the galactosylated 259-273 CII-epitope (Holmdahl R. et al. Ageing Res Rev. 2002; 1:135-47). CIA is used as a standard model for testing the therapeutic efficiency of new compounds with antiarthritic potential in drug development. Thus a variety of protocols have been developed to induce antigen specific tolerance and one of the candidate antigens in preventing and curing arthritis through vaccination has been CII. The most efficient protocol in adult mice, and so far without any observable side effects, is to induce tolerance by intravenous injection of a recombinant protein complex consisting of the extracellular domains of the MHC class II molecule Aq with the major antigen CII peptide in the binding pocket i.e. the galactosylated CII259-273 peptide, or Aq/galCII complex (Dzhambazov B et al. J Immunol 2006; 176:1525-1533). Injection of the Aq/galCII complex after immunization with CII, but before the onset of arthritis, led to an almost complete prevention of arthritis development and treatment of mice with a chronic relapsing arthritis led to down-regulation of the inflammatory activity. The tolerogenic Aq/galCII effect was dominant as its antiarthritic potential could be transferred with T cells from treated mice to naïve recipients.

Complexes of Aq containing CII peptide without galactosylation at position 264 remained without effect. The reason for this remarkably selective regulatory effect is likely related to the fact that galactosylated CII is expressed only in cartilage (Baecklund J. et al., Proc Natl Acad Sci USA. 2002; 99:9960-5) whereas non-glycosylated CII is expressed also in the thymus (Chin R. K., et al., J Immunol. 2006; 177:290-7). Thus, the T cell response to unglycosylated CII is regulated by central tolerance whereas the T cell response to the galactosylated antigen is regulated by peripheral tolerance mechanisms. A disturbance of the physiologic peripheral self-tolerance especially to structural components of the diarthrodial joints as being a major driving force in RA pathogenesis has therefore been suggested and its reestablishment is the rationale for the development of a tolerogenic treatment strategy. This approach consists of the parenteral administration of DR4/CII complexes to biomarker selected human RA-patients identified as carriers of the DRB1*0401 allele by preceding genotyping to induce immune regulatory T cells that downregulate arthritogenic T cell responses by bystander suppression. In contrast to conventional treatment approaches the mechanism of action consists of a selective immunomodulation of arthritogenic adaptive immune responses while leaving protective immunity unaffected. It is a personalized or HLA-restricted treatment approach that is confined to patients with a certain HLA allele, such as DRB1*0401 positive patients. In addition, preclinical data in CIA treatment suggest that the DR4/galCII complex has the potential to achieve a therapeutic effect in established RA as well as a prophylactic effect in individuals at risk of developing RA, i.e., before disease manifestation. Accordingly, the mode of action is fundamentally different from already established therapies in RA.

WO2007/058587 A1 relates to a "compound comprising an autoantigenic peptide and a carrier with a MHC binding motif" and discloses a compound comprising (a) a peptide and (b) a carrier, wherein said peptide has at least the motif X-X-X-X-X-X-X and wherein at least one amino acid residue X is glycosylated. Furthermore, the peptide is being linked to the peptide binding protein and said carrier comprises at least a MHC binding motif, wherein the linking may be covalently. However, the peptide is not expressed together with the MHC II protein by the same host cell or is linked to the MHC II protein via a linker peptide.

More recent evidence supports that in humans also MHC II/CII peptide complexes without post-translational modifications may be active in inducing tolerance. Thus, while post-translational modification of lysine in the CII peptide is most likely advantageous also in humans, it may not be strictly required.

MHC II complexes have been regularly prepared carrying a polyhistidine tag in order to simplify complex purification. Polyhistidine tags are affinity tags that are used as tools for protein purification that allow purification of virtually any protein without any prior knowledge of its biochemical properties. However for therapeutic applications, the tag typically has to be removed from the fusion protein, e.g., using proteases and a cleavage site. Thus, to the best of our knowledge no effect has been associated with the polyhistidine tag in the MHC II/CII peptide complex as a therapeutic agent for use in treating chronic inflammatory diseases in humans.

4

SUMMARY OF THE INVENTION

The present invention relates to a composition comprising recombinant HLA-DR/CII peptide complexes comprising (a) an extracellular region of an HLA-DR alpha chain comprising at least an alpha 1 domain; (b) an extracellular region of an HLA-DR beta chain comprising at least a beta 1 domain; and (c) a collagen II peptide (CII peptide), optionally fused to the N-terminus of the HLA-DR alpha chain or the HLA-DR beta chain by a linker peptide, preferably to the HLA-DR beta chain; wherein the CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6), AGFKGXQGPXG (SEQ ID NO: 7) and AGFKXEQGPXG (SEQ ID NO: 8), and wherein the HLA-DR/CII peptide complexes comprise a chondroitin-binding peptide at the C-terminal end of the polypeptide comprising the HLA-DR alpha chain and/or the HLA-DR beta chain, for use in treating chronic inflammatory diseases in human patients, particularly chronic inflammatory joint disease and/or arthritis. Preferably the composition for use in treating chronic inflammatory disease is selected from the group consisting of rheumatoid arthritis, osteoarthritis, psoriatic arthritis, non-radiographic axial spondyloarthritis, ankylosing spondylitis, juvenile idiopathic arthritis, relapsing polychondritis, systemic lupus erythematosus, Lyme Meniere diseases, Autoimmune inner ear disease (AIED), or Still's disease.

In certain embodiments the chondroitin-binding peptide is in its free form. This means the recombinant HLA-DR/CII peptide complexes is not multimerized via the chondroitin-binding peptide in the composition and/or the recombinant HLA-DR/CII peptide complexes is not bound to a further molecule via the chondroitin-binding peptide in the composition. The chondroitin-binding peptide may comprise 5 to 20 amino acids, preferably 6 to 12 amino acids. In one embodiment the chondroitin binding peptide is a polyhistidine tag, preferably at least a hexahistidine tag.

In certain embodiments the extracellular region of the HLA-DR alpha chain comprises an alpha 1 and an alpha 2 domain; and/or the extracellular region of the HLA-DR beta chain comprises a beta 1 and a beta 2 domain. In another embodiment or in addition the CII peptide is fused to the N-terminus of the HLA-DR alpha chain or the HLA-DR beta chain by a linker peptide, preferably to the HLA-DR beta chain. In certain embodiments the CII peptide comprises the amino acid sequence of AGFKGEQGPKG (SEQ ID NO: 1), AGFKGEQGPX$_1$G (SEQ ID NO: 2), AGFKGEX$_2$GPKG (SEQ ID NO: 3), AGFKGX$_3$QGPKG (SEQ ID NO: 4), AGFKX$_4$EQGPKG (SEQ ID NO: 5), AGFKGEX$_2$GPX$_1$G (SEQ ID NO: 6), AGFKGX$_3$QGPX$_1$G (SEQ ID NO: 7) and AGFKX$_4$EQGPX$_1$G (SEQ ID NO: 8), wherein X$_1$ is any of the proteinogenic amino acids except K, preferably R, A, G or Q, more preferably R; X$_2$ is any of the proteinogenic amino acids except Q; preferably A, R, H or G; X$_3$ is any of the proteinogenic amino acids except E, preferably A, D, Q or G; and X$_4$ is any of the proteinogenic amino acids except G, more preferably A, S, V or L. Preferably X$_2$, X$_3$ or X$_4$ are not K. In certain embodiments the CII peptide comprises the amino acid sequence of AGFKGEQGPKG (SEQ ID NO: 1) or AGFKGEQGPX$_1$G (SEQ ID NO: 2), preferably of AGFKGEQGPKGEP (SEQ ID NO: 10) or AGFKGEQGPX$_1$GEP (SEQ ID NO: 11), more preferably of GIAGFKGEQGPKGEP (SEQ ID NO: 13) or GIAGFKGEQGPX$_1$GEP (SEQ ID NO: 14).

In the composition for use according to the invention at least the alpha 1 domain is preferably from DRA*0101 and at least the beta 1 domain is from a HLA-DR allele preferably selected from the group consisting of DRB1*0401, DRB1*0404, DRB1*0405, DRB1*0408, DRB1*0409, DRB1*0101, DRB1*0102, DRB1*1001, DRB1*1402 and DRB1*1303, preferably DRB1*0401.

The extracellular region of the HLA-DR alpha chain comprising at least an alpha 1 domain; and the extracellular region of the HLA-DR beta chain comprising at least a beta 1 domain may be expressed as a single fusion polypeptide; and optionally the collagen II peptide (CII peptide) is fused to the N-terminus of the HLA-DR alpha chain or the HLA-DR beta chain by a linker peptide, preferably to the HLA-DR beta chain. Alternatively the alpha and the beta chain may be expressed as separate polynucleotides, wherein the HLA-DR complex comprises a first polypeptide comprises the extracellular region of the HLA-DR alpha chain comprising at least an alpha 1 domain; a second polypeptide comprising the extracellular region of the HLA-DR beta chain comprising at least a beta 1 domain; and the collagen II peptide (CII peptide), optionally fused to the N-terminus of the HLA-DR alpha chain or the HLA-DR beta chain by a linker peptide, preferably to the HLA-DR beta chain; and wherein the HLA-DR alpha chain is fused at its C-terminal end to a first functional domain of a leucine zipper heterodimerization motif and the HLA-DR beta chain is fused at its C-terminal end to a second complementary functional domain of a leucine zipper heterodimerization motif. The first and/or the second functional domain of a leucine zipper heterodimerization motif is/are further followed by the chondroitin-binding peptide. The first functional domain and the second complementary functional domain may be an acidic and a basic leucine zipper heterodimerization domain, preferably a jun-fos leucine zipper motif.

The recombinant HLA-DR/CII peptide complexes comprised in the composition for use according to the invention may comprise CII peptides with unmodified and/or one or more post-translationally modified lysine residue(s). In one embodiment, the CII peptides consist of CII peptides with unmodified lysine residues, the CII peptides consist of CII peptides with the first lysine being hydroxylysine (Hyl), the CII peptides consist of CII peptides with the first lysine being galactosyl-hydroxylysine, or the CII peptides consist of CII peptides with unmodified lysine residues and CII peptides with the first lysine being galactosyl-hydroxylysine. In another embodiment the CII peptides comprise CII peptides with the first lysine being galactosyl-hydroxylysine; the CII peptides comprise CII peptides with unmodified lysine residues and CII peptides with the first lysine being galactosyl-hydroxylysine; the CII peptides comprise CII peptides with unmodified lysine residues and CII peptides with the first lysine being galactosyl-hydroxylysine and/or hydroxylysine (Hyl); or the CII peptides comprise CII peptides with unmodified lysine residues and CII peptides with the first lysine being O-glycosylated hydroxylysine and/or hydroxylysine (Hyl). The optional second lysine in the post-translationally modified CII peptide may be unmodified, hydroxylysine, galactose-hydroxylysine and/or glucosyl-galactosyl-hydroxylysine; preferably unmodified, hydroxylysine, galactose-hydroxylysine, more preferably unmodified. In a preferred embodiment the composition does not contain HLA-DR/CII peptide complexes comprising CII peptides with a glucosyl-galactosyl-hydroxylysine modification.

DESCRIPTION OF THE FIGURES

FIG. 2: IL-2 (FU) secretion of Aq-restricted T cell hybridoma clones in response to Aq/rCII (259-273) complexes (recombinant, in situ glycosylated Aq/rCII) produced in HEK293 cells (top) S2 insect cells (middle) and anti-CD3 antibody stimulation (bottom). The used mouse T cell hybridoma clones have the following specificities: HCQ3 (CII, Gal-HK264), HCQ.4 (CII, not modified and HK264), HCQ. 11 (Glc-Gal-HK264), HM1R.2 (CII, Gal-HK264 and Gal-HK264+270), HP3 (Aq-restricted, pepsin-peptide), wherein K is the abbreviation for lysine and HK is the abbreviation for hydroxylysine.

FIG. 4: Activation of glycosylation restrictive human T cell hybridoma. Human T cell hybridoma cells get activated upon stimulation with the human HLA-DR/CII peptide complex (DR4/hCII) in an antigen-specific manner. Recognition of human T cell hybridoma mDR1.1 and 3H8 is dependent on the glycosylation profile of the CII peptide. A) The T cell hybridoma clone mDR1.1 gets activated by galactosylated K264 presented by HLA-DR4; B) whereas the T cell hybridoma clone 3H8 gets activated by the non-modified CII epitope presented by HLA-DR4. Reactivity of the two different T cell hybridoma clones were compared by using human HLA-DR/CII peptide complexes loaded with synthetic galactosylated or non-modified CII peptide (DR4/galCII and DR4/nCII, respectively) and with naturally glycosylated HLA-DR/CII peptide complex (DR4/hCII). Secretion of IL-2 was measured by ELISA.

FIG. 5: Detection of antigen specific T cells in the peripheral blood of HLA-DRB1*0401 patients with rheumatoid arthritis. A) Biotinylated DR4/galCII peptide complexes were incubated with fluorochrome (PE, APC) conjugated streptavidin. These tetramers were used to detect T cells specific for the CII259-273 peptide with a galactosylation at K264. Antigen specific (CII259-273, K264 gal) T cells in PBMCs of RA patients and healthy donors were detected using flow cytometry. B) Comparison of frequency of antigen specific T cells using DR4/galCII peptide tetramers, DR4/nCII peptide tetramers or DR4/hCII peptide tetramers for detection. The frequency of tetramer positive T cells within the CD4$^+$ T cell population was measured by flow cytometry.

FIG. 7: Legendplex™ analysis of cytokine release by PBMCs from HLA-DRB1*0401 positive RA patients (n=20) stimulated in vitro. Shown is the specific induction of IL-2, IL-17f, IFN-γIL-10, IL-17a and, TNF-αrelease by in vitro stimulation with DR4/nCII peptide complex or DR4/galCII peptide complex in comparison to stimulation with standard TR1 cell differentiating conditions (TR1) and negative control (CO).

FIG. 8: Comparison of complexes with and without His-tag. (A) ELISA comparing the coating efficacy of microtiter wells by equimolar solutions of DR4/nCII vs. DR4/nCII Tev-cleaved complexes using a DR4-specific antibody and a peroxidase-coupled secondary antibody. Shown is the absorption at 405 nm at the indicated protein concentration of the DR4/nCII solutions used for coating to the microtiter plates [μg/ml]. (B) Activation of 3H8 hybridoma cells by DR4/nCII vs. DR4/nCII Tev-cleaved complexes pre-coated to microtiter wells at the indicated concentrations. Shown are IL-2 concentrations in the supernatant following activation at the indicated protein concentration of the DR4/nCII solutions used for coating to the microtiter plates [μg/ml].

FIG. 13: Heterogeneity in the post-translational modification of the CII-peptide in the recombinant DR4/hCII complex. The percentage of detectable modifications at the respective position at the indicated K position as analysed by mass spectrometric analysis is shown. [OH=hydroxylysine, Hex=galactosyl-hydroxylysine, DiHex=glucosyl-galactosyl-hydroxylysine, Ub=ubiquitine, POH=hydroxyproline.

FIG. 15: Aq/gal264 CII constructs with alternative positively charged amino acid tags at the C-terminus of the sequence containing the β-chain. A) Sequences of H2AN tag (N-terminal H2A sequence; Histone NT; SEQ ID NO: 34), H2AC tag (C-terminal H2A sequence; Histone CT; SEQ ID NO: 40) and NH tag (modified His; SEQ ID NO: 35) are shown. B) Sequence alignment of human and mouse histone H2A is shown. Matches are indicated by (*) and mismatches are indicated by (:). The boxes indicate the position of the histone NT and CT sequence.

DETAILED DESCRIPTION OF PREFERRED EMBODIMENTS

Figure 1:
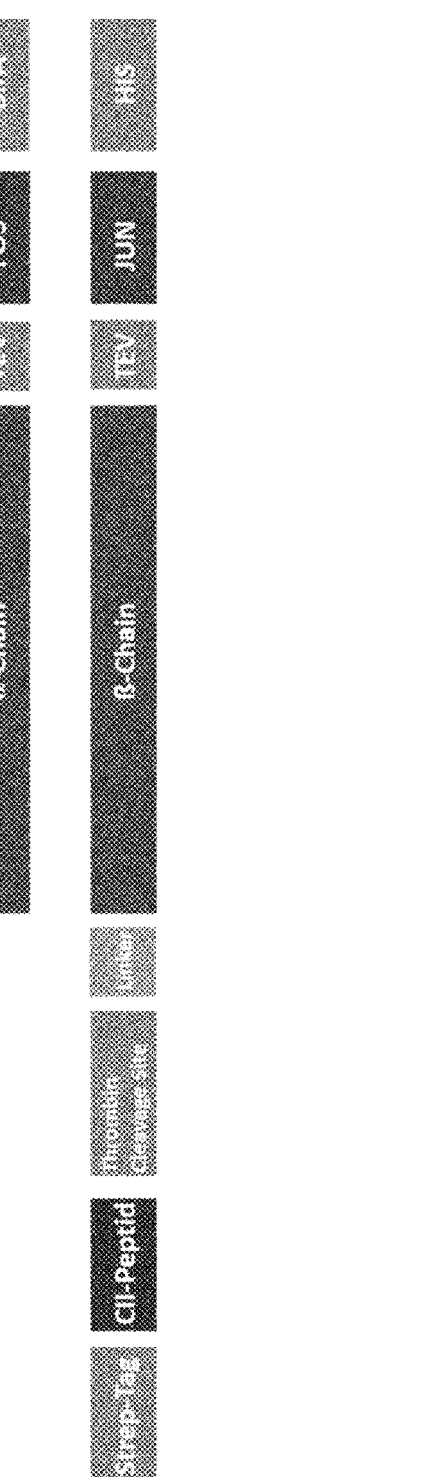
FIG. 1: Schematic drawing of an HLA-DR/CII peptide complex. MHC II molecule with a covalently bound CII259-273 peptide. BirA: biotinylation site, HIS: poly (6×) histidine tag, JUN/FOS: complementary domains of a leucine zipper (heterodimerization domain), TEV: Tobacco Etch Virus (TEV) cysteine protease cleavage site, Linker: Gly-Ser linker peptide, thrombin cleavage site, strep-tag, CII peptide 259-273.

The general embodiments "comprising of" or "comprised of" encompass the more specific embodiment "consisting of". Furthermore, singular and plural forms are not used in a limiting way. As used herein, the singular forms "a", "an"

and "the" designate both the singular and the plural, unless expressly stated to designate the singular only.

The term "protein" is used interchangeably with "amino acid sequence" or "polypeptide" and refers to polymers of amino acids of any length. These terms also include proteins that are post-translationally modified through reactions that include, but are not limited to, glycosylation, acetylation, phosphorylation, glycation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with the same properties.

The term "polypeptide" typically refers to a sequence of more than 20amino acids and the term "peptide" means sequences with up to 20 amino acids in length. However, the terms may be used interchangeably. A protein may form multimers such as dimers, wherein the dimer may be a heterodimer or a homodimer. The HLA-DR/CII peptide complex according to the invention comprise an extracellular region of an MHC class II alpha chain and an extracellular region of an MHC class II beta chain, which typically form a heterodimer which forms the binding groove to harbor the collagen II peptide fused to the N-terminus of one of the chains. However, the person skilled in the art will understand that two proteins forming a heterodimer can also be generated as a fusion protein forming a single polypeptide chain with the domains linked to each other, optionally via a flexible linker, i.e. a single chain heterodimer.

A "fusion protein" is defined as a protein which contains the complete sequences or any parts of the sequences of two or more originally separate natural or modified proteins. Fusion proteins can be constructed by genetic engineering approaches using recombinant DNA techniques by fusing the two or more genes or cDNAs, or parts thereof, that originally encode the two or more originally separate natural or heterologous proteins, or parts thereof. This results in a fusion protein with functional properties derived from each of the original proteins. Thus, a peptide or protein is linked to another protein by a peptide bond or preferably a linker peptide.

The term "genomic DNA", or "genome" is used interchangeably and refers to the heritable genetic information of a host organism. The genomic DNA comprises the DNA of the nucleus (also referred to as chromosomal DNA) but also of other cellular organelles (e.g., mitochondria).

The term "gene" as used herein refers to a DNA locus of heritable genomic sequence which affects an organism's traits by being expressed as a functional product or by regulation of gene expression. Genes and polynucleotides may include introns and exons as in a genomic sequence, or just the coding sequences as comprised in a cDNA, such as an open reading frame (ORF), comprising a start codon (methionine codon) and a translation stop codon. Genes and polynucleotides can also include regions that regulate their expression, such as transcription initiation, translation and transcription termination. Thus, also included are regulatory elements such as a promoter.

The terms "nucleic acid", "nucleotide", and "polynucleotide" as used herein are used interchangeably and refer to a single or double-stranded polymer of deoxyribonucleotide bases or ribonucleotide bases read from the 5' to the 3' end and include double stranded DNA (dsDNA), single stranded DNA (ssDNA), single stranded RNA (ssRNA), double stranded RNA (dsRNA), genomic DNA, cDNA, CRNA, recombinant DNA or recombinant RNA and derivatives thereof, such as those containing modified backbones. Preferably, a polynucleotide, particularly to be stably integrated into the mammalian genome, is a DNA or cDNA. Polynucleotides according to the invention can be prepared in different ways (e.g. by chemical synthesis, by gene cloning etc.) and can take various forms (e.g. linear or branched, single or double stranded, or a hybrid thereof, primers, probes etc.). The term "nucleotide sequence" or "nucleic acid sequence" refers to both the sense and antisense strands of a nucleic acid as either individual single strands or in the duplex.

The term "recombinant polynucleotide" as used herein refers to a polynucleotide derived from a different cell, organism or a different species from the recipient, e.g., a CHO cell or a HEK 293 cell, and introduced into the recipient using recombinant techniques. In the context of the present invention the skilled person would understand that it refers to a DNA or cDNA. A recombinant polynucleotide may also be referred to as transgene or a heterologous polynucleotide. Thus, it may be a gene or an open reading frame (ORF) coding for a recombinant protein. In the context of mammalian cells, such as HEK 293 or CHO cells "recombinant polynucleotide" refers to a polynucleotide derived from a different cell or artificially synthesized. The term "recombinant" refers to molecules such as polypeptides or polynucleic acid molecules formed by laboratory method of genetic recombination, such as molecular cloning. Such methods bring together genetic material from multiple sources or create sequences that do not naturally exist. When used with reference to portions of a nucleic acid, "recombinant" also includes a polynucleotide comprising two or more sequences that are not found in the same relationship to each other in nature or a polypeptide encoded by said polynucleotide. Recombinant may therefore also refer to a polynucleotide sequence, such as a gene or transgene, or a portion thereof, derived from the same cell line, but being inserted into the genome in a location in which it is not typically found, or a gene introduced into a cell of an organism in which it is not typically found.

As used herein a "recombinant polynucleotide", "recombinant gene" or "recombinant sequences" can be introduced into a target cell or host cell directly or preferably by using an "expression vector", preferably a mammalian expression vector. Methods used to construct vectors are well known to the person skilled in the art. Vectors may include, but are not limited to, plasmid vectors, cosmids, artificial/mini-chromosomes (e.g. ACE), or viral vectors such as retrovirus, adenovirus, adeno-associated virus and herpes simplex virus. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operably linked, are well known in the art. Usually expression vectors also comprise an expression cassette encoding a selectable marker, allowing selection of host cells carrying said expression marker.

The term "cytokine" refers to small proteins, which are released by cells and act as intercellular mediators, for example influencing the behavior of the cells surrounding the secreting cell. Cytokines may be secreted by immune or other cells, such as T-cells, B-cells, NK cells and macrophages. Cytokines may be involved in intercellular signaling events, such as autocrine signaling, paracrine signaling and endocrine signaling. They may mediate a range of biological processes including, but not limited to immunity, inflammation, and hematopoiesis. Cytokines may be chemokines, interferons, interleukins, lymphokines or tumor necrosis factors.

The term "expression" as used herein refers to transcription and/or translation of a nucleic acid sequence within a host cell. The level of expression of a gene product of interest in a host cell may be determined on the basis of either the amount of corresponding RNA that is present in the cell, or the amount of the polypeptide encoded by the selected sequence. For example, RNA transcribed from a selected sequence can be quantified by Northern blot hybridization, ribonuclease RNA protection, in situ hybridization to cellular RNA or by PCR, such as qPCR. Proteins encoded by a selected sequence can be quantitated by various methods, e.g. by ELISA, by Western blotting, by radioimmunoassay, by immunoprecipitation, by assaying for the biological activity of the protein, by immunostaining of the protein followed by FACS analysis or by homogeneous time-resolved fluorescence (HTRF) assays. The level of expression of a non-coding RNA, such as a miRNA or shRNA may be quantified by PCR, such as qPCR.

The term "gene product" refers to both the RNA polynucleotide and polypeptide that is encoded by a gene or DNA polynucleotide.

The term "proteinogenic amino acid" as used herein refers to all amino acids that are incorporated biosynthetically into proteins during translation. The term "proteinogenic" means protein creating. In eukaryotes there are 21 genetically encoding amino acids, i.e., proteinogenic amino acids, the 20 of the standard genetic code and selenocysteine. The 20 amino acids of the standard genetic code are alanine, arginine, asparagine, aspartic acid, cysteine, glutamic acid, glutamine, glycine, histidine, isoleucine, leucine, lysine, methionine, phenylalanine, proline, serine, threonine, tryptophane, tyrosine and valine.

The term "post-translational modification" or "post-translationally modified" as used herein refers to a naturally occurring modification of a lysine residue in the CII peptide that may occur when produced in cells. The post-translational modification of a lysine residue may result in hydroxylysine (Hyl) or is O-glycosylated Hyl, such as galactosyl-hydroxylysine or glucosylgalactosyl-hydroxylysine, preferably galactosyl-hydroxylysine.

The term "domain" as used herein refers to a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. For example, the alpha 1 domain of the MHC II alpha chain and the beta 1 domain of the MHC II beta chain each are folded polypeptide domains together forming the peptide binding groove of the MHC II molecule.

The Composition Comprising a Recombinant HLA-DR/CII Peptide Complex Comprising a Chondroitin-Binding Peptide for Use in Treating Chronic Inflammatory Disease is Humans In one aspect the invention provides a composition comprising recombinant HLA-DR/CII peptide complexes comprising an extracellular region of an HLA-DR alpha chain comprising at least an alpha 1 domain; an extracellular region of an HLA-DR beta chain comprising at least a beta 1 domain; and a collagen II peptide (CII peptide), optionally fused to the N-terminus of the HLA-DR alpha chain or the HLA-DR beta chain by a linker peptide, preferably to the HLA-DR beta chain; wherein the CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6), AGFKGXQGPXG (SEQ ID NO: 7) and AGFKXEQGPXG (SEQ ID NO: 8), and wherein the HLA-DR/CII peptide complexes comprise a chondroitin-binding peptide at the C-terminal end of the polypeptide comprising the HLA-DR alpha chain and/or the HLA-DR beta chain, for use in treating chronic inflammatory diseases in human patients. In one embodiment the CII peptide is fused to the N-terminus of the HLA-DR alpha chain or the HLA-DR beta chain by a linker peptide. In one embodiment the CII peptide is fused to the N-terminus of the HLA-DR beta chain.

In one embodiment, the chondroitin-binding peptide mediates binding of the recombinant HLA-DR/CII peptide complex to chondroitin in vivo. Without being bound by theory, the chondroitin-binding peptide may mediate binding of the recombinant HLA-DR/CII peptide complex to chondroitin in cartilage, preferably joint cartilage. Alternatively, or in addition, the chondroitin-binding peptide may mediate binding of the recombinant HLA-DR/CII peptide complex to negatively charged carbohydrates, such as chondroitin or chondroitin-like structures, on cell surfaces on immune cells, particularly T cells and/or in the matrix of lymph nodes or other tissues like synovia. Charged glycosaminoglycans are released into the synovial fluid at high concentrations from either the cartilage matrix and/or the synovial lining cells during an active immune-mediated chronic arthritis in the joint (approximately 4 mg/100 ml; Seppälä P O et al. Clin Chim Acta 1975; 36:549-553).

It was surprisingly shown that the His-tag in HLA-DR/CII peptide complexes added to the C-terminal end of the polypeptide chain comprising one of the HLA-DR beta chains as shown in FIG. 1 and C-terminal of the heterodimerization domain improves the effect of the HLA-DR/CII peptide complex in vitro. It was further surprisingly found that the His-tag facilitates binding of the recombinant HLA-DR/CII peptide complex to the extracellular matrix component chondroitin and that in microtiter plates coated with chondroitin sulfate only His-tagged complexes were able to induce a sufficient IL-2 response in T cell hybridomas in soluble form. Without being bound by theory, binding of recombinant HLA-DR/CII peptide complex to the extracellular matrix component chondroitin sulfate may lead to an improved spatial orientation and/or multimerization, resulting in improved presentation of the peptide binding group for TCR recognition. This observation has been confirmed by in vivo data demonstrating reduced swelling in a CII induced delayed type hypersensitivity (DTH) model following administration of the His-tagged complex compared to the complex without His-tag. Thus, without being bound by theory, the His-tag may be important for the binding of the recombinant HLA-DR/CII peptide complex to the TCR by increased avidity due to interaction with negatively charged molecules on cell surfaces or tissue surfaces, such as chondroitin, leading to multimerization of the complexes and/or correct orientation, facilitating interaction of the complex with the TCR. In addition, the chondroitin interaction might also help to engage costimulatory molecules on the T cell membrane that can either bind to chondroitin and/or contain a chondroitin moiety itself e.g. CD44 or CD74, protein tyrosine phosphatase PTPσ.

Chondroitin, also referred to as chondroitin sulfate herein, is a sulfated glycosaminoglycan (GAG) composed of a chain of alternating sugars, N-acetylgalactosamine and glucuronic acid. It is often found attached to proteins as part of a proteoglycan. Proteoglycans are a major component of the extracellular matrix (ECM). Chondroitin sulfate is also an important structural component of cartilage. It is further present in extracellular body fluids such as synovial effusions or the lymph as well as in tissues, such as joint cartilage or synovial membranes. Thus, the His-tag may support localization to joint structures, the site in the body mostly affected during arthritis, or lymph nodes and hence mediate an advantageous distribution of the complex in vivo. The person skilled in the art will understand that this ability is not limited to a polyhistidine tag, such as a hexahistidine tag or preferably a heptahistidine tag, but can be mediated by any chondroitin binding peptide.

Thus, the composition for use according to the present invention comprises HLA-DR/CII peptide complexes containing at least one chondroitin-binding peptide, preferably a chondroitin- and hyaluronic acid (also referred to as hyaluronan) binding peptide. Preferably the chondroitin-binding peptide is located at the C-terminal end of at least one polypeptide chain of the complex. In one embodiment the HLA-DR/CII peptide complex comprises at least one C-terminal chondroitin-binding peptide. Chondroitin-binding peptides are known in the art and include without being limited thereto peptides having the amino acid sequences EKRIWFPYRRF (SEQ ID NO: 31), YKTNFRRYYRF (SEQ ID NO: 32) or VLIRHFRKRYY (SEQ ID NO: 33) (Butterfield K C et al., Biochemistry. 2010 Feb. 23; 49(7): 1549-55). In one embodiment the chondroitin binding peptide comprises 5 to 20 amino acids, preferably 6 to 20 amino acids, preferably 6 to 12 amino acids, more preferably 6 to 12, even more preferably 6 to 12 amino acids. Also positively charged histone peptides have been identified herein, particularly peptides of human H2A histone such as a peptide comprising the amino acid sequence SGRGKQGGKARAKAKTRSSR (SEQ ID NO: 34). The term chondroitin and chondroitin sulfate are used interchangeably herein and hence the chondroitin-binding peptide may also be referred to as chondroitin sulfate binding peptide. To increase binding to hyaluronan an exemplary sequence containing the binding consensus motif is defined as follows: B(X7) B, in which B is either R or K and X7 contains no acidic residues and at least one basic amino acid (Yang B et al., EMBO J. 1994 Jan. 15; 13(2): 286-96). As disclosed herein the HLA-DR/CII peptide complex can also bind to chondroitin sulfate via the his-tag. Thus, the con-droitin-binding peptide may be a polyhistidine tag, preferably a hexahistidine tag, or any other amino acid sequences that increase binding affinity to chondroitin, such as EKRIWFPYRRF (SEQ ID NO: 31), YKTNFRRYYRF (SEQ ID NO: 32) or VLIRHFRKRYY (SEQ ID NO: 33). The term His-tag is used synonymously with polyhistidine-tag herein and refers to a tag having at least 6 consecutive histidine residues (at least a hexahistidine-tag). Preferably the His-tag is at least a heptahistidine-tag.

In one embodiment (a) the C-terminal chondroitin-binding peptide is in its free form; (b) the recombinant HLA-DR/CII peptide complexes is not multimerized via the chondroitin-binding peptide in the composition; (c) the recombinant HLA-DR/CII peptide complexes is not bound to a further molecule via the chondroitin-binding peptide in the composition; or a combination of any of (a), (b) or (c). Thus, the chondroitin-binding peptide is free to bind in vivo to chondroitin.

The term "HLA-DR/CII peptide complex" refers to a soluble complex comprising the extracellular domains of a human MHC II protein (HLA-DR isotype) or part thereof forming the peptide binding groove and a collagen II peptide (CII peptide), wherein the peptide is optionally fused (i.e., linked) to the N-terminus of either the alpha or the beta chain. Preferably the CII peptide is fused to the N-terminus of either the alpha or the beta chain and more preferably to the N-terminus of the MHC class II beta chain. Alternatively the HLA-DR protein may be produced with a surrogate peptide, such as the class II-associated invariant chain peptide (CLIP), fused to the N-terminus of the extracellular part of the beta chain or the alpha chain, preferably the beta chain, by a linker peptide comprising a protease cleavage site (e.g., a thrombin cleavage site); cleaving off CLIP using a protease (e.g., thrombin) recognizing said protease cleavage site; and loading the HLA-DR protein with the post-translationally modified or unmodified CII peptide to form the HLA-DR/CII peptide complex. A HLA-DR protein comprises an alpha 1 domain and an alpha 2 domain, which form the extracellular domain of the alpha chain and a beta 1 domain and a beta 2 domain, which form the extracellular domain of the beta chain. The term "extracellular domain" and "extracellular region" are used synonymously herein. The alpha 1 domain and the beta 1 domain form the peptide binding groove, i.e., the site that interacts and binds the peptide, such as a CII peptide. Thus, the HLA-DR/CII peptide complex comprises at least the alpha 1 domain and the beta 1 domain of the HLA-DR protein. Preferably the HLA-DR/CII peptide complex comprises the alpha 1 domain, the alpha 2 domain, the beta 1 domain and the beta 2 domain of the HLA-DR protein.

For RA in humans there is a genetic association with certain alleles of the HLA-DRB1 locus coding for an amino acid consensus motif (Q/R R/K R A A) on the beta-chain of the peptide binding pocket of the MHC class II molecule HLA-DR (amino acid position 70-74, the so called "shared epitope"). Examples for RA associates HLA DRB1 alleles are QKRAA-coding alleles HLA_DRB1* 0401 and 0409, QRRAA-coding alleles: HLA_DRB1* 0404, 0405, 0408, 0101, 0102 and 1402, RRRAA-coding allele: HLA_DRB1* 1001 and DKRAA-coding allele: HLA_DRB1* 1303. The extracellular region of the MHC class II alpha chain and the extracellular region of the MHC class II beta chain are therefore derived from HLA-DR, preferably at least the alpha 1 domain is from DRA*0101 and at least the beta 1 domain is from a HLA-DR allele selected from the group consisting of DRB1*0401, DRB1*0404, DRB1*0405, DRB1*0408, DRB1*0409, DRB1*0101, DRB1*0102, DRB1*1001, DRB1*1402 and DRB1*1303, preferably DRB1*0401, DRB1*0404, DRB1*0405, DRB1*0408, DRB1*0409, DRB1*0101, DRB1*0102, DRB1*1001 and DRB1*1402, more preferably DRB1*0401, DRB1*0404 and DRB1*0405. More preferably the alpha 1 domain and the alpha 2 domain is from DRA*0101 and the beta 1 domain and the beta 2 domain is from a HLA-DR allele selected from the group consisting of DRB1*0401, DRB1*0404, DRB1*0405, DRB1*0408, DRB1*0409, DRB1*0101, DRB1*0102, DRB1*1001, DRB1*1402 and DRB1*1303, preferably DRB1*0401, DRB1*0404, DRB1*0405, DRB1*0408, DRB1*0409, DRB1*0101, DRB1*0102, DRB1*1001 and DRB1*1402, more preferably DRB1*0401, DRB1*0404 and DRB1*0405.

The recombinant HLA-DR/CII peptide complexes in the composition for use according the invention comprise unmodified CII peptides and/or post-translationally modified CII peptides, more specifically CII peptides with unmodified or one or more post-translationally modified lysine(s), preferably with the first lysine being post-translationally modified. The term "post-translational modified" or "post-translational modified CII peptides" as used herein refers to CII peptides carrying a modification to the first and optionally second lysine residue selected from hydroxylysine (Hyl), galactosyl-hydroxylysine or glucosyl-galactosyl-hydroxylysine, i.e., a modification obtainable by post-translational modification of lysine residues in collagen in cells. Thus, it does not require that the modification is obtained by post-translational modification, i.e., in cells, but may likewise be obtained by enzymatic or synthetic means in vitro.

Post-translationally modified CII peptides comprise CII peptides wherein at least one lysine residue of the CII peptide is hydroxylysine (Hyl) and/or is O-glycosylated Hyl. Preferably the first lysine residue of the CII peptide is hydroxylysine (Hyl) and/or is O-glycosylated Hyl. The HLA-DR/CII peptide complexes in the composition may comprise the same CII peptides. Thus, in one embodiment, the CII peptides consist of CII peptides with unmodified lysine residues; or the CII peptides consist of CII peptides with the first lysine being hydroxylysine (Hyl); or the CII peptides consist of CII peptides with the first lysine being galactosyl-hydroxylysine. The HLA-DR/CII peptide complexes in the composition may also comprise a mixture of CII peptides. This may be achieved by loading the HLA-DR protein with a mixture of unmodified CII peptides and post-translationally modified CII peptides, or by loading the HLA-DR complex with unmodified or post-translationally modified CII peptides and mixing the HLA-DR/CII peptide complexes thereafter. The skilled person will understand that the post-translationally modified CII peptides will typically be generated in vitro either synthetically or enzymatically. Alternatively, this may be achieved by preparing the HLA-DR/CII peptide complexes with the CII peptide fused to the N-terminus of the HLA-DR alpha chain or the HLA-DR beta chain by a linker peptide in vivo using a cell line capable of adding post-translational modifications to lysine residues in collagen. Thus, in another embodiment the CII peptides consist of CII peptides with unmodified lysine residues and CII peptides with the first lysine being galactosyl-hydroxylysine; the CII peptides comprise CII peptides with the first lysine being galactosyl-hydroxylysine; the CII peptides comprise CII peptides with unmodified lysine residues and CII peptides with the first lysine being galactosyl-hydroxylysine; the CII peptides comprise CII peptides with unmodified lysine residues and CII peptides with the first lysine being galactosyl-hydroxylysine and/or hydroxylysine (Hyl); or the CII peptides comprise CII peptides with unmodified lysine residues and CII peptides with the first lysine being O-glycosylated hydroxylysine and/or hydroxylysine (Hyl). In this embodiments the optional second lysine in the post-translationally modified CII peptide may be unmodified, hydroxylysine, and/or O-glycosylated hydroxylysine; more specifically unmodified, hydroxylysine, galactose-hydroxylysine and/or glucosyl-galactosyl-hydroxylysine; preferably unmodified, hydroxylysine, galactose-hydroxylysine, more preferably unmodified. In one embodiment the optional second lysine in the CII peptide or post-translationally modified CII peptide is not glucosyl-galactosyl-hydroxylysine. In one embodiment the composition does not contain HLA-DR/CII peptide complexes comprising CII peptides with a glucosyl-galactosyl-hydroxylysine modification, i.e., not at the first or the optional second lysine.

The CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6), AGFKGXQGPXG (SEQ ID NO: 7) and AGFKXEQGPXG (SEQ ID NO: 8). In certain embodiments the CII peptide comprises the amino acid sequence of AGFKGEQGPKG (SEQ ID NO: 1), AGFKGEQGPX$_1$G (SEQ ID NO: 2), AGFKGEX$_2$GPKG (SEQ ID NO: 3), AGFKGX$_3$QGPKG (SEQ ID NO: 4), AGFKX$_4$EQGPKG (SEQ ID NO: 5), AGFKGEX$_2$GPX$_1$G (SEQ ID NO: 6) and AGFKGX$_3$QGPX$_1$G (SEQ ID NO: 7), AGFKX$_4$EQGPX$_1$G (SEQ ID NO: 8), wherein X$_1$ is any of the proteinogenic amino acids except K, preferably R, A, G or Q, more preferably R; X$_2$ is any of the proteinogenic amino acids except Q; preferably A, R, H or G; X$_3$ is any of the proteinogenic amino acids except E, preferably A, D, Q or G; and X$_4$ is any of the proteinogenic amino acids except G, more preferably A, S, V or L. Preferably X$_2$, X$_3$ or X$_4$ is not K. In certain embodiments the CII peptide comprises the amino acid sequence of AGFKGEQGPKG (SEQ ID NO: 1) or AGFKGEQGPX$_1$G (SEQ ID NO: 2), preferably of AGFKGEQGPKGEP (SEQ ID NO: 10) or AGFKGEQGPX$_1$GEP (SEQ ID NO: 11), more preferably of GIAGFKGEQGPKGEP (SEQ ID NO: 13) or GIAGFKGEQGPX$_1$GEP (SEQ ID NO: 14). The CII peptide GIAGFKGEQGPKGEP (SEQ ID NO: 13) corresponds to amino acids 259-273 of the triple helical CII region. CII peptides suitable for binding into the binding pocket of HLA-DR are from 10 to 20 amino acids in length, preferably the CII peptide is from 11 to 15 amino acids in length, more preferably the CII peptide is from 13 to 15 amino acids in length. In one embodiment the CII peptide comprises the amino acid sequence AGFKGEQGPKG (SEQ ID NO: 1), more preferably AGFKGEQGPKGEP (SEQ ID NO: 10) and even more preferably of GIAGFKGEQGPKGEP (SEQ ID NO: 13). Alternatively, the CII peptide may comprise 11, preferably 12, more preferably 13 and most preferably 15 consecutive amino acids of GIAGFKGEQGPKGEP (SEQ ID NO: 13). In one embodiment the second K (K270) may be mutated, preferably to R. Thus, also encompassed are embodiments, wherein the CII peptide comprises the amino acid sequence AGFKGEQGPXG (SEQ ID NO: 2), AGFKGEQGPXGEP (SEQ ID NO: 11) and GIAGFKGEQGPXGEP (SEQ ID NO: 14), wherein X may be any proteinogenic amino acid other than K, preferably X is R, A, G or Q, more preferably X is R. Thus, in one embodiment the CII peptide comprises the amino acid sequence AGFKGEQGPRG (SEQ ID NO: 9), AGFKGEQGPRGEP (SEQ ID NO: 12) and GIAGFKGEQGPRGEP (SEQ ID NO: 15). CII peptides encompassed by the present invention are disclosed in Table 1:

TABLE 1

| Sequence | SEQ ID NO: |
|---|---|
| AGFKGEQGPKG | SEQ ID NO: 1 |
| AGFKGEQGPX$_1$G* | SEQ ID NO: 2 |
| AGFKGEX$_2$GPKG* | SEQ ID NO: 3 |
| AGFKGX$_3$QGPKG* | SEQ ID NO: 4 |
| AGFKX$_4$EQGPKG* | SEQ ID NO: 5 |
| AGFKGEX$_2$GPX$_1$G* | SEQ ID NO: 6 |
| AGFKGX$_3$QGPX$_1$G* | SEQ ID NO: 7 |
| AGFKX$_4$EQGPX$_1$G* | SEQ ID NO: 8 |

TABLE 1-continued

| Sequence | SEQ ID NO: |
|---|---|
| AGFKGEQGPRG | SEQ ID NO: 9 |
| AGFKGEQGPKGEP | SEQ ID NO: 10 |
| AGFKGEQGP$X_1$GEP* | SEQ ID NO: 11 |
| AGFKGEQGPRGEP | SEQ ID NO: 12 |
| GIAGFKGEQGPKGEP | SEQ ID NO: 13 |
| GIAGFKGEQGP$X_1$GEP* | SEQ ID NO: 14 |
| GIAGFKGEQGPRGEP | SEQ ID NO: 15 |

*wherein $X_1$ is any of the proteinogenic amino acids except K, preferably R, A, G or Q, morepreferably R; $X_2$ is any of the proteinogenic amino acids except Q; preferably A, R, H or G; $X_3$ is any of the proteinogenic amino acids except E, preferably A, D, Q or G; and $X_4$ is any of the proteinogenic amino acids except G, more preferably A, S, V or L.

The HLA-DR/CII peptide complexes in the composition for use according the invention comprise unmodified CII peptides and/or post-translationally modified CII peptides. Post-translationally modified CII peptides comprise CII peptides wherein at least the first lysine residue of the CII peptide is hydroxylysine (Hyl) and/or is O-glycosylated Hyl. Preferably, hydroxylysine (Hyl) and/or galactosyl-hydroxylysine, more preferably galactosyl-hydroxylysine. The first lysine (K) residue of the CII peptide corresponds to the first K in GIAGF<u>K</u>GEQGPKGEP (SEQ ID NO: 13) at position 264 of the amino acid sequence of the triple helical CII region (corresponding to amino acid position 4 in SEQ ID NOs: 1 to 12 and amino acid position 6 in SEQ ID NOs: 13-15). Thus, the "first lysine residue" as used herein may also be referred to as K264 or lysine at position 264. The optional second lysine (K) residue in the CII peptide corresponds to the second K in GIAGFKGEQGP<u>K</u>GEP (SEQ ID NO: 13) at position 270 of the amino acid sequence of the triple helical CII region (corresponding to amino acid position 10 in SEQ ID NOs: 1, 3-5 or 10, and amino acid position 12 in SEQ ID NO: 13). Thus, the "second lysine residue" or "further lysine residue" as used herein may also be referred to as K270 or lysine at position 270. The HLA-DR/CII peptide complexes in the composition for use may be a mixture of complexes comprising unmodified CII peptides and post-translationally modified CII peptides (Hyl, gal-Hyl and glc-gal-Hyl, preferably Hyl and gal-Hyl, more preferably gal-Hyl), i.e., comprising different CII peptides with and without post-translational modifications", or may consist of HLA-DR/CII peptide complexes having an unmodified CII peptide or having a post-translationally modified CII peptide with either having a Hyl or a gal-Hyl modification, preferably a gal-Hyl modification, i.e., comprising the same CII peptide with or without a post-translational modification. In a preferred embodiment the HLA-DR/CII peptide complexes in the composition for use according to the invention comprise unmodified CII peptides and post-translationally modified CII peptides, wherein at least the first lysine residue is hydroxylysine and/or galactosyl-hydroxylysine. The term "galactosyl-hydroxylysine" may also be referred to as G-Hyl or Gal-Hyl and excludes a modification to glucosylgalactosyl-hydroxylysine.

The collagen specific post-translational galactosylation of the lysine residues in the CII peptide sequence according to the invention, particularly of the first lysine residue, i.e., lysine residue at position 264, may be involved in T cell recognition via the TCR and the resulting pharmacological effects. The lysine residue in position 270 is located at the edge of the binding groove of the DR4 molecule and its galactosyl-hydroxylysine modification is considered to be less important for TCR recognition. Thus, the second or further lysine residue (corresponding to K 270) may be any of unmodified, hydroxylysine or galactosyl-hydroxylysine, preferably unmodified. It has been shown that the TCR of a T cell hybridoma recognizing the gal264 epitope is not affected by a K270R mutation. In a preferred embodiment, particularly when the complexes are produced in vivo in cell lines capable of post-translationally modifying lysine residues in collagen, the CII peptide comprises only the first lysine residue and any further optional K (such as the optional second K) is mutated, preferably mutated to R, A, G or Q, more preferably mutated to R. Therefore CII peptides comprising the amino acid sequence AGFKGEQGPRG (SEQ ID NO: 9), preferably AGFKGEQGPRGEP (SEQ ID NO: 12) and more preferably GIAGFKGEQGPRGEP (SEQ ID NO: 15) are also encompassed by the present invention. Mutation of the second lysine has the advantage to reduce heterogeneity of the product and hence the percentage of correctly modified peptides is higher. Furthermore, galactosyl-hydroxylysine may be glucosylated to form glucosyl-galactosyl-hydoxylysine (Glc-Gal-Hyl, or GG-Hyl) in vivo in host production cells, which is likely to have a negative effect on TCR recognition due to the bulkiness of the disaccharide (Glc-Gal), particularly at position K270. Thus a K270 mutation, particularly K270R, further avoids interference with binding as no disaccharide modification can be attached at this position.

In one embodiment, the collagen II peptide (CII peptide) is fused to the N-terminus of the HLA-DR alpha chain or the HLA-DR beta chain by a linker peptide, preferably to the N-terminus of the MHC class II beta chain. This allows production of the entire complex including respective post-translational modifications of the CII peptide in a host production cell. The term "linker peptide" refers to a polypeptide consisting of multiple amino acid residues. The linker peptide may be any peptide as long as it is long and flexible enough to allow the peptide to bind to the peptide binding pocket formed by the MHC II complex. An example of a suitable linker peptide is a Gly-Ser linker. According to the invention the CII peptide, the linker peptide and at least one of the extracellular regions of the MHC II alpha chain and the MHC II beta chain are expressed as one polypeptide and encoded by one polynucleotide. The term "fused to" as used herein means "linked to" wherein the linking is via peptide bonds, optionally using a linker peptide, and therefore a fusion protein is generated. Alternatively the HLA-DR protein is produced with a surrogate peptide, such as a CLIP peptide, which is linked to one of the HLA-DR chains via a linker peptide comprising a protease cleavage site, such as a thrombin cleavage site. Thus, following production the peptide is proteolytically cleaved off and the unmodified or galactosylated CII peptide (i.e., a CII peptide carrying gal-Hyl at position K264), typically prepared synthetically or enzymatically in vitro, is loaded in vitro onto the complex. Thus, in an alternative embodiment the unmodified and/or post-translationally modified CII peptide is loaded onto the HLA-DR protein to form the HLA-DR/CII peptide complex. Although this synthetic unmodified or galactosylated peptide may be covalently linked to the HLA-DR molecule, this linkage is not via a linker peptide. In this context post-translationally modified relates to modifications of at least one lysine residue in the CII peptide to Hyl, gal-Hyl or glc-gal-Hyl, wherein the modification may be added in vivo to the HLA-DR/CII peptide complex within in the host production cell capable of post-translationally modifying lysine residues in collagen, or synthetically or enzymatically in vitro to the CII peptide that is loaded onto the HLA-DR protein.

While the HLA-DR/CII peptide complex used in the examples (SEQ ID NO: 16 and SEQ ID NO: 17) and as depicted in FIG. 1 without the signal peptide comprising the CII peptide fused to the N-terminus of the HLA-DR beta chain still contains an enzymatic cleavage site (thrombin cleavage site, FIG. 1) between the linker and the CII peptide, this is not necessary and is preferably removed from a therapeutic product. The linker peptide may improve stability of the product and prevent peptide loss. Thus, preferably the HLA-DR/CII peptide complex according to the invention does not contain an enzymatic (proteolytic) cleavage site in the amino acid sequence between the CII peptide and extracellular region of the HLA-DR beta chain (or the HLA-DR alpha chain). Furthermore, for therapeutic purposes the HLA-DR/CII peptide complexes comprised in the composition do not comprise a (1) streptavidin-tag (SAWSHPQFEK, SEQ ID NO: 30) for purification, (2) a cleavage site (e.g., a TEV cleavage site) between the HLA-DRα/HLA-DR B chain and the heterodimerisation domain and/or (3) a recognition site for the *E. coli* biotin ligase (BirA) (e.g., an AviTag) as present in the exemplified complex shown in FIG. 1 and used in the Examples. These elements were shown to have no effect on in vitro and in vivo functionality of the complex (data not shown). An exemplary minimal HLA-DR/CII peptide complex according to the present invention may be encoded by the amino acid sequences of SEQ ID NO: 18 and SEQ ID NO: 19. The person skilled in the art would understand that the peptide sequence may vary as encompassed by the claims and the His-tag may be replaced by an alternative positively charged peptide, such as a chondroitin binding peptide disclosed herein.

Sequences for exemplary complexes as used in the examples below are as follows:

1) DR4-Construct:

DR4 construct α-chain (SEQ ID NO:16), sequence comprising a signal peptide preceding the DRA*0101 extracellular α-chain region (underlined), a TEV cleavage site (bold), a cFos domain (bold and underlined) and a biotinylation site (BirA, italic and underlined):

MKLCILLAVVAFVGLSLGIKEEHVIIQAEFYLNPDQSGEFMFDFDGDEI

FHVDMAKKETVWRLEEFGRFASFEAQGALANIAVDKANLEIMTKRSNYT

PITNVPPEVTVLTNSPVELREPNVLICFIDKFTPPVVNVTWLRNGKPVT

TGVSETVFLPREDHLFRKFHYLPFLPSTEDVYDCRVEHWGLDEPLLKHW

EFDASGGGENLYFQGGGGGSLTDTLQAETDQLEDEKSALQTEIANLLKEK

EKLEFILAAHGGGGS*GLNDIFEAQKIEWHE*

Minimal DR4 construct α-chain (SEQ ID NO:18), sequence comprising a signal peptide preceding the DRA*0101 extracellular α-chain region (underlined), and a cFos domain (bold and underlined):

MKLCILLAVVAFVGLSLGIKEEHVIIQAEFYLNPDQSGEFMFDFDGDEIF

HVDMAKKETVWRLEEFGRFASFEAQGALANIAVDKANLEIMTKRSNYTPI

-continued

TNVPPEVTVLTNSPVELREPNVLICFIDKFTPPVVNVTWLRNGKPVTTGV

SETVFLPREDHLFRKFHYLPFLPSTEDVYDCRVEHWGLDEPLLKHWEFDA

SGGGGGGSLTDTLQAETDQLEDEKSALQTEIANLLKEKEKLEFILAAH

DR4 construct β-chain with hCII259-273 peptide (SEQ ID NO:17), sequence comprising a signal peptide immediately preceding a Strep-Tag (boldanddoubleunderlined) and the CII peptide259-273 (*italic and underline*), a thrombin cleavage site (bold and dotted line) framed by a glycine linker on each site, the DRB*0401 extracellular region (underlined), a TEV cleavage site (bold), a cJun domain (bold and underlined) and a His-Tag (italic):

MKLCILLAVVAFVGLSLGSAWSHPQFEK*GIAGFKGEQGPKGEPS*GGG

SLVPRGSGGGGSGDTRPRFLEQVKHECHFFNGTERVRFLDRYFYHQ

EEYVRFDSDVGEYRAVTELGRPDAEYWNSQKDLLEQKRAAVDTYCRH

NYGVGESFTVQRRVYPEVTVYPAKTQPLQHHNLLVCSVNGFYPGSIE

VRWFRNGQEEKTGVVSTGLIQNGDWTFQTLVMLETVPRSGEVYTCQV

EHPSLTSPLTVEWRARSGGGENLYFQGGGGSRIARLEEKVKTLKAQN

SELASTANMLREQVAQLKQKVMNH*HHHHHH*

Minimal DR4 construct β-chain with hCII259-273 peptide (SEQ ID NO: 19), sequence comprising a signal peptide immediately preceding the CII peptide259-273 (italic and underline), the DRB*0401 extracellular region (underlined), a cJun domain (bold and underlined) and a His-Tag (italic):

MKLCILLAVVAFVGLSLG*GIAGFKGEQGPKGEPS*GGGSGGGGSGDTRPR

FLEQVKHECHFFNGTERVRFLDRYFYHQEEYVRFDSDVGEYRAVTELGR

PDAEYWNSQKDLLEQKRAAVDTYCRHNYGVGESFTVQRRVYPEVTVYPA

KTQPLQHHNLLVCSVNGFYPGSIEVRWFRNGQEEKTGVVSTGLIQNGDW

TFQTLVMLETVPRSGEVYTCQVEHPSLTSPLTVEWRARSGGGGGGSRIA

RLEEKVKTLKAQNSELASTANMLREQVAQLKQKVMNH*HHHHHH*

2) DR4-hCLIPmut Construct:

DR4 construct α-chain as above (SEQ ID NO: 16).

DR4 construct β-chain with hCLIPmut (SEQ ID NO:20), sequence comprising a signal peptide immediately preceding a Strep-Tag (boldanddoubleunderlined) and the mutated hCLIP peptide (italic and underline), a thrombin cleavage site (bold and dotted line) framed by a glycine linker on each site, the DRB*0401 extracellular region (underlined), a TEV cleavage site (bold), a cJun domain (bold and underlined) and a His-Tag (italic):

MKLCILLAVVAFVGLSLGSAWSHPQFEK*PVSKARMATGALAQASGGG*

SLVPRGSGGGGSGDTRPRFLEQVKHECHFFNGTERVRFLDRYFYHQ

EEYVRFDSDVGEYRAVTELGRPDAEYWNSQKDLLEQKRAAVDTYCRH

NYGVGESFTVQRRVYPEVTVYPAKTQPLQHHNLLVCSVNGFYPGSIE

-continued

VRWFRNGQEEKTGVVSTGLIQNGDWTFQTLVMLETVPRSGEVYTCQV

EHPSLTSPLTVEWRARSGGGENLYFQGGGGS<u>RIARLEEKVKTLKAQN</u>

<u>SELASTANMLREQVAQLKQKVMNH</u>*HHHHHH*

3) Aq-rCII Construct:

Aq construct α-chain (SEQ ID NO: 21), sequence comprising a signal peptide preceding the Aq extracellular α-chain region (<u>underlined</u>), a TEV cleavage site (bold), a cFos domain (<u>bold and underlined</u>) and a biotinylation site (BirA, *italic and underlined*):

MKLCILLAVVAFVGLSLG<u>EDDIEADHVGFYGIVVYQSPGDIGQYTHEFD</u>

<u>GDEWFYVDLDKKETVWMLPEFGQLTSFDPQGGLQNIATGKHNLGGWTKR</u>

<u>SNFTPATNEAPQATVFPKSPVLLGQPNTLICFVDNIFPPVINITWLRNS</u>

<u>KSVTDGVYETSFLVNRDHSFHKLSYLTFIPSDDDIYDCKVEHWGLDEPV</u>

<u>LKHWEPEIPATMSELTETVS</u>GGGENLYFQGGGGS<u>LTDTLQAETDQLEDE</u>

<u>KSALQTEIANLLKEKEKLEFILAAH</u>GGGGS*GLNDIFEAQKIEWHE*

Aq construct β-chain with rat CII259-273 peptide (SEQ ID NO: 22), sequence comprising a signal peptide immediately preceding a Strep-Tag (<u>boldanddoubleunderlined</u>) and the CII peptide259-273 (*italic and underline*), a thrombin cleavage site (bold and dotted line) framed by a glycine linker on each site, the Aq extracellular region (<u>underlined</u>), a TEV cleavage site (bold), a cJun domain (<u>bold and underlined</u>) and a His-Tag (*italic*):

MKLCILLAVVAFVGLSLG<u>SAWSHPQFEK</u>*GIAGFKGEQGPKGET*SGGG

<u>SLVPRG</u>GSGGGGS<u>ERHFVAQLKGECYFTNGTQRIRSVNRYIYNREE</u>

<u>WVRFDSDVGEYRAVTELGRPDAEYWNSQPEILERTRAEVDTVCRHNY</u>

<u>EGVETHTSLRRLEQPNVAISLSRTEALNHHNTLVCSVTDFYPAKIKV</u>

<u>RWFRNGQEETVGVSSTQLIRNGDWTFQVLVMLEMTPHQGEVYTCHVE</u>

<u>HPSLKSPITVEWRAQSESARSKSGGG</u>ENLYFQGGGGS<u>RIARLEEKVK</u>

<u>TLKAQNSELASTANMLREQVAQLKQKVMNH</u>*HHHHHH*

Aq construct β-chain with rat CII259-273 peptide without His-tag (SEQ ID NO: 23), sequence comprising a signal peptide immediately preceding a Strep-Tag (<u>boldanddoubleunderlined</u>) and the CII peptide259-273 (*italic and underline*), a thrombin cleavage site (bold and dotted line) framed by a glycine linker on each site, the Aq extracellular region (<u>underlined</u>), a TEV cleavage site (bold) and a cJun domain (<u>bold and underlined</u>):

MKLCILLAVVAFVGLSLG<u>SAWSHPQFEK</u>*GIAGFKGEQGPKGET*SGGG

<u>SLVPRG</u>SSGGGGS<u>ERHFVAQLKGECYFTNGTQRIRSVNRYIYNREE</u>

<u>WVRFDSDVGEYRAVTELGRPDAEYWNSQPEILERTRAEVDTVCRHNY</u>

<u>EGVETHTSLRRLEQPNVAISLSRTEALNHHNTLVCSVTDFYPAKIKV</u>

-continued

RWFRNGQEETVGVSSTQLIRNGDWTFQVLVMLEMTPHQGEVYTCHVE

HPSLKSPITVEWRAQSESARSKSGGGENLYFQGGGGS<u>RIARLEEKVK</u>

<u>TLKAQNSELASTANMLREQVAQLKQKVMNH</u>

4) Aq-mCLIPmt Construct:

Aq construct α-chain as above (SEQ ID NO: 21)

Aq construct β-chain with mCLIP peptide (SEQ ID NO: 24), sequence comprising a signal peptide immediately preceding a Strep-Tag (<u>boldanddoubleunderlined</u>) and the mCLIPmt peptide (*italic and underline*), a thrombin cleavage site (bold and dotted line) framed by a glycine linker on each site, the Aq extracellular region (<u>underlined</u>), a TEV cleavage site (bold), a cJun domain (<u>bold and underlined</u>) and a His-Tag (*italic*):

MKLCILLAVVAFVGLSLG<u>SAWSHPQFEK</u>*PVSQARMATPLLMRP*SGGG

<u>SLVPRG</u>SGGGGS<u>ERHFVAQLKGECYFTNGTQRIRSVNRYIYNREEW</u>

<u>VRFDSDVGEYRAVTELGRPDAEYWNSQPEILERTRAEVDTVCRHNYE</u>

<u>GVETHTSLRRLEQPNVAISLSRTEALNHHNTLVCSVTDFYPAKIKVR</u>

<u>WFRNGQEETVGVSSTQLIRNGDWTFQVLVMLEMTPHQGEVYTCHVEH</u>

<u>PSLKSPITVEWRAQSESARSKSGGG</u>ENLYFQGGGGS<u>RIARLEEKVKT</u>

<u>LKAQNSELASTANMLREQVAQLKQKVMNH</u>*HHHHHH*

Aq construct β-chain with mCLIP peptide without His-tag (SEQ ID NO: 25), sequence comprising a signal peptide immediately preceding a Strep-Tag (<u>boldanddoubleunderlined</u>) and the mCLIPmt peptide (*italic and underline*), a thrombin cleavage site (bold and dotted line) framed by a glycine linker on each site, the Aq extracellular region (<u>underlined</u>), a TEV cleavage site (bold), a cJun domain (<u>bold and underlined</u>):

MKLCILLAVVAFVGLSLG<u>SAWSHPQFEK</u>*PVSQARMATPLLMRP*SGGG

<u>SLVPRG</u>SGGGGS<u>ERHFVAQLKGECYFTNGTQRIRSVNRYIYNREEW</u>

<u>VRFDSDVGEYRAVTELGRPDAEYWNSQPEILERTRAEVDTVCRHNYE</u>

<u>GVETHTSLRRLEQPNVAISLSRTEALNHHNTLVCSVTDFYPAKIKVR</u>

<u>WFRNGQEETVGVSSTQLIRNGDWTFQVLVMLEMTPHQGEVYTCHVEH</u>

<u>PSLKSPITVEWRAQSESARSKSGGG</u>ENLYFQGGGGS<u>RIARLEEKVKT</u>

<u>LKAQNSELASTANMLREQVAQLKQKVMNH</u>

Further amino acid sequences of individual elements of the constructs disclosed herein are provided below:

cFos domain (SEQ ID NO: 26):
LTDTLQAETDQLEDEKSALQTEIANLLKEKEKLEFILAAH cJun domain (SEQ ID NO: 27):
RIARLEEKVKTLKAQNSELASTANMLREQVAQLKQKVMNH modified human CLIP-peptide (SEQ ID NO: 28):
PVSKARMATGALAQA rat CII-peptide 259-273 (SEQ ID NO: 29):
GIAGFKGEQGPKGET streptavidin-tag (SEQ ID NO: 30):
SAWSHPQFEK.

In one embodiment the extracellular region of the HLA-DR alpha chain comprising at least an alpha 1 domain and the extracellular region of the HLA-DR beta chain comprising at least a beta 1 domain are expressed as a single fusion polypeptide (single chain heterodimer); and optionally the collagen II peptide (CII peptide) is fused to the N-terminus of the HLA-DR alpha chain or the HLA-DR beta chain by a linker peptide, preferably to the HLA-DR beta chain. In one embodiment the HLA-DR/CII peptide complex does not contain a multimerisation or heterodimerisation domains, particularly not an IgG domain. In one embodiment each HLA-DR/CII peptide complex only contains one extracellular region of the HLA-DR alpha chain and one extracellular region of the HLA-DR beta chain.

In an alternative embodiment the HLA-DR/CII complex comprises a first polypeptide comprising the extracellular region of the HLA-DR/CII alpha chain comprising at least an alpha 1 domain; a second polypeptide comprising the extracellular region of the HLA-DR/CII beta chain comprising at least a beta 1 domain; and the collagen II peptide (CII peptide), optionally fused to the N-terminus of the HLA-DR alpha chain or the HLA-DR beta chain by a linker peptide, preferably to the HLA-DR beta chain; and wherein HLA-DR alpha chain is fused at its C-terminal end to a first functional domain of a leucine zipper heterodimerization motif and the MHC class II beta chain is fused at its C-terminal end to a second complementary functional domain of a leucine zipper heterodimerization motif. The first functional domain and the second complementary functional domain may be an acidic and a basic leucine zipper heterodimerization domain, preferably a jun-fos leucine zipper motif. In one embodiment the jun-fos leucine zipper motive comprises a cFos domain having the amino acid sequence of SEQ ID NO: 26 and a cJun domain having the amino acid sequence of SEQ ID NO: 27. The person skilled in the art will understand that the first and/or the second polypeptide comprise the chondroitin-binding peptide, such as a polyhistidine tag, at the C-terminus of the functional domain of a leucine zipper heterodimerization motif. In one embodiment the HLA-DR/CII peptide complex does not contain further multimerisation or heterodimerisation domains, particularly not an IgG domain. In one embodiment each HLA-DR/CII peptide complex only contains one extracellular region of the HLA-DR alpha chain and one extracellular region of the HLA-DR beta chain.

The person skilled in the art will understand that the composition for use according to the invention, particularly if produced in a host production cell capable of post-translationally modifying lysine residues in collagen, may comprise HLA-DR/CII peptide complexes in a heterogeneous mixture of HLA-DR/CII peptide complexes comprising different post-translational modifications of the CII peptide, particularly the first and optional second lysine residue of the CII peptide and unmodified CII peptide. The heterogeneous mixture may comprise HLA-DR/CII peptide complexes comprising K, Hyl, G-Hyl or GG-Hyl at the first lysine and independently K, Hyl, G-Hyl or GG-Hyl at the optional second lysine (wherein K=lysine, Hyl=hydroxylysine, G-Hyl=galactosyl-hydroxylysine, GG-Hyl=glucosylgalactosy-lhydroxylysine).

Thus, in one embodiment the composition for use according to the present invention comprises HLA-DR/CII peptide complexes comprising the CII peptide, wherein the first lysine residue of the CII peptide is galactose-hydroxylysine and further comprises HLA-DR/CII peptide complexes comprising the CII peptide, wherein the first lysine residue of the CII peptide is unmodified, hydroxylysine (Hyl) or glucosylgalactosyl-hydroxylysine (GG-Hyl), preferably unmodified or hydroxylysine (Hyl) and the optional second lysine residue of the CII peptide is independently unmodified, hydroxylysine (Hyl), galactosyl-hydroxylysine (G-Hyl) or glucosylgalactosyl-hydroxylysine (GG-Hyl), preferably unmodified, hydroxylysine (Hyl), galactosyl-hydroxylysine (G-Hyl). In one embodiment the composition does not comprise glucosyl-galactosyl-hydroxylysine (GG-Hyl) modified HLA-DR/CII peptide complexes, i.e., HLA-DR/CII peptide complexes comprising an O-glycosylated CII peptide wherein the first and/or the optional second lysine residue are glucosyl-galactosyl-hydroxylysine.

In the composition for use according to the invention comprising HLA-DR/CII peptide complexes in a heterogeneous mixture of HLA-DR/CII peptide complexes, the composition preferably comprises HLA-DR/CII peptide complexes comprising at least 5%, at least 10%, at least 20%, at least 30%, at least 40% or at least 50% of G-Hyl at the first lysine (K264) of the CII peptide of total HLA-DR/CII peptide complexes in the mixture or the composition. Further, the composition comprises HLA-DR/CII peptide complexes comprises no more than 90%, no more than 80%, no more than 70%, no more than 60%, or no more than 50% unmodified CII peptides of total HLA-DR/CII peptide complexes in the mixture or the composition. In certain embodiments, the composition comprises HLA-DR/CII peptides complexes comprising preferably less than 20%, less than 10%, less than 5% and more preferably less than 1% GG-Hyl in the CII peptide of total HLA-DR/CII peptide complexes in the mixture or the composition. Wherein the percentage refers to percent of CII peptide in the HLA-DR/CII peptide complexes of total CII peptides in the HLA-DR/CII peptide complexes. In a particular preferred embodiment said second lysine residue (K270) is mutated, for example mutated to arginine (K270R). In a further embodiment the (optional) second lysine is not post-translationally modified to glucosylgalactosyl-hydroxylysine (GG-Hyl) and is present as unmodified lysine, hydroxylysine or galactosyl-hydroxylysine.

The person skilled in the art will understand that the composition for use according to the invention may alternatively comprise HLA-DR/CII peptide complexes in a homogenous mixture of HLA-DR/CII peptide complexes comprising unmodified CII peptides or the same post-translational modification of the CII peptide, particularly of the first lysine residue of the CII peptide. The homogenous mixture may comprise HLA-DR/CII peptide complexes comprising K, Hyl, G-Hyl or GG-Hyl at the first lysine of the CII peptide (wherein K=lysine, Hyl=hydroxylysine, G-Hyl=galactosyl-hydroxylysine, GG-Hyl=glucosylgalactosyl-hydroxylysine). Preferably HLA-DR/CII peptide complexes comprise no modification or at least no GG-Hyl at the second lysine of the CII peptide, if present. A homogenous mixture of HLA-DR/CII peptide complexes may be achieved by loading the HLA-DR protein with a synthetically prepared unmodified or post-translationally modified CII peptides. Alternatively the HLA-DR/CII peptide complex may be produced using a host production cell line capable of post-translationally modifying lysine residues in collagen and purifying the respective HLA-DR/CII peptides complexes using affinity chromatography using antibodies that recognize the complexes in a post-translational modification sensitive manner or using TCRs (or fragments thereof) specific for said HLA-DR/CII complexes as affinity ligands.

In a further aspect the present invention provides a recombinant HLA-DR/CII peptide complex, obtained or obtainable by the method disclosed herein for use in treating chronic inflammatory diseases in a human patient, wherein the method of producing a HLA-DR/CII peptide complex comprises transfecting a mammalian cell with (i) a polynucleotide encoding a polypeptide comprising an extracellular region of the a HLA-DR alpha chain comprising at least an alpha 1 domain; (ii) a polynucleotide encoding a polypeptide comprising an extracellular region of the a HLA-DR beta chain comprising at least a beta 1 domain; and (iii) a polynucleotide encoding a collagen II peptide (CII peptide) fused to the N-terminus of the HLA-DR alpha chain or the HLA-DR beta chain by a linker peptide, wherein the CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6), AGFKGXQGPXG (SEQ ID NO: 7) and AGFKXEQGPXG (SEQ ID NO: 8), and wherein the HLA-DR/CII peptide complex comprises a chondroitin-binding peptide at the C-terminal end of the polypeptide comprising the HLA-DR alpha chain and/or the HLA-DR beta chain; (b) cultivating the mammalian cells under conditions suitable to produce the HLA-DR/CII peptide complex, and (c) harvesting a cell supernatant and optionally cells comprising the HLA-DR/CII peptide complex comprising an unmodified and/or post-translationally modified CII peptide. In the post-translationally modified CII peptide at least the first lysine residue of the CII peptide may be hydroxylysine (Hyl) or O-glycosylated Hyl. Preferably, the at least first lysine residue is hydroxylysine or galactosyl-hydroxylysine, more preferably galactosyl-hydroxylysine. Particularly encompassed is said recombinant HLA-DR/CII peptide complex comprising a post-translationally modified CII peptide, wherein the first lysine residue of the CII peptide is hydroxylysine (Hyl) or is O-glycosylated Hyl. Thus, in one embodiment the recombinant HLA-DR/CII peptide complex comprising an O-glycosylated CII peptide is obtained by the method described herein.

In certain embodiments the CII peptide comprises the amino acid sequence of AGFKGEQGPKG (SEQ ID NO: 1), AGFKGEQGPX$_1$G (SEQ ID NO: 2), AGFKGEX$_2$GPKG (SEQ ID NO: 3), AGFKGX$_3$QGPKG (SEQ ID NO: 4), AGFKX$_4$EQGPKG (SEQ ID NO: 5), AGFKGEX$_2$GPX$_1$G (SEQ ID NO: 6) and AGFKGX$_3$QGPX$_1$G (SEQ ID NO: 7), AGFKX$_4$EQGPX$_1$G (SEQ ID NO: 8), wherein X$_1$ is any of the proteinogenic amino acids except K, preferably R, A, G or Q, more preferably R; X$_2$ is any of the proteinogenic amino acids except Q; preferably A, R, H or G; X$_3$ is any of the proteinogenic amino acids except E, preferably A, D, Q or G; and X$_4$ is any of the proteinogenic amino acids except G, more preferably A, S, V or L. Preferably X$_2$, X$_3$ or X$_4$ is not K. In certain embodiments the CII peptide comprises the amino acid sequence of AGFKGEQGPKG (SEQ ID NO: 1) or AGFKGEQGPX$_1$G (SEQ ID NO: 2), preferably of AGFKGEQGPKGEP (SEQ ID NO: 10) or AGFKGEQGPX$_1$GEP (SEQ ID NO: 11), more preferably of GIAGFKGEQGPKGEP (SEQ ID NO: 13) or GIAGFKGEQGPX$_1$GEP (SEQ ID NO: 14).

In yet a further aspect the present invention provides a composition comprising the recombinant HLA-DR/CII peptide complex comprising a CII peptide obtained by the method described herein.

The composition for use according to the invention is a pharmaceutical composition. Thus the present invention also discloses pharmaceutical compositions comprising the composition comprising recombinant HLA-DR/CII peptide complexes as described herein and pharmaceutically acceptable excipients. The composition or pharmaceutical composition may be administered by any route of administration, preferably subcutaneously (s.c.) or intravenously (i.v.). In one embodiment the composition or pharmaceutical composition is administered using an osmotic pump implanted subcutaneously. The composition or pharmaceutical composition comprising the recombinant HLA-DR/CII peptide complexes for use according to the invention may be lyophilized or in an aqueous solution. Pharmaceutically acceptable excipients may include carriers as well as stabilizers.

The composition for use according to the present invention is for treating chronic inflammatory diseases, particularly arthritis or other chronic inflammatory joint disease. Preferably the composition is a pharmaceutical composition further comprising pharmaceutically acceptable excipients. In one embodiment the composition is for use in treating chronic inflammatory disease is selected from the group consisting of rheumatoid arthritis, osteoarthritis, psoriatic arthritis, non-radiographic axial spondyloarthritis, ankylosing spondylitis, juvenile idiopathic arthritis, relapsing polychondritis, systemic lupus erythematosus, Lyme disease, Meniere diseases, autoimmune inner ear disease (AIED), or Still's disease. In one embodiment the composition for use according to the invention is for treating a form of arthritis selected from the group consisting of rheumatoid arthritis, osteoarthritis, psoriatic arthritis, ankyloses spondylitis, juvenile idiopathic arthritis or Still's disease, preferably rheumatoid arthritis, osteoarthritis or psoriatic arthritis, more preferably rheumatoid arthritis. In particular embodiments the composition according to the invention is for first line treatment of rheumatoid arthritis, for treatment in subjects inadequately responding to methotrexate and/or conventional synthetic (small molecule) disease modifying antirheumatic drugs (DMARDs), for treatment in subjects inadequately responding to biologic DMARDs (e.g., anti-TNF, anti-CTLA4 (abatacept) anti-IL-6, anti-CD20 (rituximab) antibodies), for treatment in subjects inadequately responding to targeted synthetic DMARDs (e.g., JAK-inhibitors). In alternative embodiments the composition according to the invention is for prophylactic treatment in patients at high risk to develop rheumatoid arthritis, such as anti-ccp antibody positive smokers with new onset of musculoskeletal symptoms.

Preferably the composition is to be administered subcutaneously or intravenously, more preferably subcutaneously. The composition may be administered at single doses of about 10 µg to about 250 µg, preferably 20 to 200 µg, more preferably 50 µg to 100 µg. In one embodiment, treatment comprises a loading and a maintenance phase. The loading phase may comprise 3 to 10, preferably 6 sequential applications on consecutive days. Maintenance doses may be administered weekly or every 3 to 14 days, preferably weekly, biweekly, monthly, every two months or at even higher intervals.

Methods for Producing Recombinant HLA-DR/CII Peptide Complex

The HLA-DR/CII peptide complexes for use according to the invention may be prepared in vivo (i.e., within a mammalian cell line) with the CII peptide fused to the N-terminus of the extracellular part of the beta chain or the alpha chain or alternatively with a surrogate peptide fused to the N-terminus of the extracellular part of the beta chain or the alpha chain and subsequent cleavage of the surrogate peptide and loading with the CII peptide. If the CII peptide is expressed together with the HLA-DR protein in mammalian cells, depending on the mammalian cells used for production the CII peptide may be post-translationally modified or unmodified. If the CII peptide is loaded onto the HLA-DR protein, the CII peptide is prepared synthetically or enzymatically in vitro and may be loaded onto the complex as unmodified and/or post-translationally modified CII peptide.

More specifically HLA-DR/CII peptide complexes for use according to the invention may be prepared by a method of producing a HLA-DR/CII peptide complex comprising a CII peptide comprises transfecting a mammalian cell with (i) a polynucleotide encoding a polypeptide comprising an extracellular region of the HLA-DR alpha chain comprising at least an alpha 1 domain; (ii) a polynucleotide encoding a polypeptide comprising an extracellular region of the HLA-DR beta chain comprising at least a beta 1 domain, comprising a class II-associated invariant chain peptide (CLIP) as a surrogate peptide fused to the N-terminus of the extracellular part of the beta chain or the alpha chain, preferably the beta chain, by a linker peptide comprising a protease cleavage site (e.g., a thrombin cleavage site); wherein the HLA-DR protein comprises a chondroitin-binding peptide at the C-terminal end of the polypeptide comprising the HLA-DR alpha chain and/or the HLA-DR beta chain; (b) cultivating the mammalian cells under conditions suitable to produce the HLA-DR protein; (c) harvesting a cell supernatant and optionally cells comprising the HLA-DR protein; (d) cleaving off CLIP using a protease (e.g., thrombin) recognizing said protease cleavage site; and loading the HLA-DR protein with an unmodified and/or post-translationally modified CII peptide to form the HLA-DR/CII peptide complex, wherein the CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6), AGFKGXQGPXG (SEQ ID NO: 7) and AGFKXEQGPXG (SEQ ID NO: 8). In the post-translationally modified CII peptide at least the first lysine residue of the CII peptide may be hydroxylysine (Hyl) and/or O-glycosylated Hyl. Preferably, the at least first lysine residue in the post-translationally modified CII peptide is hydroxylysine and/or galactosyl-hydroxylysine, more preferably galactosyl-hydroxylysine. Thus, following production the peptide is proteolytically cleaved off and a synthetically prepared galactosylated peptide (i.e., a CII peptide carrying gal-Hyl at position K264) and/or an unmodified CII peptide is loaded in vitro onto the complex. Although this synthetic galactosylated peptide and/or unmodified may be covalently linked to the HLA-DR protein, this linkage is not via a linker peptide.

Alternatively, the composition for use according to the present invention may be prepared by a method of producing a HLA-DR/CII peptide complex comprising a CII peptide comprises transfecting a mammalian cell with (i) a polynucleotide encoding a polypeptide comprising an extracellular region of the a HLA-DR alpha chain comprising at least an alpha 1 domain; (ii) a polynucleotide encoding a polypeptide comprising an extracellular region of the a HLA-DR beta chain comprising at least a beta 1 domain; and (iii) a polynucleotide encoding a collagen II peptide (CII peptide) fused to the N-terminus of the HLA-DR alpha chain or the HLA-DR beta chain by a linker peptide, wherein the CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG SEQ ID NO: 4), AGFKXEQGPKG (SEQ ID NO: 5), AGFKGEXGPXG (SEQ ID NO: 6), AGFKGXQGPXG (SEQ ID NO: 7) and AGFKXEQGPXG (SEQ ID NO: 8), and wherein the HLA-DR/CII peptide complex comprises a chondroitin-binding peptide at the C-terminal end of the polypeptide comprising the HLA-DR alpha chain and/or the HLA-DR beta chain; (b) cultivating the mammalian cells under conditions suitable to produce the HLA-DR/CII peptide complex, and (c) harvesting a cell supernatant and optionally cells comprising the HLA-DR/CII peptide complex comprising an unmodified and/or post-translationally modified CII peptide. In the post-translationally modified CII peptide at least the first lysine residue of the CII peptide may be hydroxylysine (Hyl) or O-glycosylated Hyl. Preferably, the at least first lysine residue is hydroxylysine or galactosyl-hydroxylysine, more preferably galactosyl-hydroxylysine.

The method may further comprise a step of analysing the glycosylation profile of the CII peptide of the HLA-DR/CII peptide complex. Methods for analyzing the glycosylation profile are well known in the art and include methods such as mass spectrometry. The method of producing a HLA-DR/CII peptide complex is an in vitro method, in the sense that the HLA-DR/CII peptide complexes are produced in a cell line in a cell culture dish or fermenter. Further the method comprises the use of mammalian cell lines, rather than primary cells.

In certain embodiments the CII peptide comprises the amino acid sequence of AGFKGEQGPKG (SEQ ID NO: 1), AGFKGEQGPX$_1$G (SEQ ID NO: 2), AGFKGEX$_2$GPKG (SEQ ID NO: 3), AGFKGX$_3$QGPKG (SEQ ID NO: 4), AGFKX$_4$EQGPKG (SEQ ID NO: 5), AGFKGEX$_2$GPX$_1$G (SEQ ID NO: 6), AGFKGX$_3$QGPX$_1$G (SEQ ID NO: 7) and AGFKX$_4$EQGPX$_1$G (SEQ ID NO: 8), wherein X$_1$ is any of the proteinogenic amino acids except K, preferably R, A, G or Q, more preferably R; X$_2$ is any of the proteinogenic amino acids except Q; preferably A, R, H or G; X$_3$ is any of the proteinogenic amino acids except E, preferably A, D, Q or G; and X$_4$ is any of the proteinogenic amino acids except G, more preferably A, S, V or L. Preferably X$_2$, X$_3$ or X$_4$ is not K. In certain embodiments the CII peptide comprises the amino acid sequence of AGFKGEQGPKG (SEQ ID NO: 1) or AGFKGEQGPX$_1$G (SEQ ID NO: 2), preferably of AGFKGEQGPKGEP (SEQ ID NO: 10) or AGFKGEQGPX$_1$GEP (SEQ ID NO: 11), more preferably of GIAGFKGEQGPKGEP (SEQ ID NO: 13) or GIAGFKGEQGPX$_1$GEP (SEQ ID NO: 14).

Preferably at least the alpha 1 domain is from DRA*0101 and at least the beta 1 domain is from a HLA-DR allele selected from the group consisting of DRB1*0401, DRB1*0404, DRB1*0405, DRB1*0408, DRB1*0409, DRB1*0101, DRB1*0102, DRB1*1001, DRB1*1402 and DRB1*1303, preferably DRB1*0401, DRB1*0404, DRB1*0405, DRB1*0408, DRB1*0409, DRB1*0101, DRB1*0102, DRB1*1001 and DRB1*1402, more preferably DRB1*0401, DRB1*0404 and DRB1*0405, even more preferably DRB1*0401. More preferably the alpha 1 domain and the alpha 2 domain is from DRA*0101 (alpha 1 and 2 domains: amino acids 19-200 of SEQ ID NO: 16) and the beta 1 domain and the beta 2 domain is from a HLA-DR allele selected from the group consisting of DRB1*0401, DRB1*0404 and DRB1*0405, DRB1*0408, DRB1*0409, DRB1*0101, DRB1*0102, DRB1*1001, DRB1*1402 and DRB1*1303, preferably DRB1*0401, DRB1*0404, DRB1*0405, DRB1*0408, DRB1*0409, DRB1*0101, DRB1*0102, DRB1*1001 and DRB1*1402, more preferably DRB1*0401, DRB1*0404 and DRB1*0405, even more preferably DRB1*0401 (beta 1 and 2 domain: amino acids 60-250 of SEQ ID NO: 17).

The specific HLA-DR/CII peptide complexes used in the examples are abbreviated as follows: DR4/hCII (naturally glycosylated, human), DR4/nCII (naked or non-modified, human), DR4/galCII (galactosylated (Gal-Hyl at K264), human), wherein the CII peptide used has the amino acid sequence GIAGFKGEQGPKGEP (SEQ ID NO: 13). The respective mouse MHCII/CII complexes used in the examples are abbreviated as follows: Aq/rCII (naturally glycosylated, rat CII), Aq/nCII (naked or non-modified, rat CII), Aq/galCII (galactosylated (Gal-Hyl at K264), rat), wherein the rat CII peptide used has the amino acid sequence GIAGFKGEQGPKGET (SEQ ID NO: 29), The collagen II peptide (CII peptide) may be fused to the N-terminus of the HLA-DR alpha chain or the HLA-DR beta chain by a linker peptide, preferably to the N-terminus of the HLA-DR beta chain. The term "linker peptide" refers to a polypeptide consisting of multiple amino acid residues. The linker peptide may be any peptide as long as it is long and flexible enough to allow the peptide to bind to the peptide binding pocket formed by the HLA-DR complex. An example of a suitable linker is a Gly-Ser linker. The CII peptide, the peptide linker and at least one of the extracellular regions of the HLA-DR alpha chain and the HLA-DR chain may be expressed as one polypeptide and encoded by one polynucleotide. The term "fused to" in this context means "linked to" wherein the linking is via peptide bonds, optionally using a linker peptide, and therefore a fusion protein is generated.

The HLA-DR/CII peptide complexes contain at least one chondroitin-binding peptide, preferably a chondroitin- and hyaluronic acid (also referred to as hyaluronan) binding peptide. Preferably the chondroitin-binding peptide is located at the C-terminal end of at least one polypeptide chain of the complex. In one embodiment the HLA-DR/CII peptide complex comprises at least one C-terminal chondroitin-binding peptide. Chondroitin-binding peptides are known in the art and include without being limited thereto peptides having the amino acid sequences EKRIWFPYRRF (SEQ ID NO: 31), YKTNFRRYYRF (SEQ ID NO: 32) or VLIRHFRKRYY (SEQ ID NO: 33) (Butterfield K C et al., Biochemistry. 2010 Feb. 23; 49(7): 1549-55). Also positively charged histone peptides have been identified herein, particularly peptides of human H2A histone such as a peptide comprising the sequence SGRGKQGGKARA-KAKTRSSR (SEQ ID NO: 34). In one embodiment the chondroitin binding peptide comprises 5 to 20 amino acids, preferably 6 to 20 amino acids, more preferably 6 to 12 amino acids. Preferably the chondroitin binding peptide comprises 5 or more, preferably 6 or more, more preferably 7 or more positively charged amino acids. In addition or independently the chondroitin binding peptide comprises at least two consecutive positively charged amino acids, preferably at least three consecutive positively charged amino acids. Also more basic amino acids, such as lysine (pK of 10.5) and arginine (pK of 12.5), seem to improve the chondroitin binding effect histidine (pK of 6.0), particularly for alternating positively charged amino acids. However care should be taken to avoid changing the biochemical characteristics of the protein by including a very basic peptide. In one embodiment the chondroitin-binding peptide is a polyhistidine-tag, preferably having at least 6 consecutive histidine residues (at least a hexahistidine-tag), more preferably having at least 7 consecutive histidine residues (at least a heptahistidine-tag).

The term chondroitin and chondroitin sulfate are used interchangeably herein and hence the chondroitin-binding peptide may also be referred to as chondroitin sulfate binding peptide. To increase binding to hyaluronan an exemplary sequence containing the binding consensus motif is defined as follows: B(X7) B, in which B is either R or K and X7 contains no acidic residues and at least one basic amino acid (Yang B et al., EMBO J. 1994 Jan. 15; 13(2): 286-96). As disclosed herein the HLA-DR/CII peptide complex can also bind to chondroitin sulfate via the his-tag. Thus, the condroitin-binding peptide may be a polyhistidine-tag or any other amino acid sequences that increase binding affinity to chondroitin, such as. EKRIWFPYRRF (SEQ ID NO: 31), YKTNFRRYYRF (SEQ ID NO: 32), VLIRHFRKRYY (SEQ ID NO: 33) or SGRGKQGGKARAKAKTRSSR (SEQ ID NO: 34). A polyhistidine tag may be a hexahistidine-tag (6xHis, HHHHHH; SEQ ID NO:41), more preferably a heptahistidine-tag (7xHis; HHHHHHH; SEQ ID NO: 42), a histidine tag comprising at least 7 consecutive histidines, or a modified histidine tag comprising at least 6 histidines, such as a HQ tag, comprising alternating histidine and glutamine, a HN tag comprising alternating histidine and asparagine or a HAT tag comprising the amino acid sequence KDH-LIHNVHKEEHAHAHNK (SEQ ID NO: 36). In case the HLA-DR/CII peptide complexes comprise a heterodimerisation domain, the chondroitin-binding peptide is C-terminal of the heterodimerisation domain. Chondroitin and hyaluronic acid are both important components of cartilage.

Transfecting as used herein means introducing the DNA into the mammalian cell using transfection methods known in the art. As used herein the term "transfection" or "transfecting" includes "transduction" and "transducing", which is often used to describe virus-mediated gene transfer into eukaryotic cells. The polynucleotide may be DNA or RNA, preferably DNA. Transfection may be transient transfection or stable transfection. Preferably the polynucleotide is present in a vector, preferably an expression vector.

Methods for stable integration are well known in the art. Briefly, stable integration is commonly achieved by transiently introducing the at least one recombinant polynucleotide or a vector containing the at least one recombinant polynucleotide into the mammalian host cell, which facilitates the stable integration of said recombinant polynucleotide(s) into the mammalian cell genome. Typically the recombinant polynucleotide is flanked by homology arms, i.e., sequences homologous to the region upstream and downstream of the integration site. A vector to introduce the recombinant polynucleotide into the mammalian cell may be chosen from a great variety of suitable vector systems, such as plasmids, retroviruses, cosmids, EBV-derived episomes, and the like. Various shuttle vectors may be used, e.g., vectors which may autonomously replicate in a plurality of host microorganisms such as E. coli and Pseudomonas sp. Before their introduction into the mammalian host cell, circular vectors may be linearized to facilitate integration into the mammalian cell genome. Methods for the introduction of vectors into mammalian cells are well known in the art and include transfection with biological methods, such as viral delivery, with chemical methods, such as using cationic polymers, calcium phosphate, cationic lipids or cationic amino acids; with physical methods, such as electroporation or microinjection.

The recombinant polynucleotide stably integrated into the genome of the mammalian cell may be part of an expression cassette. An expression cassette comprises at least one heterologous polynucleotide coding for a gene product, such as a RNA and/or a protein, operably linked to a promoter and optionally further means controlling the expression of the gene product(s). Such means include, but are not limited to enhancers, termination signals, polyadenylation signals and a 3' untranslated region, typically containing a polyadenylation site. The promoter may be a weak promoter, or a strong promoter supporting high level expression of the gene product of interest. Said promoters include, but are not limited to CMV (cytomegalovirus) promoters, SV40 (Simian vacuolating virus 40) promoters, the RSV (Rous Sarcoma Virus) promoters, adenovirus promoters (e.g., the adenovirus major late promoter (AdMLP), CHEF-1 (CHO-derived elongation factor-1) promotors, polyoma and strong mammalian promoters such as native immunoglobulin and actin promoters or the natural promoter of the at least one heterologous polynucleotide. Preferably, the promoter is a CMV promoter or an SV40 promoter, most preferably a CMV promoter. Examples for polyadenylation signals are BGH polyA, SV40 late or early polyA; alternatively, 3'UTRs of immunoglobulin genes etc. can be used. The skilled person will further understand that the 3' untranslated region may be engineered to support high level expression, e.g., by removing instability elements, such as AREs (adenylate-uridylate rich elements).

The gene product may further be placed under the control of an amplifiable genetic selection marker, such as dihydrofolate reductase (DHFR), glutamine synthetase (GS). The amplifiable selection marker gene can be on the same expression vector as the secreted therapeutic protein expression cassette. Alternatively, the amplifiable selection marker gene and the secreted therapeutic protein expression cassette can be on different expression vectors, but integrate in close proximity into the host cell's genome. Two or more vectors that are co-transfected simultaneously, for example, often integrate in close proximity into the host cell's genome. Amplification of the genetic region containing the secreted therapeutic protein expression cassette is then mediated by adding the amplification agent (e.g., MTX for DHFR or MSX for GS) into the cultivation medium.

Sufficiently high stable levels of the gene product in the host cell or the producer cell may be achieved, e.g., by cloning multiple copies of a heterologous polynucleotide into an expression vector. Cloning multiple copies of the recombinant polynucleotide into an expression vector and amplifying the secreted therapeutic protein expression cassette (encoding for the HLA-DR/CII peptide complex) as described above may further be combined.

The polynucleotide encoding an extracellular region of the HLA-DR alpha chain comprising at least an alpha 1 domain may be present in one vector (first polynucleotide) and the polynucleotide encoding an extracellular region of the HLA-DRchain comprising at least a beta 1 domain (second polynucleotide) in another vector, wherein the chondroitin-binding peptide is further encoded by either the first or the second polynucleotide to provide a chondroitin-binding peptide at the C-terminal end of the polypeptide comprising the HLA-DR alpha chain and/or the HLA-DR beta chain. Alternatively, the first and the second polynucleotide may be part of separate expression cassettes on the same vector. The first and the second polynucleotide may also form a single polynucleotide encoding a single fusion polypeptide comprising the extracellular region of the HLA-DRalpha chain comprising at least an alpha 1 domain; the extracellular region of the HLA-DRbeta chain comprising at least a beta 1 domain; and optionally further the collagen II peptide (CII peptide) fused to the N-terminus of the HLA-DR alpha chain or the HLA-DR beta chain by a linker peptide, preferably to the HLA-DR beta chain, wherein the HLA-DR/CII peptide complex comprises a chondroitin-binding peptide at the C-terminal end of the polypeptide of the fusion polypeptide (single chain heterodimer).

Alternatively, in case the HLA-DR protein is expressed as two polypeptides, the HLA-DR alpha chain is fused at its C-terminal end (C-terminally) to a first functional domain of a leucine zipper heterodimerization motif and the HLA-DR beta chain is fused at its C-terminal end to a second complementary functional domain of a leucine zipper heterodimerization motif. The first functional domain and the second complementary functional domain may be an acidic and a basic leucine zipper heterodimerization domain, preferably a jun-fos leucine zipper motif. The first and/or the second polynucleotide further encode(s) a chondroitin-binding peptide, such as a polyhistidine tag, at the C-terminal end of the functional domain of a leucine zipper heterodimerization motif.

The mammalian cell is cultivated under conditions suitable to produce the HLA-DR/CII peptide complex, and the cell supernatant and/or the cells are harvested, wherein the cell supernatant and/or the cells comprise(s) the HLA-DR/CII peptide complex comprising an unmodified and/or a post-translationally modified CII peptide. In the post-translationally modified CII peptide the first lysine residue of the CII peptide may be hydroxylysine (Hyl) or O-glycosylated hydroxylysine, preferably the first lysine residue is hydroxylysine or galactosyl-hydroxylysine, more preferably galactosyl-hydroxylysine. The method may further comprise a step of analysing the glycosylation profile of the CII peptide of the HLA-DR/CII peptide complex. Methods for analyzing the glycosylation profile are well known in the art and include methods such as mass spectrometry.

In principle, any mammalian cell suitable for high yield protein production may be used for the production of the HLA-DR/CII peptide complex, including HEK293 cells and CHO cells. In case the CII peptide is fused to the N-terminus of the HLA-DR alpha chain or the HLA-DR beta chain by a linker peptide and the CII peptide is to be post-translationally modified, the mammalian cells line is suitable, as long as it comprises enzymes to post-translationally modify lysine residues in collagen, comprising hydroxylating lysine to hydroxylysine (Hyl) and galactosylating Hyl to galactosylhydroxylysine (Gal-Hyl). The term "galactosylated" as used herein in the context of lysine includes that the lysine has been hydroxylated to hydroxylysine prior to galactosylation. The enzymes may be endogenously present in the cell or may be recombinantly expressed in the cell. Preferably the mammalian cell comprises a lysylhydroxylase (EC 1.14.11.4) and a collagen galactosyltransferase (EC 2.4.1.50), preferably lysylhydroxylase 1 (LH1) and/or lysylhydroxylase 2 (LH2) and collagen galactosyltransferase GLT25D1 and/or GLT25D2, preferably GLT25D1. These enzymes post-translationally modify collagen. Thus, these enzymes are likely to be present in cell lines producing collagen, such as kidney cells, fibroblast cells or osteoclast cells, particularly kidney cells, such as HEK 293 cells or derivatives thereof. The HEK 293 cells may be grown as adherent cells or in suspension. An example for a HEK 293 cell suitable for the method according to the invention is the HEK 293 cell or the HEK 293F cell, such as the Expi293F cell (Gibco, Cat. No. A14527, also available as cGMP banked Cat. No. 100044202). Other suitable HEK 293 cells include HEK 293T cells and/or suspension cells thereof. It was surprising that also small peptides presented by MHC II proteins can be post-translationally modified in these cells. Although the peptides are derived from collagen they are present in an entirely different (unnatural) environment within the MHC II complex. We note in this regard that naturally MHC II proteins get loaded with peptides from extracellular (post-translationally modified) proteins that get digested in the APC. Thus, the modification is already present on the endocytosed protein and is not added intracellularly.

Furthermore, it has been surprising that the heterogeneous product produced when glycosylated in situ is suitable for therapy. Suitable cells can be easily screened for the enzymes required for post-translational modification of lysine residues in collagen, such as by western blot using suitable antibodies or by RNA expression, or functionally by their ability to glycosylate type II collagen or HLA-DR/CII peptide complexes. Methods for detecting gene or protein expression or enzyme activity and glycosylation profiles are well known in the art. Examples for suitable mammalian cells are a kidney cell, a fibroblast cell or an osteoblast cell, preferably a HEK 293 cell or cell line. HEK 293 cells have been described previously to express lysylhydroxylases PLOD1 and PLOD2 (encoding for LH1 and LH2, respectively), galactosyltransferases GLT25D1 and GLT25D2 and further PLOD3 (encoding for LH3).

CHO cells commonly used for protein production have been tested and are not able to sufficiently add post-translational modifications at the lysine residues resulting in galactosylhydroxylysine (Gal-Hyl) in collagen or in the HLA-DR/CII peptide complex described herein. However, the mammalian cell may also be a cell genetically engineered to express a lysylhydroxylase and a collagen galactosyltransferase. Preferably the mammalian cell is genetically engineered to recombinantly express lysylhydroxylase 1 (LH1) and/or lysylhydroxylase 2 (LH2) and collagen galactosyltransferase GLT25D1 and/or GLT25D2, preferably GLT25D1. GLT25D2 is expressed in only a few cell types and is therefore less likely to be responsible for normal collagen modification. Any mammalian cell may be genetically engineered to recombinantly express a lysylhydroxylase and a collagen galactosyltransferase, preferably lysylhydroxylase 1 (LH1) and/or lysylhydroxylase 2 (LH2) and collagen galactosyltransferase GLT25D1 and/or GLT25D2. Preferably the genetically engineered mammalian cell as described is a CHO cell, more preferably a CHO-DG44 cell, a CHO-K1 cell, a CHO-DXB11 cell, a CHO-S cell, a CHO glutamine synthetase (GS)-deficient cell or a derivative of any of these cells.

The person skilled in the art will understand that the HLA-DR/CII peptide complexes produced in a mammalian cell capable to post-translationally modify lysine residues in collagen, i.e., comprising enzymes to post-translationally modify lysine residues in collagen, are a heterogeneous mixture of HLA-DR/CII peptide complexes comprising different post-translational modifications of the CII peptide, particularly at the first and optional second lysine residue of the CII peptide. The heterogeneous mixture comprises HLA-DR/CII peptide complexes comprising K, Hyl, G-Hyl or GG-Hyl at the first lysine and independently K, Hyl, G-Hyl or GG-Hyl at the optional second lysine (wherein K=lysine, Hyl=hydroxylysine, G-Hyl=galactosylhydroxylysine, GG-Hyl=glucosylgalactosyl-hydroxylysine).

Thus, the harvested cell supernatant and optionally harvested cells comprises HLA-DR/CII peptide complexes comprising the CII peptide, wherein the first lysine residue of the CII peptide is Hyl or gal-Hyl and further comprises HLA-DR/CII peptide complexes comprising the CII peptide, wherein the first lysine residue of the CII peptide is unmodified or glucosylgalactosyl-hydroxylysine (GG-Hyl), preferably unmodified and the optional second lysine residue of the CII peptide is independently unmodified, hydroxylysine (Hyl), galactosyl-hydroxylysine (G-Hyl) or glucosylgalactosyl-hydroxylysine (GG-Hyl), preferably unmodified, hydroxylysine (Hyl) or galactosyl-hydroxylysine (G-Hyl). Preferably the harvested cell supernatant and optionally harvested cells do not comprise HLA-DR/CII peptide complexes, wherein the second lysine residue is glucosylgalactosyl-hydroxylysine. More preferably the harvested cell supernatant and optionally harvested cells do not comprise glucosylgalactosyl-hydroxylysine (GG-Hyl) modified HLA-DR/CII peptide complexes, i.e., HLA-DR/CII peptide complexes comprising an O-glycosylated CII peptide wherein the first and/or the optional second lysine residue are glucosylgalactosyl-hydroxylysine. A mixture of HLA-DR/CII peptide complexes may also be achieved by loading unmodified and post-translationally modified CII peptides onto HLA-DR proteins. The person skilled in the art will understand that different ratios may be achieved.

The heterogeneous mixture of HLA-DR/CII peptide complexes (prepared by CII peptide loading or CII peptide expression as fusion protein with the HLA-DR protein) comprises at least 5%, at least 10%, at least 20%, at least 30%, at least 40% or at least 50% of G-Hyl at the first lysine (K264) of the CII peptide of total HLA-DR/CII peptide complexes in the mixture or the composition. Further, the heterogeneous mixture of HLA-DR/CII peptide complexes comprises no more than 90%, no more than 80%, no more than 70%, no more than 60%, or no more than 50% unmodified CII peptides of total HLA-DR/CII peptide complexes in the mixture or the composition. Preferably, the heterogeneous mixture of HLA-DR/CII peptides complexes comprises separately or in addition less than 20%, less than 10%, less than 5% and more preferably less than 1% GG-Hyl in the CII peptide of total HLA-DR/CII peptide complexes in the mixture or the composition. Wherein the percentage refers to percent of CII peptide in the HLA-DR/CII peptide complexes of total CII peptides in the HLA-DR/CII peptide complexes. The second lysine residue (K270) may be mutated, for example mutated to Arginine (K270R). This avoids post-translational modification at this position of the CII peptide expressed as fusion protein with the HLA-DR protein and avoids possible interference with TCR binding. Preferably the (optional) second lysine is not post-translationally modified to glucosylgalactosyl-hydroxylysine (GG-Hyl) and is present as unmodified lysine, hydroxylysine or galactosyl hydroxylysine, preferably unmodified.

In order to reduce heterogeneity of the mixture of HLA-DR/CII peptides complexes and bulky glucosylgalactosyl-hydroxylysine formation it is further advantageous if the mammalian cell lacks galactosylhydroxylysyl glucosyltransferase (EC 2.4.1.66) activity. In one embodiment the mammalian cell therefore lacks galactosylhydroxylysyl glucosyltransferase activity. Preferably the mammalian cell lacks lysylhydroxylase 3 (LH3). LH3 is a multifunctional enzyme comprising lysylhydroxylase (LH), galactosyltransferase (GT) and galactosylhydroxylysyl glucosyltransferase (GGT) activity, wherein the major function of the enzyme seems to be the GGT activity. LH3 activity may be deleted or reduced using knock-down or knock-out approaches. Enzyme expression can, e.g., be reduced using RNA interference, such as siRNA or shRNA.

The term "RNA interference" (RNAi) refers to sequence-specific or gene-specific suppression of gene expression (protein synthesis), without generalized suppression of protein synthesis. RNAi may involve degradation of messenger RNA (mRNA) by an RNA-induced silencing complex (RISC), preventing translation of the transcribed mRNA. The suppression of gene expression caused by RNAi may be transient or it may be more stable, even permanent. RNAi may be mediated by miRNA, siRNA or shRNA. Preferably the RNAi according to the invention is gene-specific (only one gene is targeted). Gene-specific RNAi may be mediated by siRNA or shRNA.

As used herein, the terms "small interfering" or "short interfering RNA" or "siRNA" refer to an RNA duplex of nucleotides that is targeted to a desired gene and is capable of inhibiting the expression of a gene with which it shares homology. It is formed from long double stranded RNA (dsRNA) or shRNA. The RNA duplex typically comprises two complementary single-stranded RNAs of 19, 20, 21, 22, 23, 24, 25, 26, 27, 28 or 29 nucleotides that form 17, 18, 19, 20, 21, 22, 23, 24, 25, 26 or 27 base pairs and possess 3' overhangs of two nucleotides, preferably the RNA duplex comprises two complementary single stranded RNAs of 19-27 nucleotides that form 17-25 base pairs and possess 3' overhangs of two nucleotides. siRNA is "targeted" to a gene, wherein the nucleotide sequence of the duplex portion of the siRNA is complementary to a nucleotide sequence of the mRNA of the targeted gene. The siRNA or a precursor thereof is always exogenously introduced into the cell, e.g., directly or by transfection of a vector having a sequence encoding said siRNA, and the endogenous miRNA pathway is harnessed for correct processing of siRNA and cleavage or degradation of the target mRNA. The duplex RNA can be expressed in a cell from a single construct.

As used herein, the term "shRNA" (small hairpin RNA) refers to an RNA duplex wherein a portion of the siRNA is part of a hairpin structure (shRNA). The shRNA can be processed intracellularly into a functional siRNA. In addition to the duplex portion, the hairpin structure may contain a loop portion positioned between the two sequences that form the duplex. The loop can vary in length. In some embodiments the loop is 4, 5, 6, 7, 8, 9, 10, 11, 12, 13 or 14 nucleotides in length. The hairpin structure can also contain 3' or 5' overhang portions. In some aspects, the overhang is a 3' or a 5' overhang of 0, 1, 2, 3, 4 or 5 nucleotides in length. In one aspect of this invention, a nucleotide sequence comprised in the vector serves as a template for the expression of a small hairpin RNA, comprising a sense region, a loop region and an antisense region. Following expression the sense and antisense regions form a duplex. shRNA is always exogenously introduced, e.g., by transfection of a vector having a sequence encoding said shRNA, and the endogenous miRNA pathway is harnessed for correct processing of the siRNA and cleavage or degradation of the target mRNA. Use of a vector having a sequence encoding a shRNA has the advantage over use of chemically synthesized siRNA in that the suppression of the target gene is typically long-term and stable.

Typically, siRNA and shRNA mediate mRNA repression by complete sequence complementarity (i.e., perfect base paring between the antisense strand of the RNA duplex of the small interfering RNA and the target mRNA) and are therefore specific for their target. The antisense strand of the RNA duplex may also be referred to as active strand of the RNA duplex. Complete sequence complementarity of perfect base paring as used herein means that the antisense strand of the RNA duplex of the small interfering RNA has at least 89% sequence identity with the target mRNA for at least 15 continuous nucleotides, at least 16 continuous nucleotides, at least 17 continuous nucleotides, at least 18 continuous nucleotides and preferably at least 19 continuous nucleotides, or preferably at least 93% sequence identity with the target mRNA for at least 15 continuous nucleotides, at least 16 continuous nucleotides, at least 17 continuous nucleotides, at least 18 continuous nucleotides and preferably at least 19 continuous nucleotides. More preferably the antisense strand of the RNA duplex of the small interfering RNA has 100% sequence identity with the target mRNA for at least 15 continuous nucleotides, at least 16 continuous nucleotides, at least 17 continuous nucleotides, at least 18 continuous nucleotides and preferably at least 19 continuous nucleotides.

Alternatively, the enzyme is not expressed or the gene may be mutated or deleted. Thus, the mammalian cell lacks galactosylhydroxylysyl glucosyltransferase activity. In certain embodiments the mammalian cell lacks the multifunctional enzyme LH3. For example the gene may be silenced or not sufficiently expressed. In other certain embodiments the mammalian cell comprises a mutant LH3 enzyme lacking galactosylhydroxylysyl glucosyltransferase activity.

The mammalian cell may also be genetically engineered to have reduced or no galactosylhydroxylysyl glucosyltransferase activity. The PLOD3 gene encoding for LH3 may be mutated or deleted; and/or the LH3 enzyme may be a mutated LH3 enzyme lacking galactosylhydrosylysyl glucosyltransferase activity. Methods for deleting or mutating genes are well known in the art and may include the use of sequence specific DNA editing enzymes. A "sequence specific DNA editing enzyme" or a "site specific nuclease" as used herein is a protein that enables the cleavage of DNA at defined nucleotide sequences (recognition sites). Said cleavage may occur on one or both of two complementary DNA strands and thus allow, for example targeted mutagenesis, targeted deletion of specific genomic DNA sequences or result in the site-directed recombination of the cleaved target DNA with a heterologous polynucleotide. The sequence specificity of said editing enzymes may result from one or more sequence specific DNA binding protein domains within the editing enzyme, or from the enzyme binding a guide polynucleotide (e.g. guide RNA) that directs it to a DNA sequence with at least partial complementarity to said guide polynucleotide. The recognition site of said editing enzymes may therefore be altered by engineering the DNA binding protein domains, or using alternative guide polynucleotides. Multiple sequence specific DNA editing enzymes are known in the art, non-limiting examples of which are zinc finger nucleases (ZFNs), meganucleases, transcription activator-like effector nucleases (TALENs) and CRISPR associated nucleases.

Preferably the genetically engineered mammalian cell lacking galactosylhydroxylysyl glucosyltransferase activity is a HEK 293 cell or cell line. An example of a cell line that would benefit from reducing galactosylhydrosylysyl glucosyltransferase for the production of the HLA-DR/CII complexes is the Expi293F cell (Gibco, Cat. No. A14527, also available as cGMP banked Cat. No. 100044202). Galactosylhydroxylysyl glucosyltransferase activity may also be inhibited using carminic acid during cultivation.

The mammalian cells are preferably being established, adapted, and completely cultivated under serum free conditions, and optionally in media, which are free of any protein/peptide of animal origin. Commercially available media such as PreproGow™ HEK293 Media (PREPRO-TECH, USA) Expi293™ Expression Medium (Thermo Fisher, USA), HAM's F12 (Sigma, Deisenhofen, Germany,) RPPMI (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, CA), serum-free CHO Medium (Sigma), and protein-free CHO Medium (Sigma) are exemplary appropriate nutrient solutions. Any of the media may be supplemented as necessary with a variety of compounds, non-limiting examples of which are recombinant hormones and/or other recombinant growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics and trace elements. Any other necessary supplements may also be included at appropriate concentrations that would be known to those skilled in the art. For the growth and selection of genetically modified cells expressing a selectable gene a suitable selection agent is added to the culture medium.

EXAMPLES

Test Substances and Formulations

Aq/galCII or DR4/galCII (loaded with synthetic Gal-peptide: GIAGFK(Gal-Hyl) GEQGPKGEP) and Aq/nCII or DR4/nCII (loaded with non-modified peptide: GIAGFKGEQGPKGEP; SEQ ID NO: 13): Aq-mCLIPmt protein was expressed in HEK293 cell line (Expi293F cells, Gibco, Cat. No. A14527) or CHO cells (FIG. 4) by transient transfection, purified using a combination of immobilized metal ion affinity chromatography (IMAC) using the His-tag and size exclusion chromatography (SEC). Then, the covalently bound pre-peptide was replaced by thrombin cleavage and the addition of excess Gal-peptide or non-modified peptide. Finally, SEC was performed to remove cleaved pre-peptide and excess of Gal-peptide or non-modified peptide. Gal-peptide: GIAGFK(Gal-Hyl)GEQGPKGEP) were synthesized, purified, and characterized, as described in Diogo, D. et al., Curr Opin Rheumatol. 2014; 26:85-92; Gregersen P K et al., Arthritis Rheum. 1987; 30:1205-1213; Duke O et al., Clin Exp Immunol. 1982; 49:22-30.

Naturally glycosylated mouse Aq/rCII and human DR4/hCII: Naturally glycosylated mouse Aq/rCII and human DR4/hCII protein was expressed in HEK293 cell line (Expi293F cells, Gibco, Cat. No. A14527) by transient transfection and purified using a combination of immobilized metal ion affinity chromatography (IMAC) using the His-tag and size exclusion chromatography (SEC). For in vivo experiments, MHC II-peptide complexes were diluted to desired concentrations in sterile PBS (Gibco), filtered using a DynaGard 0.2 μm syringe tip filter and 100 μl protein solution was filled into ALZET micro-osmotic pumps (DU-RECT corporation, model 1007D, 0.5 μl/h, 7 days) using sterile techniques. The pumps were handled with surgical gloves. To ensure immediate pumping of the substance the prefilled pumps were placed in PBS overnight at 4° C. before implantation.

More specifically cDNAs encoding the two chains of the complex as depicted in FIG. 1 were synthesized at Eurofins with KpnI and XhoI restriction sites at the 5' and 3' ends. The synthesized cDNAs were digested using restriction enzymes KpnI and XhoI (FastDigest™, ThermoFisher Scientific). The digested DNA fragments were cloned separately into mammalian expression vector pCEP4 (Life technologies) following digestion with the same restriction enzymes. After sequence verification, the two recombinant plasmids encoding the two chains of the complex were co-transfected into Expi393F™ cells with FectoPRO™ DNA transfection reagent (Polyplus transfection). The supernatants were harvested 6 days post-transfection. The recombinant protein was first captured using a 5 ml HisTrap Excel (GE Healthcare Life Sciences) affinity column followed by size-exclusion chromatography on Superdex 200 pg (GE Healthcare life Sciences). The recombinant protein was purified as a single peak and was concentrated, diafiltrated into biotinylation buffer (20 mM Tris-HCl, 50 mM NaCl, pH 8.0) using an Amicon centrifuge device with MWCO of 10 kDa. Biotinylation using biotin-protein ligase was performed according to the manufacturer's instructions (Avidity), and the reaction was carried out at 30° C. for 2 h. Free biotin were removed by size-exclusion chromatography on a Superdex 200 pg column.

Animals

Male QB mice (B10.Q×BALB/c, n=9) F1, 12-16 week of age, were used in the experiments. The founders of the B10.Q mice were originally provided by J. Klein (Tübingen, Germany), and BALB/c mice were purchased from The Jackson Laboratory. All mice were bred and housed at the animal facility of Medical Inflammation Research (Karolinska Institute). All animals used were fed a standard rodent chow and given water ad libitum. Different experimental groups were housed together in order to minimize experimental bias. The local ethics committee approved all animal experiments (Stockholms Norra Djurförsöksetiska Nämnd, Stockholm, Sweden). All in vivo arthritis experiments were covered by the ethical numbers N213/14 and N35/16. Anesthesia of animals was accomplished by isoflurane inhalation, whereas sacrifice was performed with $CO_2$.

Induction and Clinical Evaluation of Arthritis

Rat type II collagen (rCII) was prepared from Swarm chondrosarcoma (Swarm rat chondosarcoma, SRC), by limited pepsin digestion, and further purification, as described in Chavele K M and Ehrenstein M R, FEBS Lett. 2011; 585:3603-10. Prepared rCII was stored at 4° C. until used. To induce collagen-induced arthritis (CIA), each mouse was injected with 100 μg of rCII emulsified 1:1 in CFA (Difco) at the base of the tail in a total volume of 100 μl. Thirty-five days later, the mice were given a booster injection of 50 μg of rat CII emulsified 1:1 in IFA (Difco) in a total volume of 50 μl. Development of clinical arthritis was followed through visual scoring of the animals based on the number of inflamed joints in each paw, starting 2 weeks post-immunization and continuing until the end of the experiment. An extended scoring protocol as described in Klareskog L et al., Annu Rev Immunol. 2008; 26:651-75 ranging from 1 to 15 for each paw with a maximum score of 60 per mouse was used. The mice were examined two to four times per week for 90 days following immunization.

Treatment Protocol

The ALZET micro-osmotic pumps diffusing either different amounts of naturally-glycosylated Aq/rCII (n=9) or PBS (control group, n=9) were implanted subcutaneously in QB mice on day 7 post-immunization. Sterile techniques were used during the surgical implantation procedure. For subcutaneous placement, a small incision was made into the skin between the scapulae, a small pocket was formed and the pumps were inserted into the pocket with the flow moderator pointing away from the incision. The skin incisions were closed using wound clips.

A single s.c. injection of 100 μg in mice was nearly equally effective on the treatment of clinical arthritis as the s.c. pump infusion of 15 μg/day for 7 consecutive days. However, the prolonged treatment seemed to be more effective on the induction of regulatory TR1 cells as evidence by FACS analysis of lymph node T cells in the treated mice.

DTH

QB mice pre-immunized with rat CII/CFA (rCII) were intradermally injected with 10 μg of rCII dissolved in phosphate buffered saline (PBS) into the left ear at day 8 post-immunization. For control the right ears were injected with solvent and the ear swellings measured 24 h later by an investigator blinded for the treatment of the animals using a caliper. Treatment was performed via a 24 h application of 100 µg of Aq/peptide complexes using osmotic pumps implanted at day 4 post immunization with rCII. Groups: Aq/mCLIPmt (n=6), Aq/galCII with (His, n=5) and without His-tag (w/o His, n=5).

T Cell Hybridoma Assay

MHC II/peptide complexes were diluted in sterile PBS and coated onto plates by incubation at 4° C. for overnight or added directly in soluble form to T cell hybridomas. The MHC II/peptide complex-coated plates were then washed twice with sterile PBS to remove unbound complexes, and $5 \times 10^4$ T-hybridoma cells in 200 µl DMEM supplemented with 5% FCS, 100 IU/ml penicillin, and 100 µg/ml streptomycin were added per well. T cell hybridoma 3H8 and mDR1.1 specific for GalOK264 and for nonmodified CII259-273 (K264), respectively, have been used. After 24 h, IL-2 or IL-10 (in some experiments) was measured in the culture supernatants by sandwich ELISA (BioLegend). Mouse rIL-2 or rl-10 respectively served as a positive control and standard.

Stimulation experiments using T-hydridoma cells were performed under different conditions in microtiter wells: 1) pre-coated with recombinant DR4/CII-peptide complexes, 2) coated with hyaluronan (Sigma Aldrich (#H7630)) or chondroitin sulfate (Sigma Aldrich (#C9819)) to which the DR4/CII-peptide complexes were subsequently added in fluid phase. This design was chosen to study the impact of the potential interaction of both components on T cell activation by the DR4/CII-peptide complex and mimics the interplay of the DR4/CII-peptide complexes with connective tissue components physiologically expressed in the extracellular matrix (ECM) in the tissues and the draining lymphatic system, or 3) with a blocked surface to which the solute ECM components hyaluronan, chondroitin sulfate or heparin sulfate as well as the DR4/CII-peptide complexes were added in order to study their impact on the T-hydridoma cells as a model for the modulation of T cell function in body fluids of diseased tissues compartments e.g. joint effusions or the lymph fluid.

Detection of Antigen Specific T Cells by MHC II Tetramer Staining

The MHC II/peptide tetramer complexes were freshly prepared by adding PE-labeled streptavidin and APC-labeled streptavidin (Biolegend) to the recombinant protein at a molar ratio of 1:4, and incubating at +4° C. for 1 h. To identify peptide-specific T lymphocytes, cells were incubated with the DR4/peptide tetramer complexes (20 µg/ml) at +37° C. for 1 h in the presence of 50 nM Dasatinib, a small-molecule protein tyrosine kinase inhibitor, following staining for cell surface markers. Viability staining solution (Zombie NIR; Biolegend) was added just before acquisition to exclude dead cells from the analysis. The samples were acquired by using an LSR Fortessa flow cytometer using FacsDiVa software (BD Biosciences), and the data were analyzed with FlowJo Software (v10, FlowJo LLC).

Activation of Human T Cells Upon CII Peptide Stimulation

PBMCs were thawed and rested overnight in TexMACS (Biolegend) at $1.5 \times 10^6$ cell/well. Cells were stimulated with the respective peptide variants GIAGFKGEQGPKGEP (SEQ ID NO: 13) and GIAGFK(Gal-Hyl) GEQGPKGEP) at a concentration of 50 µg/ml for 7 hours together with anti-CD28 at 1 µg/ml (BioLegend). For positive control and determination of CD154 assay sensitivity, staphylococcal enterotoxin B (SEB) was added to a separate culture at 1 µg/ml (Sigma-Aldrich). Following stimulation, cells were treated with LIVE/DEAD discrimination marker (BioLegend) and then stained for surface expression of CD3 and CD4, for positive gating and for CD19 for exclusion of B cells. Background levels were determined by unstimulated cells (treated with anti-CD28) and further subtracted from the CII-stimulated cultures. The samples were acquired by using an LSR Fortessa flow cytometer using FacsDiVa software (BD Biosciences), and the data were analyzed with FlowJo Software (v10, FlowJo LLC).

In Vitro Stimulation/Differentiation of T Cells from the Peripheral Blood of HLA-DRB1*0401-Positive RA Patients In vitro assays were performed to analyze the induction/differentiation of regulatory T cell functions e.g. the upregulation of the Tr1 phenotype associated cytokine IL-10 upon stimulation with DR4/CII-monomers for a prolonged incubation period of several days. Accordingly, PBMCs were isolated by dense gradient centrifugation and $1.2 \times 10^6$ cells/mL cells in TexMACS (MiltenyiBiotec, Cat #130-097-196) were stimulated with 1 µg/mL anti-CD3 (Biolegend, Cat #317304) and 100 ng/ml IL-27 (Peprotech, Cat #200-38B) (positive control, Tr1), 3.6 µg/mL DR4/nCII, 3.6 µg/mL DR4/galCII, 3.6 µg/mL DR4/hCII or left without stimulation (negative control, w/o) for 8 days. Stimulation was done in duplicates. At day 8 the culture supernatants were collected and analyzed for released cytokines using a custom made panel for detection of human cytokines in a multiplex bead-based LEGENDplex™ assay following the manufacture's protocol.

Results

Example 1: Production of Functionally Active Ag/rCII in HEK 293 Cells

It has been verified in previous experiments that two intravenous injections with Aq molecules loaded with synthetic galactosylated CII259-273 peptides can protect mice from development of arthritis. However, the synthesis of the galactosylated CII259-273 is both time- and cost consuming. In addition, the loading of the synthetic peptide to the recombinant MHC class II molecule is neither trivial nor cost efficient. Accordingly, it would be a significant advantage to establish a biosynthetic process allowing for the single step production of the MHCII molecule containing the covalently bound CII259-273 peptide (FIG. 1) fused to one of the MHC II chains in a host cell that ensures a proper posttranslational modification of the lysine side chain at position 264 in the CII-peptide by hydroxylation and subsequent galactosylation in situ. The posttranslational collagen peptide modifications however depend on the presence of the respective enzyme activities, i.e., lysyl hydroxylase activity and collagen beta galactosyltransferase activity. For example, E. coli-produced proteins do not normally display such modifications and while some insect cells have the capacity to hydroxylate lysine residues, they do not produce CII-peptides containing O-linked glycosylation of hydroxylysine. Moreover, it was unknown, whether a host cell providing the required enzyme activities would indeed be capable of providing the required modifications at the selective amino acid position of the CII-peptide within the frame of the non-collagenous MHCII protein sequence.

In the following it is shown for the first time that Aq/rCII (259-273) complexes can be expressed in HEK293 cells and that the purified complexes comprise covalently linked CII peptides (CII259-273) wherein the lysine at position 264 is post-translationally modified. We analysed type of modifications of the lysine side chains in the CII peptide and whether the purified in situ galactosylated Aq/rCII (259-273) complex are protective in a CIA mouse model in a similar manner as observed for recombinant Aq molecules loaded with galactosylated CII259-273 peptides. To test the therapeutic potential of HEK293-produced Aq/rCII (259-273) complexes we used osmotic pumps that have been implanted subcutaneously one week after immunization. Osmotic pumps are advantageous over intravenous injections, because Aq/rCII (259-273) complexes remain in the circulation at constant level and are available for tolerance induction in vivo over a longer period of time. When comparing three different types of pumps that releases their content over 24 hours, 7 days or 6 weeks, it was found that all three pumps mediate protection from arthritis when containing with Aq-molecules loaded with synthetic galactosylated CII-peptides (data not shown). However, using the pump with a sustained release for 7 days pumps was found to mediate protection more strongly associated with development of CII-specific T cells with regulatory capacity, compare to 24 hour pumps (data not shown). Without being bound by theory, a slow release rate at a low dose may result in the development of regulatory T cells whereas a faster release of a higher dose may result in depletion of pathogenic T cells. However, the observed difference could also be explained by the prolonged exposure, which increases the likelihood of CII-specific T cells-which would occur at low frequency—to interact with the Aq/rCII (259-273) complex before it is eliminated from the circulation. The experiments described below were done using osmotic pumps that release their content over 7 days.

In order to evaluate which posttranslational modifications were present when the Aq/rCII (259-273) complex was produced in HEK293 cells, Aq-restricted T cell hybridoma clones with different specificities for the CII259-273 epitope were stimulated in vitro with the purified complex (FIG. 2).

Control MHC II/CII complexes were produced in S2 insect cells, which have a strongly impaired capacity to produce posttranslational modifications in terms of O-linked glycosylation of lysine side chains. As expected, only the HCQ.4 clone, which recognizes the CII259-273 peptide with a non-modified or hydroxylated lysine at position 264, responded to the Aq/rCII (259-273) complex produced in S2 insect cells. In contrast, all CII-specific clones responded to the Aq/rCII (259-273) complex produced in HEK293 cells. Other specificities of the T cell hybridoma clones used are as follows: HCQ3 (CII, Gal-HK264), HCQ.4 (CII, not modified and HK264), HCQ.11 (Glc-Gal-HK264), HM1R.2 (CII, Gal-HK264 and Gal-HK264+270), HP3 (Aq-restricted, pepsin-peptide). This shows that position 264 can indeed become post-translationally modified when produced in HEK293 cells. Furthermore, the resulting complex is heterogenous where position 264 includes non-modified and/or hydroxylated lysine as well as glycosylated lysines with both mono- and disaccharides. The Aq-restricted clone HP3, which is specific for a pepsin-peptide did not respond to any of the Aq/rCII (259-273) complexes.

Example 2: In Situ Glycosylated Ag/rCII in a Mouse CIA Model

Figure 3:
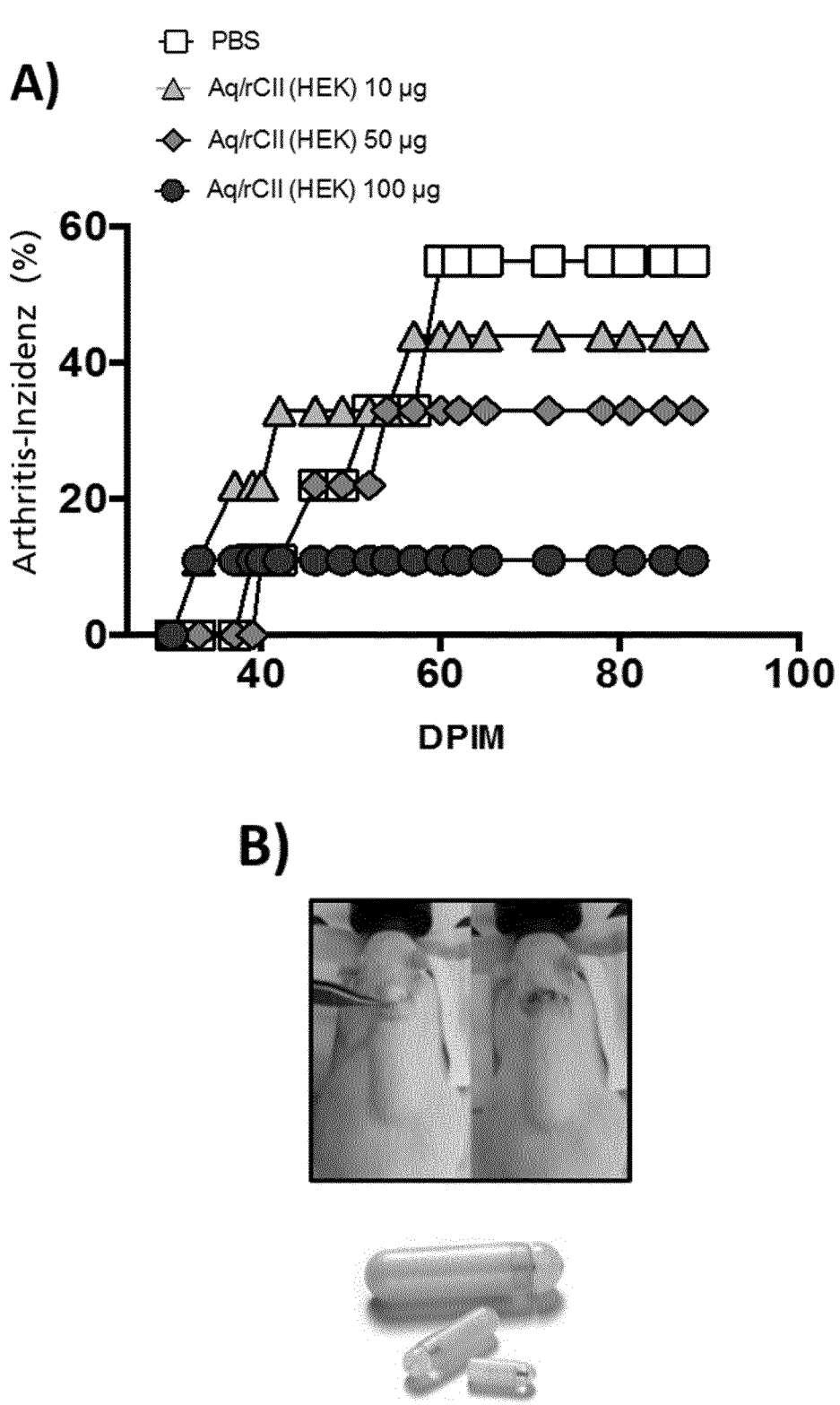
FIG. 3: Therapeutic vaccination using in situ glycosylated Aq/rCII produced in HEK 293 cells in a mouse CIA model. A) dose-response-curve: Naive mice were immunized with CII to induce arthritis and received a boost immunization at day 35. Mice were treated with different dosages of the HLA-DR/CII peptide complex: 10, 50 or 100 μg (n=9). The number of arthritic mice is significantly lower in the 100 μg treatment group compared to control (p<0.05, chi-square). B) To administer the HLA-DR/CIIpeptide complex osmotic pumps were implanted 7 days following boost immunization at day 35 to ensure a continually administration of the vaccine (e.g. 100 μg: 15 μg/24h for 7 days).

Mice immunized with CII in adjuvants were implanted 7 day later (following boost immunization 35 days after the initial immunization) with osmotic pumps loaded with three different amounts of HEK293-produced Aq-rCII (259-273) complex and followed for development of arthritis. Mice were implanted with pumps loaded with PBS only as negative control. As shown in FIG. 3A, Aq-rCII (259-273) complex conferred protection in a dose dependent manner and mice treated with the highest amount of Aq-rCII (259-273) complex (100 µg) completely protected from developing arthritis. Mice treated with the intermediate amount (50 µg) of the Aq-rCII (259-273) complex showed some protection, whereas treatment with the lowest amount (10 µg) resulted in a frequency of arthritis that was comparable to PBS-treated controls.

Example 3: Production of Functionally Active DR4/hCII in HEK 293 Cells

We have proven that functional mouse MHCII/CII complexes (Aq/rCII) can be prepared in HEK293 cells using the in situ glycosylation machinery of the host cell. We next investigated whether human MHCII/CII complexes can be prepared in HEK293 cells using the in situ glycosylation machinery of the cell. The complexes were prepared as described above in HEK293 cells. Control complexes were expressed in CHO cells and loaded with not modified peptide (DR4/nCII) or galactosylated peptide (DR4/galCII). Two activation restricted human T cell hybridomas (3H8: unmodified CII-epitope, mDR1.1: galactosylated CII-epitope) were used to check the galactosylation status of the naturally glycosylated DR4/peptide complex (DR4/hCII) compared a DR4/peptide complex loaded either with not modified peptide or galactosylated peptide. As shown in FIG. 4A, the T cell hybridoma mDR1.1 gets activated upon stimulation with the DR4/galCII complex, whereas stimulation with the DR4/nCII remains almost negative. In comparison to the DR4/galCII and DR4/nCII, the DR4/covalently linked CII (DR4/hCII) is a heterogeneous product with regard to the galactosylation status. That means the composition comprising the DR4/hCII complex contains peptides with galactosylated and unmodified lysine residues in position 264. Activation level of cells stimulated with the DR4/hCII is slightly lower compared to the DR4/galCII complex and very similar to the DR4/nCII complex (FIG. 4B, using 3H8 cells).

Example 4: Detecting CII Peptide Specific T Cells in Humans

The aim was to establish a tetramer based method to directly detect antigen specific T cells in the peripheral blood (PBMCs) of RA patients and healthy donors. Therefore, biotinylated DR4/CII peptide complexes were incubated with either Streptavidin-PE or Streptavidin-APC. To reduce unspecific binding of the tetramers, a double tetramer staining by using two flurochromes was performed. Antigen specific T cells (CII259-273, K264 gal) using DR4/galCII tetramers can be detected in RA-patients as well as in healthy donors (FIG. 5A). Moreover, T cells with specificity for the unmodified CII peptide can be detected using DR4/nCII tetramers (FIG. 5B). The mean frequency of antigen specific T cells is higher using the naturally glycosylated DR4/hCII tetramers compared to DR4/galCII tetramers or DR4/nCII tetramers (FIG. 5B). Since the frequency of antigen-specific T cells in the peripheral blood is quite low (0.01-0.1%), the observed numbers are as expected.

Figure 6:
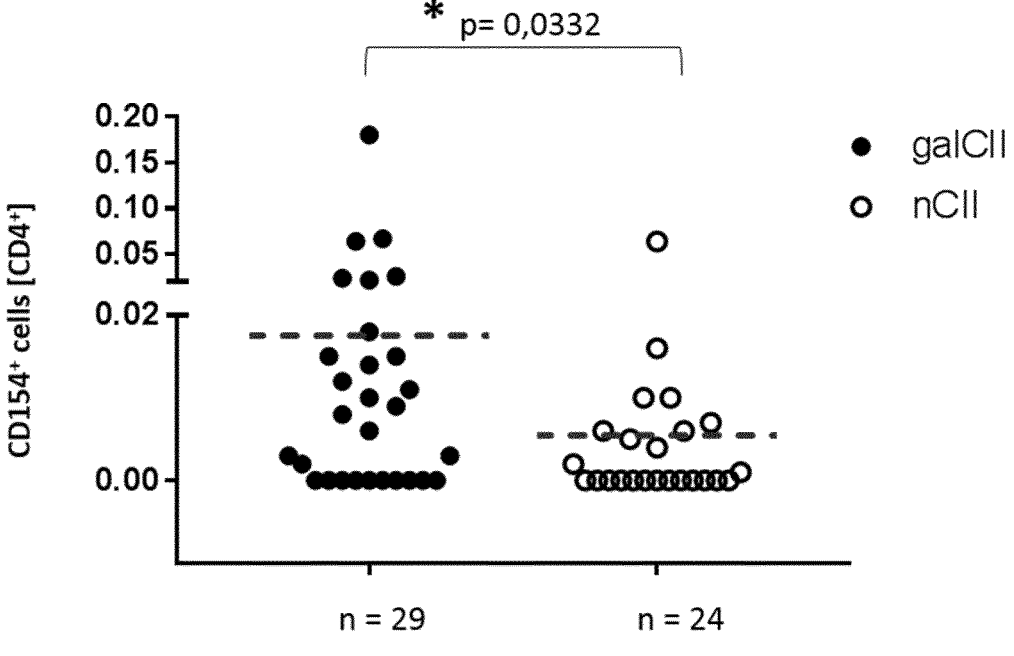
FIG. 6: Human T cell activation. Detection of antigen specific T cells in the peripheral blood of HLA-DRB1*0401 RA patients. T cells get activated upon galCII and to a lesser extent by non-modified CII peptide stimulation. The upregulation of CD154 was measured by flow cytometry (significance: p-Value=0.0332, Mann-Whitney-Test).

Activated CD4+ T cells were also detected in PBMCs of HLA-DRB1*0401 RA patients following galCII peptide stimulation by flow cytometry using CD154 (CD40L) surface staining as a marker for T cell activation (FIG. 6). As a positive control cells were also incubated with superantigen SEB, leading to strong upregulation of the activation marker CD154 (data not shown). In contrast, cells incubated only with an antibody against costimulatory CD28 were mainly negative (data not shown). Since the expected frequency of the antigen-specific T cell population is quite low in the peripheral blood, the detection of 0.01-0.1% CD154+ T cells (parent population: CD3/CD4 living T cells) is satisfying. Remarkable is the fact that T cells get less activated using the unmodified (naked) CII peptide. Since numbers of antigen specific T cells using DR4/galCII or DR4/nCII tetramer staining were similar in PBMCs of HLA-DRB1*0401 RA patients (FIG. 5), the difference observed following peptide activation seems to be due to a difference in activity or functional status of the respective T cells.

Example 5: In Vitro Stimulation/Differentiation of T Cells from the Peripheral Blood of HLA-DRB1*0401 Positive RA Patients In vitro studies were performed to investigate the induction/differentiation of regulatory T cell functions e.g. the upregulation of the Tr1 phenotype associated cytokine IL-10 upon stimulation with DR4/CII-monomers for a prolonged incubation period of eight days. Accordingly, isolated PBMCs from genotyped HLA-DRB1*0401 positive RA patients were either stimulated under Tr1 cell inducing conditions with anti-CD3 and IL-27 (positive control, Tr1), with DR4/nCII (3.6 µg/mL), DR4/galCII, (3.6 µg/mL), or without stimulation (negative control, K1) for 8 days. Stimulation was done in duplicates. At day 8 the culture supernatants were collected and analyzed for cytokine release using a custom-made panel for human cytokines in a multiplex bead-based LEGENDplex™ assay format according the manufacture's protocol. The results shown in FIG. 7 clearly demonstrate the capacity of DR4/nCII and DR4/galCII to induce the release of the anti-inflammatory cytokine IL-10 in PBMCs from RA patients and at levels even slightly higher compared to positive controls incubated under conventional TR1 inducing conditions for 8 days. There is no evidence for a concomitant activation of pathways leading to an increased production of pro-inflammatory cytokines e.g. TNF-α, IL-2, IL-17a, IL-17f, or IFN-γ.

Example 6: The His-Tag in the DR4/CII Peptide Complex: Contribution to the Pharmacological Effect It has been investigated whether sequences not directly essential for the MHCII/CII complex can be omitted from the construct, including the contribution of the polyhistidine-tag (His-tag), the biotinylation site, the TEV cleavage site, the thrombin cleavage site and the strep-tag to the T cell activating properties of the recombinant complex. Typically the DR4/CII peptide complexes as well as the anti-CD3 antibody (positive control) are coated to the plastic surface of the microtiter wells in a standard hybridoma activation assay. In initial experiments we used the internal TEV-cleavage site of the DR4/nCII peptide complex to investigate the effect of proteolytic cleavage of the His-tag on activation of T-hybridoma cells (3H8) measured by IL-2 secretion in comparison to the uncleaved DR4/hCII peptide complex coated to microtiter wells. Efficacy of proteolytic cleavage was controlled by Western Blot analysis. Further, equivalent coating efficacy of the microtiter wells using equimolar solutions of the cleaved and uncleaved complex was confirmed by ELISA using a DR4-specific antibody and a peroxidase-coupled secondary antibody (FIG. 8). This also confirms that the complex did not dissociate and is present as a heterodimer. Our data show a strong decrease of the cleaved construct in activating the T hybridoma cells although the functional domain of the DR4/nCII complex recognized by the TCR of the T hybridoma cells is coated with a similar efficacy to the plastic surface (FIG. 8). It is highly unlikely that the zipper cleavage lead to a dissociation of the complex. The zipper is primarily needed for the formation of the complex during the biosynthetic process, whereas the formed MHC II-peptide-complex itself is rather stable at least in vitro due to the stabilizing effect of the peptide bound to the binding groove formed by the variable regions of both chains.

Figure 9:
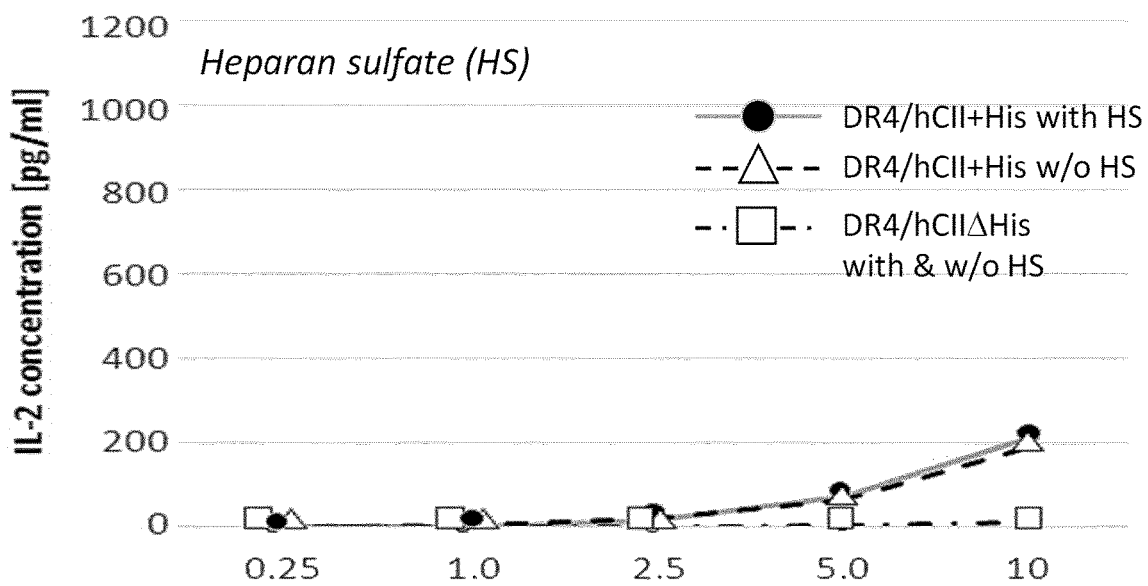
FIG. 9: Impact of the His-Tag in DR4/hCII peptide complexes and their interaction with A) chondroitin sulfate (CS) B) hyaluronan C) heparan sulfate (HS) on T cell activation: Induction of an IL-2 response in 3H8 hybridoma cells by DR4/hCII vs. DR4/hCIIΔHis and in (A) also DR4/hCII_DED at the concentrations indicated in solute phase in microtiter wells either blocked or precoated with chondroitin sulfate. Shown are IL-2 concentrations in the supernatant following activation.

We concluded that the His-tag in the uncleaved DR4/nCII complex is required for the correct orientation of the complex on the surface in a multimerized alignment exposing the peptide binding groove towards the T cell by preferentially contacting charged contact areas on the plastic surface. To confirm this conclusion, DR4/hCIIΔHis complex was produced that only lacks the His-tag (6×His) at the carboxy-terminal end of the MHC class II beta chain, but is otherwise identical to the DR4/hCII complex, i.e., contains the JUN/FOS heterodimerization domains (compare FIG. 1). As an additional control for the involvement of electrostatic interactions by the positively charged functional imidazole group of histidine, a further mutated recombinant variant of the DR4/hCII complex was prepared, in which the His-tag was replaced with a triplet of negatively charged amino acid residues Asp-Glu-Asp (DED) (DR4/hCII_DED). Also, we exchanged the unphysiological material plastic with charged extracellular matrix (ECM) components (chondroitin sulfate, heparin sulfate, hyaluronan) present on cell surfaces, in extracellular body fluids such as synovial effusions or the lymph as well as in tissues, such as joint cartilage or synovial membranes. For this purpose we first coated microtiter wells with highly concentrated solutions of chondroitin sulfat, heparin sulfate and hyaluronan solutions (10 mg/ml). The coated surfaces were washed thoroughly and in vitro stimulation experiments of 3H8 hybridoma cells were performed by adding the DR4/CII peptide complexes to the fluid phase using IL-2 concentrations in the supernatant as a read-out. For control, parallel experiments were performed in microtiter plates with blocked surfaces in the absence of the ECM-components. The results shown in FIG. 9A demonstrate that under these conditions only the complex containing the His-tag induced a strongIL-2 response and that its ability to activate T cells seems to be critical dependent on chondroitin sulfate coated to the surface of the microtiter wells, whereas the impact of hyaluronan (HA) remained less pronounced (Fib. 9B) and hardly detectable for heparin sulfate (FIG. 9C). The soluble DR4/hCII_DED control complex did not induce an IL-2 response in the presence of chondroitin sulfate coated surface of microtiter wells (FIG. 9A). However, the observed effect of the His-tagged complexes cannot simply be explained by electrostatic interactions of polysufated anionic glycosaminoglycans via the positively charged imidazole groups of the polyhistidine tag, since heparan sulfate likewise contains a high degree of negatively charged sulfate groups, but does not seem to significantly facilitate the IL-2 response of the 3H8 hybridoma cells stimulated by the solute His-tagged DR4/hCII complex. Accordingly, the results suggest a specific interaction of the polyhistidin tag with the chondroitin sulfate matrix to increase the IL-2 response by 3H8 hybridoma cells stimulated with the dissolved DR4/hCII complex.

Figure 10:
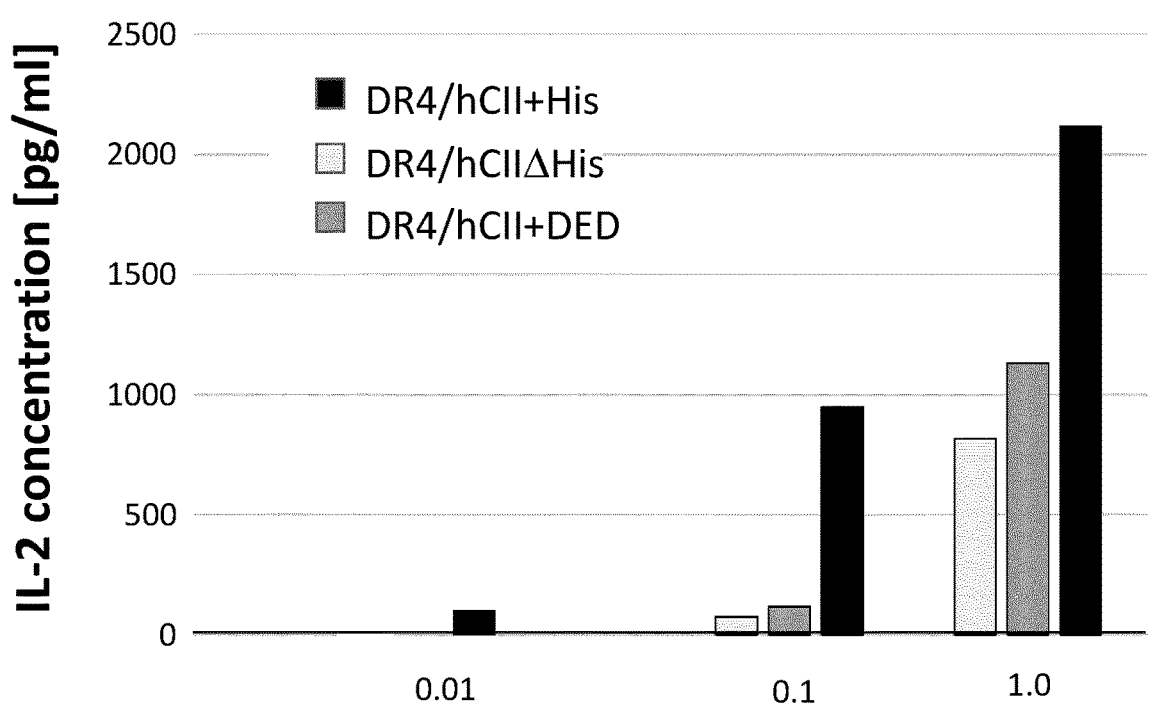
FIG. 10: Activation of 3H8 hybridoma cell by DR4/hCII vs. DR4/hCIIΔHis vs. DR4/hCII_DED precoated to microtiter wells at the concentrations indicated. Shown are IL-2 concentrations in the supernatant following activation at the indicated protein concentration of the DR4/nCII solutions used for coating to the microtiter plates [μg/ml].

In parallel T hydridoma cell stimulation experiments using direct coating of the different DR4/hCII constructs to the plastic surfaces at three different concentrations (0.01 mg/ml, 0.1 mg/ml and 1 mg/ml), the initial results obtained with the Tev-cleaved DR4/nCII complexes were confirmed. The capacity to induce an IL-2 response by the DR4/hCIIΔHis complex as well as the mutated DR4/hCII_DED complex is strongly reduced using 0.1 mg/ml and 1 mg/ml for coating. However, a response was observed using 1 mg/ml for coating at a level comparable to the unmodified complex (DR4/hCII) at a 10-fold lower coating concentration (FIG. 10).

Figure 11:
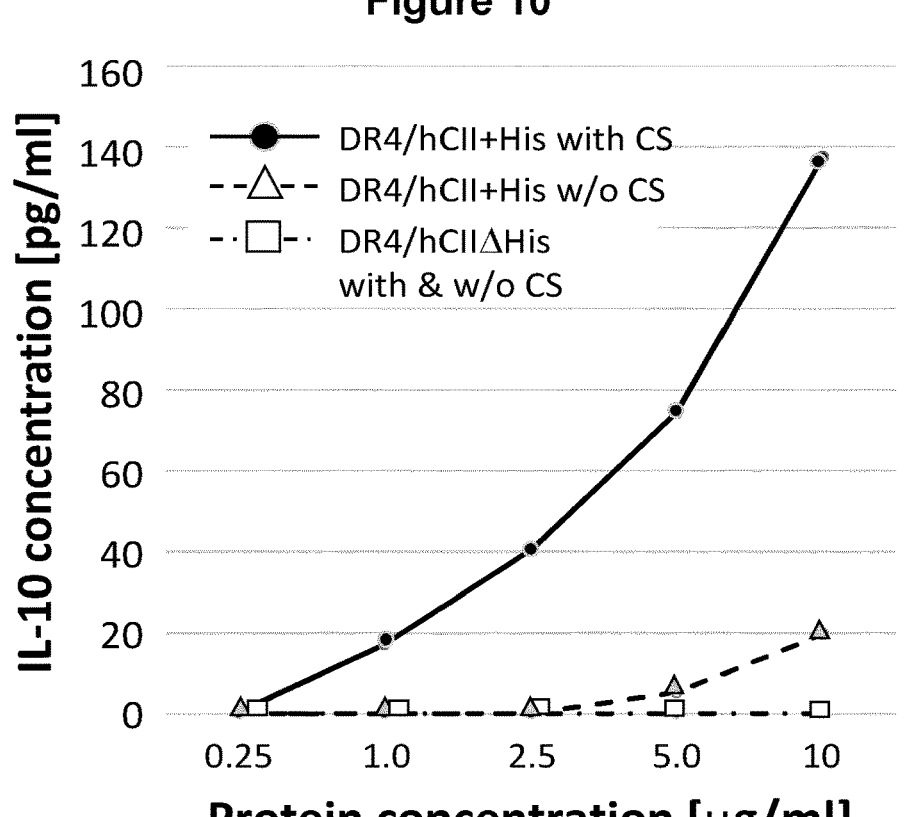
FIG. 11: Impact of the His-Tag in DR4/hCII peptide complexes and their interaction with chondroitin sulfate (CS) in solute phase to stimulate an IL-10 responses in 3H8 hybridoma cells: Activation of 3H8 hybridoma cells by DR4/nCII at the concentrations indicated in a solute phase with or without (w/o) chondroitin sulfate (2.5 mg/ml) in microtiter wells with a blocked plastic surface. Shown are IL-10 concentrations in the supernatant following activation at the indicated protein concentration of the DR4/nCII solutions used for coating to the microtiter plates [μg/ml].

However, the experiments also demonstrate that all constructs harbor the functional peptide in the DR4-binding groove as a requirement for TCR activation of the 3H8 hybridoma cells. Accordingly, our studies provide unequivocal evidence that the His-tag in the DR4/CII complex improves activity of the complex. Without being bound by theory, the His-tag seems to provide an improved spatial orientation of the peptide binding groove for TCR recognition via an impact on the interaction with the ECM component chondroitin sulfate. In addition, subsequent studies shown in FIG. 11 demonstrate that the interaction of the DR4/CII complex comprising a His-tag with chondroitin sulfate or with hyaluronan in the solid phase in a microtiter well with blocked plastic surfaces can enhance its capacity to stimulate an IL-10 response by the T hybridoma cells.

Figure 12:
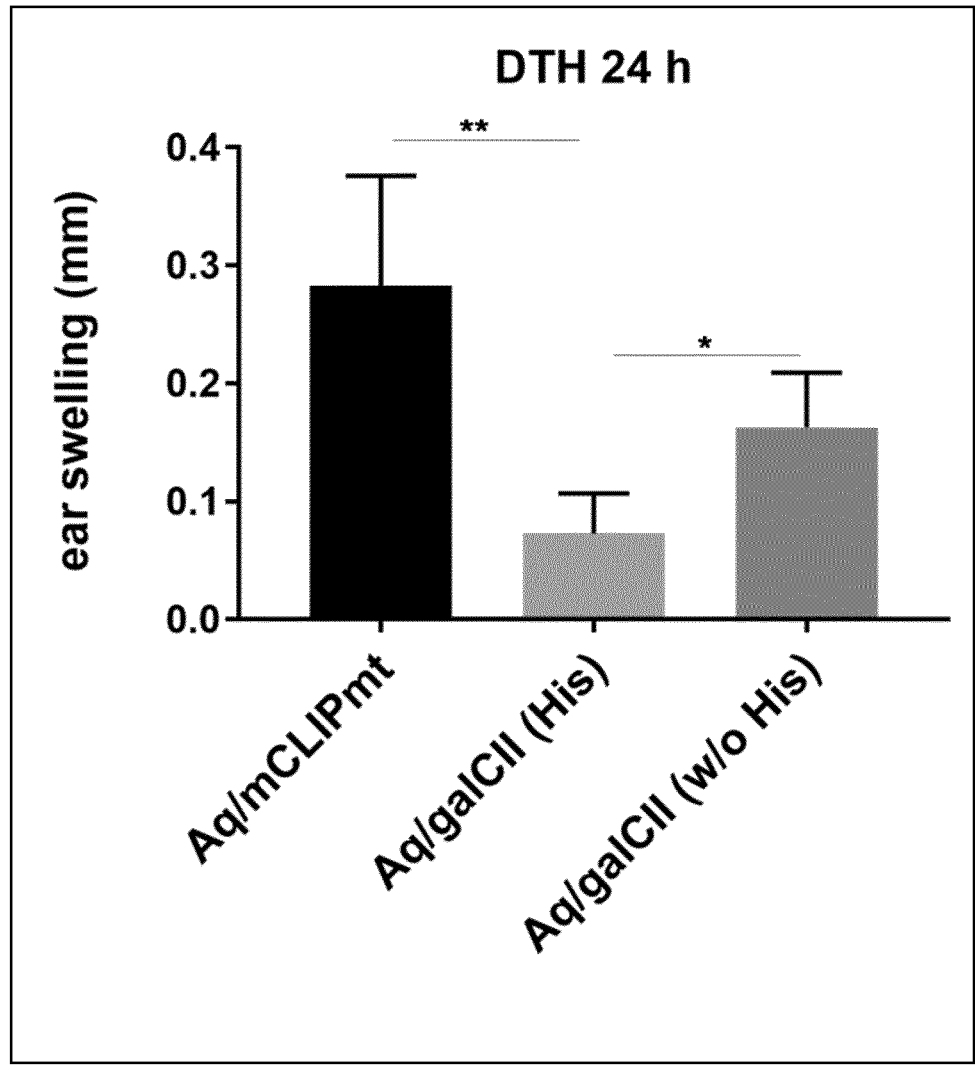
FIG. 12: Comparison of the therapeutic effect of Aq/galCII peptide complex either containing or lacking a His-tag on ear swelling induced by the DTH reaction to collagen II in vivo. The effect of the Aq/galCII construct with (His) and without the polyhistidine tag (w/o His) are shown in comparison to an Aq/mCLIPmt control construct containing a linked mouse mutated CLIP peptide in its binding groove (CLIPmt)(* indicates a p value of <0.05 and ** indicates a p value of <0.01).

The in vitro data support a critical functional role of the His-tag in the DR4/CII complex for its immunomodulatory pharmacological effect. Furthermore an in vivo study using the model of the T cell dependent CII-induced hypersensitivity reaction in Aq expressing QB mice was performed. CII-preimmunized mice were triggered at day 8 post immunization by an intradermal CII injection into one ear to develop a T cell dependent inflammatory swelling controlled by a vehicle trigger applied to the contralateral ear. Prior the induction of the DTH reaction the mice received treatment on day 4 postimmunization by a 24 h sc. pump-infusion of either a His-tag containing Aq/galCII complex, an Aq/galCIIΔHis complex lacking the His-tag or a control Aq/CLIP complex containing a linked control peptide [class II associated invariant chain: CLIP] in its binding groove. The results shown in FIG. 12 provide clear evidence for the functional impact of the His-tag on the therapeutic reduction of the T cell dependent ear swelling induced by the experimental CII-specific DTH-reaction. Thus, our studies consistently demonstrate an improved function of the MHCII/CII peptide complexes comprising a polyhistidine sequence for the immunomodulatory therapeutic effect on T cells, which is most likely mediated via its impact on the interaction with ECM components that are abundantly available in the context of targeted structures on cell surfaces, tissue components and body fluids in vivo.

Figure 13:
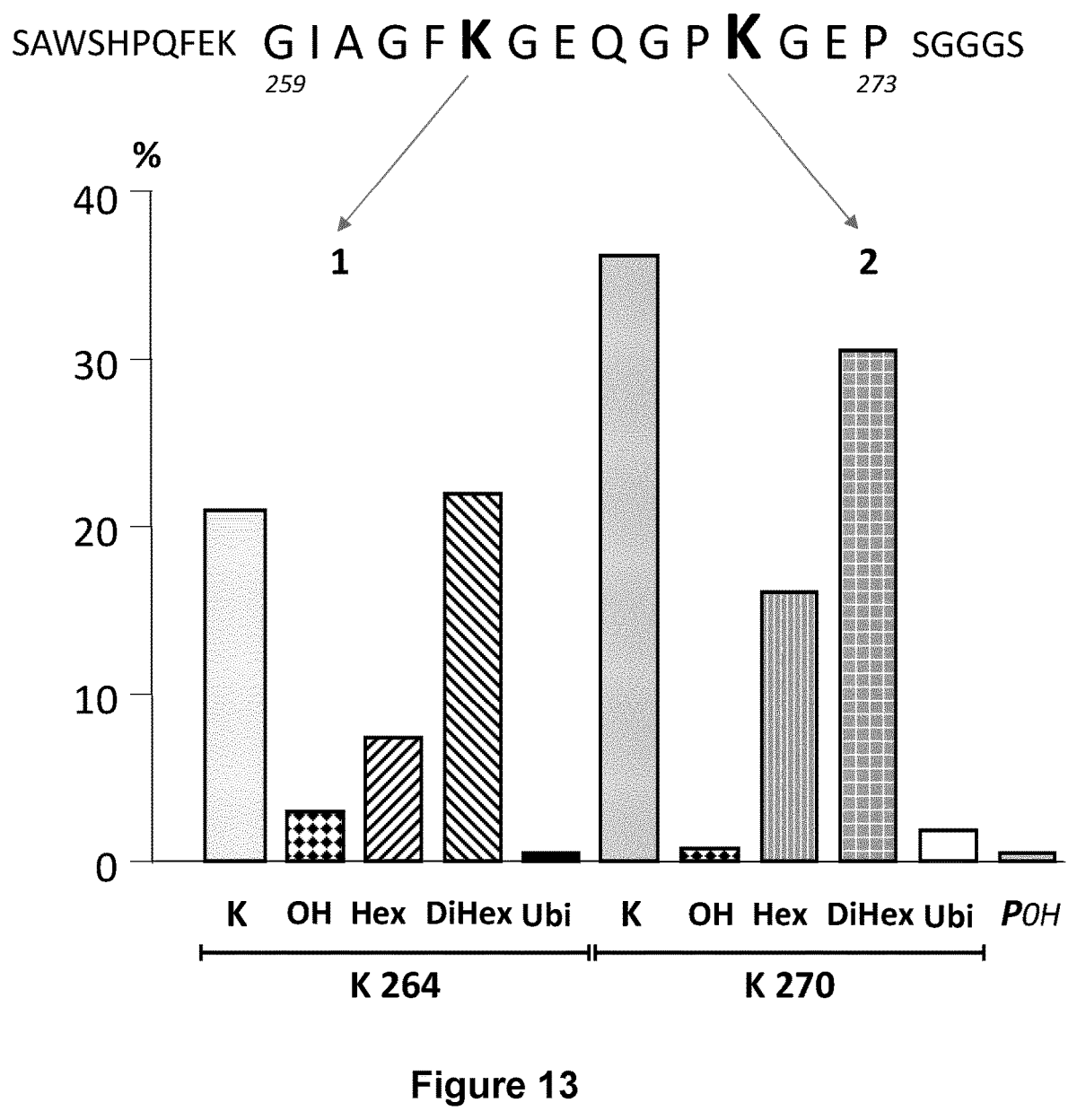

Example 7: Obstacles of the Recombinant Production of the DR4/Gal CII Complex in HEK Cells The posttranslational modification of the CII sequence of the peptide in the binding groove of the recombinant DR4-complex involves several sequential steps by different enzymes. These collagen-specific posttranslational modifications preferentially affect the lysine residues at positions 264 and 270. The initial step is a lysyl hydroxylation mediated by a lysyl hydroxylase followed by a galactosyl transfer to the hydroxylated lysine mediated by a galactosyl transferase. Further, a single glucose residue may be added to the galactosylated hydroxylysine. All these steps occur during the biosynthetic process in cells with a post-translational machinery for collagen, such as in HEK cells, thereby leading to a heterogenous recombinant product comparable to the natural ECM-protein in cartilage in vivo. In humans, this mixture is likely advantageous for the purpose of increasing the spectrum of potential T cells that can be recruited from the entire repertoire for modulation into regulatory cells to produce anti-inflammatory mediators such as IL-10 to dampen the immune-mediated joint disease. The studies on the in vitro activation of IL-2 and IL-10 responses in T cells from peripheral blood of RA patients in response to recombinant DR4/CII complexes either containing the galactosylated (DR4/galCII) or the non-modified CII (DR4/nCII) peptide provide experimental support in this direction. However, mass spectrometric analysis of several batches of CR4/hCII produced in HEK cells revealed that a considerable amount of the recombinant proteins exhibit a high degree of disaccharide (Glc-Gal-Hyl) content at both lysine residues (FIG. 13), which is likely to be disadvantageous for TCR recognition due to the coverage of the peptide binding groove by bulky carbohydrate structures thereby disturbing TCR recognition.

The collagen specific post-translational galactosylation of the lysine residues in the CII peptide sequence of the recombinant DR4/hCII constructs especially that at the residue 264 is important for T cell recognition via the TCR and the resulting pharmacological effects. As the lysine residue in position 270 is located at the edge of the binding groove of the DR4 molecule its carbohydrate modification is generally considered not to be involved in TCR recognition. In order to reduce heterogeneity and the potential risk for negative interference with TCR-recognition of the CII-peptide in the DR4 binding groove by the carbohydrate attachment to a hydroxylated lysine residue in position 270 (K270), K270 may be mutated into an arginine residue (R). This mutation has previously been shown not to affect binding to the TCR of antigen-specific T cell hybridoma.

Figure 14:
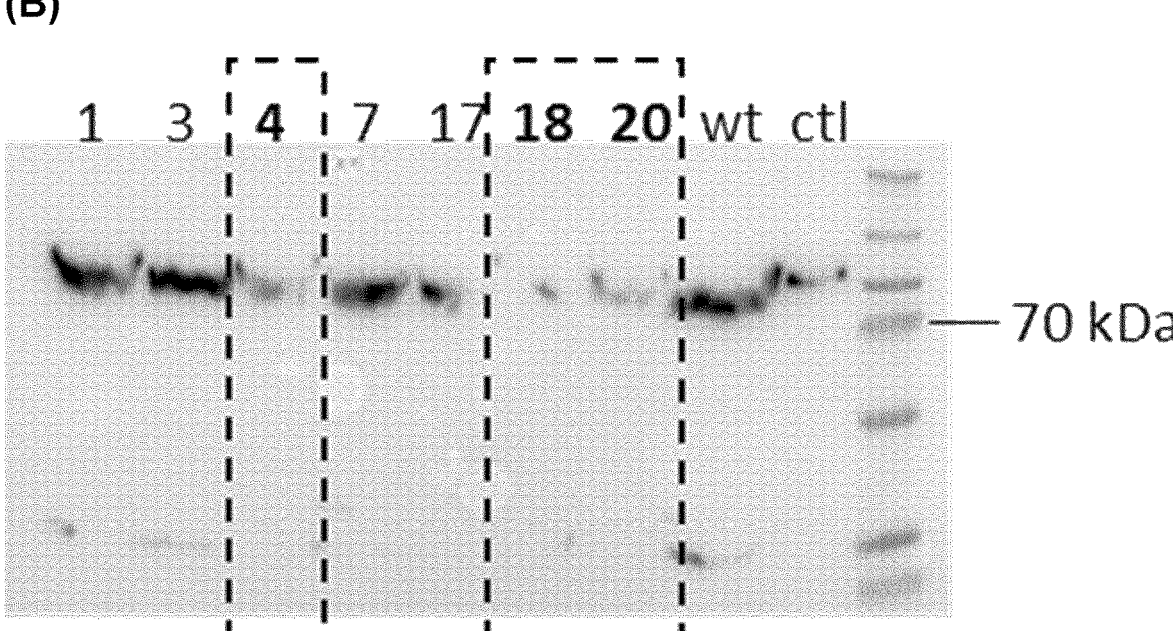
FIG. 14: Generation of Plod3 gene (LH3) knock-down Expi293 cell. (A) Schematic representation of the stepwise transfer from lysine to hydroxylysine to Gal-hydroxylysine and Glc-Gal hydroxyl mediated by the multifunctional collagen-modifying enzyme LH3. (B) Detection of PLOD3 by Western Blot. Lysates from different Expi293 HEK cell clones transduced with $1\times10^6$ lentiviral encoding Plod3 specific sh-RNA were loaded onto a SDS-PAGE and PLOD3 was detected on a Western Blot using an anti-PLOD3 antibody. PLOD3 has a theoretical molecular weight of 84 kDa. Clones #4, #18 and #20 were used for further expansion. (C) Glycan analysis by mass spectrometry. After lentiviral transduction with shRNA to knock-down the plod3 gene, a glycan analysis by mass spectrometry was performed to investigate the reduction of glucosylation of galactosylhydroxylysyl residues. Both lysines (K264 and K270) within the collagen type II epitope (SEQ ID NO: 1) shown at the top were analysed. A clear reduction of gluco-galactosylhydroxylysyl residues (DiHex) is demonstrated. Unmod=unmodified, OH=hydroxylated, DiOH=dihydroxylated, Hex=galactosylatedhydroxylysyl, DiHex=gluco-galactosylhydroxylysyl.

Even more relevant is the prevention of the final transfer of a glucose residue to the galactosylated hydroxylysine in position 264. This carbohydrate moiety is likely to have a negative effect on TCR recognition as the bulky and flexible disaccharide (Glc-Gal) may interfere with the TCR binding. In vitro stimulation of T cells from peripheral blood of RA patients have shown that the unmodified (nCII) as well as the monogalactosylated peptide (galCII) can be recognized. The reaction catalyzing the transfer of the glucose residue to the galactosylatedhydoxylysine is the galactosylhydroxylysyl glucosyltransferase (synonymous name: procollagen lysyl-hydroylase 3 (LH3)). LH3 is a multifunctional enzyme also capable of catalyzing the before mentioned initial steps of lysine modification, i.e., hydroxylation resulting in hydroxylysine (Hyl) and galactosyl transfer resulting in galactosyl-hydroxylysine (Gal-Hyl) (FIG. 14A). However, its non-redundant activity is the final glucose transfer to the galactosyl hydroxylysine.

We therefore genetically engineered Expi293F cells to knock-down the LH3 enzyme. A HEK cell line for the production of the DR4/hCII complex that is selectively made deficient for the final glucosyl transfer to the galactosyl hydroxylysine in the CII peptide is expected to be advantageous in order to improve efficacy of recombinantly produced DR4/hCII complex. This can be achieved by generating HEK293 LH3 knock-out cells, e.g., by introducing a gene disrupting mutation into the plod3 gene encoding the lysylhydroxylase 3 gene using a CRISPR/CAS gene editing approach.

In a first step we generated Expi293F cells with a plod3 knockdown by lentiviral transfection of specific shRNA to investigate the potential of this strategy to obtain a less heterogenous product with an increased specific T cell activating activity by improvement of the recombinant expression system. For transduction Expi293 cells were plated using 200,000 cells/well in 12-well plates followed by shaking the plates at 37° C., 8% $CO_2$ and 120 rpm for 3 hours. 200 uL lentiviral particles (customized lentiviral particles from Sigma) were mixed with 10 uL PElpro transfection reagent (Polyplus) and add to the cells and incubated for another 4 h under shaking at 37° C., 120 rpm and 8% $CO_2$, 1 mL fresh media was added and continued to incubate for 3 days before analyzing transduction efficiency.

Three days after lentivirus transduction with shRNA targeting Plod3, the cells were divided into two parts. To one-part puromycin was added to a final concentration of 2 μg/mL to kill the untransduced cells and the other part was analysed by flow cytometry to check the transduction efficiency. The cells were under antibiotic selection pressure until non-transduced cells were dead and the transduced cells divided for about 18 days to a viability above 90%. These stable transduced mixed pools were expanded to 500 mL and transfected with DR4/hCII as described above. After purification, glycan analysis by mass spectrometry was performed to investigate the reduction of glucosylation of galactosylhydroxylysyl residues in plod3 knock-down Expi293F cells and Expi293F control cells. Both lysines (K264 and K270) within the collagen type II epitope were analysed. A clear reduction of gluco-galactosylhydroxylysyl residues (DiHex) is visible in Expi293 KO cells (FIG. 14C).

Meanwhile, stably transduced cells were diluted and seeded on 96-well plates for mini pool generation. In the process of seeding, the cells were grown under selection pressure and 40 mini pools were isolated. The cells were expanded and PLOD3 expression was determined in cell lysates by Western Blot to verify efficient knock-down of Plod3. Lysates from $1\times10^6$ lentiviral transduced Expi293F mini pools were loaded onto a SDS-PAGE. Western Blot analysis of successful knock-down was performed using an anti-PLOD3 antibody (Thermo Fisher PA5-48435) and a secondary anti-rabbit HRP antibody. PLOD3 has a theoretical molecular weight of 84 kDa. Clone #4, #18 and #20 showed efficient Plod3 knock-down and were therefore used for further expansion and experiments. Clone 18 was lost due to drop in viability, Clones 4 and 20 have been selected for further production and glycan analysis is underway.

Example 8: Ag/Gal264 CII Constructs with Alternative Positively Charged Amino Acid-Tags at the C-Terminus of the Sequence Containing the β-Chain As shown above the His-tag in the DR4/nCII complex seems to allow correct orientation of the complex on the surface in a multimerized alignment exposing the peptide binding groove towards the T cell and a beneficial effect of the His-tag has been confirmed in vivo in a DTH model. We therefore searched for alternative tags that mediate a similar effect. The basic consideration for the search was that 6×His-sequence used in the construct is a non-natural structure and we therefore searched of sequences in human self-proteins that could replace the His-tag in immune-modulatory MHCII/CII peptide complexes. Thus, the His-tag replacement by a functionally equipotent self-structure aims at reducing a potential immunogenicity. Among the candidate self-proteins with a relative high content of functionally relevant basic amino acid residues and an evolutionarily conserved structure rendering autoimmune recognition less likely were proteins of the histone family.

Figure 16:
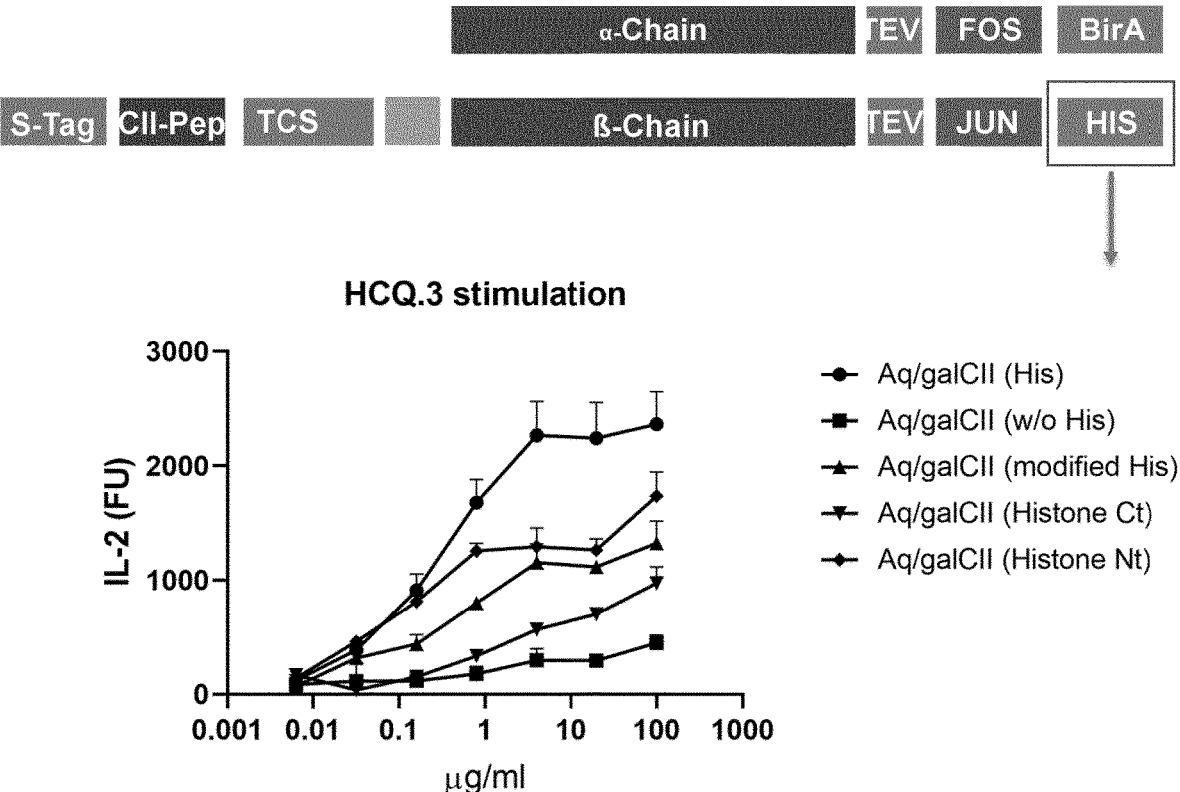
FIG. 16: Hybridoma assay for testing the Aq/gal264CII constructs with the alternative positively charged amino acid tags at the C-terminus of the Aq beta chain. The constructs with the His-tag or alternative positively charged amino acid tags is shown at the top, with TCS representing the Thrombin cleavage site followed by a linker prior to the β-chain and S-Tag representing the streptavidin-tag, as in FIG. 1. The Aq/gal264 CII peptide complexes with the alternative positively changed amino acid tags (Aq/galCII (modified His), Aq/galCII (Histone CT), Aq/galCII (Histone NT), were coated at different concentrations to the plastic surface of the microtiter wells, HCQ.3 T cell hybridoma were added and IL-2 secretion was determined by ELISA as a measure of specific cell activation. The His-tagged Aq/galCII (His) served as positive control and Aq/galCII (w/o His), without any tag served as a negative control.

Accordingly, in our search for sequences in self proteins containing basic amino acid residues for potential interaction with negatively charged sulfated carbohydrate structures, e.g. in chondroitin sulfate, we identified in the sequence of the human histone 2 A1 both at the N-terminal end (SGRGKQGGKARAKAKTRSSR; SEQ ID NO: 34) as well as at the carboxy-terminus (HKAKGK; SEQ ID NO: 43) respective candidate regions conserved between mouse and human (FIG. 15). Activation of T cell hybridoma HCQ.3 recognizing specifically the AQ/gal264CII-peptide complex using the alternative C-terminal tags is shown in FIG. 16. We investigated the impact of different alternative sequences attached to the C-terminal end of the sequence comprising the β-chain in the Aq-complexes as depicted at the top of FIG. 16 as a replacement of the His-tag on T cell activating properties. In addition to the Histone NT-tag (SGRGKQGGKARAKAKTRSSR; SEQ ID NO: 34) and the Histone CT-tag (HKAKGK; SEQ ID NO: 43), a modified His-tag comprising 6 alternating NH motives (NHNHNHNHNHNH, SEQ ID NO: 35) was tested. For this purpose hybridoma stimulation assays were performed under standard conditions:

the Aq/gal264 CII peptide complexes were coated to the plastic surface of the microtiter wells and IL-2 secretion was determined by ELISA as a measure of specific cell activation. The His-tagged Aq/gal264CII (His) served as positive control. As shown in FIG. 16 the Histone NT-tagged variant exhibited a T cell stimulating activity that was comparable to positive control in the concentration range between 0.01-1 μg/mL. The Histone CT-tag variant as well as the modified His-tag were less effective in activating HCQ.3 cells, but still showed a minor effect compared to the construct lacking the His-tag and without any replacement. Thus, preliminary in vitro testing of both histone 2A1 sequences in fusion constructs in Aq/galCII complexes in comparison with the respective HIS-tagged complexes revealed that the N-terminal sequence (NT): SGRGKQGGKARAKAKTRSSR (SEQ ID NO: 34) is functional to a comparable extend as the His-tag, while the C-terminal sequence (CT) of histone 2A1 only showed a minor effect and the modified histone tag an intermediate effect. We speculate that the number of positively charged amino acids is important (at least 6 positively charged amino acids) and consecutive positively charged amino acids are more beneficial. In case of alternating positively charged amino acids more basic amino acids, such as lysine (pK of 10.5) and arginine (pK of 12.5), seem to be preferred over histidine (pK of 6.0).

Figure 17:
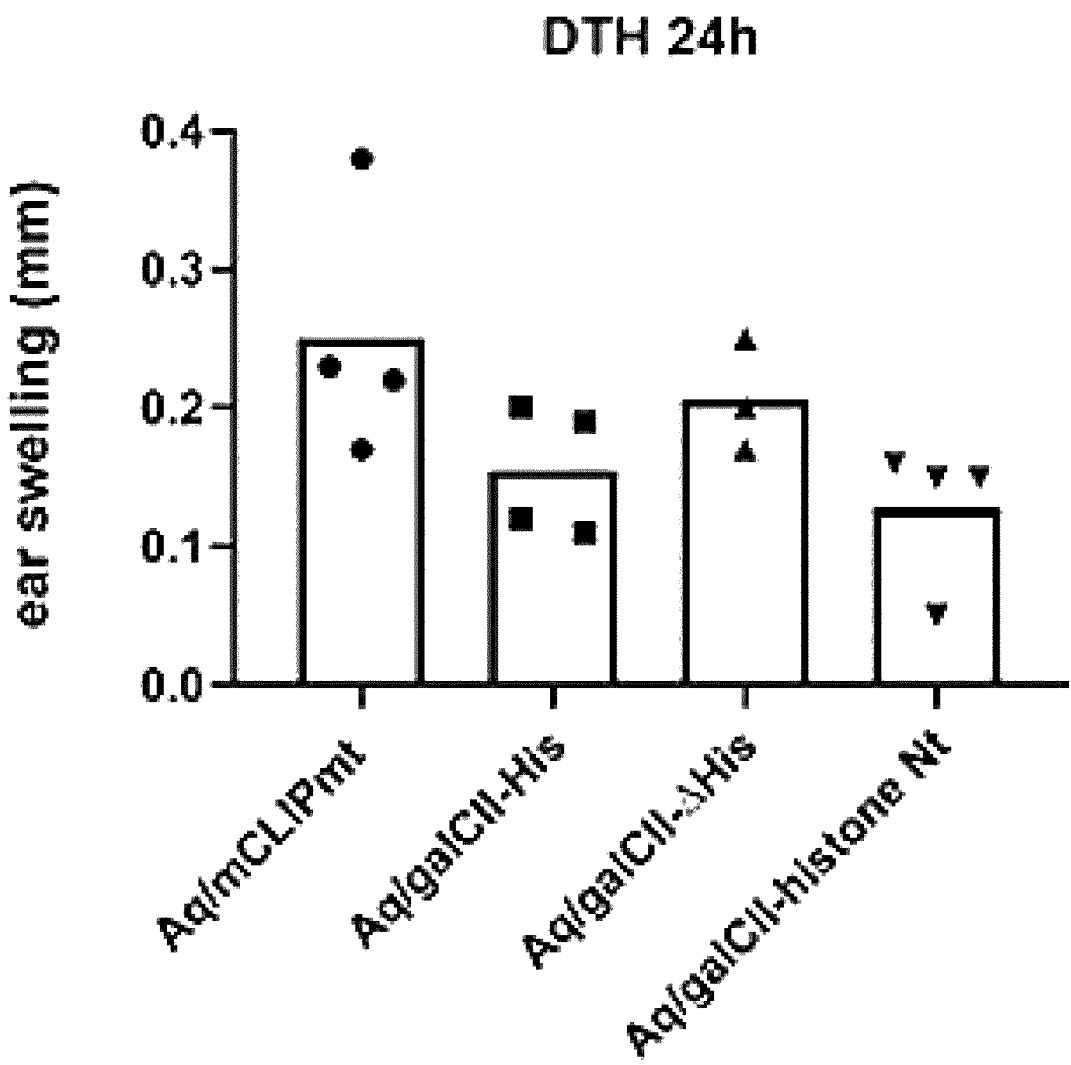
FIG. 17: Comparison of the therapeutic effect of Aq/galCII peptide complex with or without a His-tag and Aq/galCII peptide complex with histone NT-tag on ear swelling induced by the DTH reaction to collagen II in vivo. The effect of the Aq/galCII construct with (His) and without the polyhistidine tag (ΔHis) and with histone NT-tag are shown in comparison to an Aq/mCLIPmt control construct containing a linked mouse CLIP peptide in its binding groove (CLIPmt).

Consistently, preliminary in vivo testing in the model of the T cell-dependent CII-induced hypersensitivity reaction in Aq expressing QB mice demonstrated functional equipotent immunomodulatory pharmacological effects of MHCII/CII complexes in which the His-tag was replaced by the H2A1-derived NT-sequence. CII-preimmunized mice were triggered at day 8 post immunization by an intradermal CII injection into one ear to develop a T cell dependent inflammatory swelling controlled by a vehicle trigger applied to the contralateral ear. Prior to the induction of the DTH reaction the mice received treatment on day 4 postimmunization by a 24 h sc. pump-infusion of either a His-tag containing Aq/gal264 CII complex (Aq/galCII-His), an Aq/gal264 CII complex lacking the His-tag (Aq/galCII-ΔHis) or Aq/gal264 CII complexes containing the H2A1-derived sequences (Aq/galCII-histone NT). The His tagged Aq-complex containing a linked control peptide [class II associated invariant chain: CLIP] in its binding groove was included in the study as a negative control. The results as shown in FIG. 17 demonstrate functional equivalence of the NT-sequence with the His-tag in the therapeutic Aq/gal264 CII complexes.

Sequence listing:

SEQ ID NO: 1
AGFKGEQGPKG

SEQ ID NO: 2
AGFKGEQGPXG

SEQ ID NO: 3
AGFKGEX$_2$GPKG

SEQ ID NO: 4
AGFKGX$_3$QGPKG

SEQ ID NO: 5
AGFKX$_4$EQGPKG

SEQ ID NO: 6
AGFKGEX$_2$GPX$_1$G

SEQ ID NO: 7
AGFKGX$_3$QGPX$_1$G

SEQ ID NO: 8
AGFKX$_4$EQGPX$_1$G

SEQ ID NO: 9
AGFKGEQGPRG

SEQ ID NO: 10
AGFKGEQGPKGEP

SEQ ID NO: 11
AGFKGEQGPX$_1$GEP

SEQ ID NO: 12
AGFKGEQGPRGEP

SEQ ID NO: 13
GIAGFKGEQGPKGEP

SEQ ID NO: 14
GIAGFKGEQGPX$_1$GEP

SEQ ID NO: 15
GIAGFKGEQGPRGEP

SEQ ID NO: 16
DR4 construct α-chain

SEQ ID NO: 17
DR4 construct β-chain with hCII259-273 peptide

SEQ ID NO: 18
Minimal DR4 construct α-chain

SEQ ID NO: 19
Minimal DR4 construct β-chain with hCII259-273 peptide

SEQ ID NO: 20
DR4 construct β-chain with hCLIPmut

SEQ ID NO: 21
Aq construct α-chain

SEQ ID NO: 22
Aq construct β-chain with rat CII259-273 peptide

SEQ ID NO: 23
Aq construct β-chain with rat CII259-273 peptide without His-tag

SEQ ID NO: 24
Aq construct β-chain with mCLIP peptide

-continued

SEQ ID NO: 25
Aq construct β-chain with mCLIP peptide without His-tag

SEQ ID NO: 26
cFos domain

SEQ ID NO: 27
cJune domain

SEQ ID NO: 28
modified human CLIP-peptide

SEQ ID NO: 29
rat CII-peptide 259-273

SEQ ID NO: 30
streptavidin-tag

SEQ ID NO: 31
EKRIWFPYRRF

SEQ ID NO: 32
YKTNFRRYYRF

SEQ ID NO: 33
VLIRHFRKRYY

SEQ ID NO: 34
SGRGKQGGKARAKAKTRSSR

SEQ ID NO: 35
NHNHNHNHNHNH

SEQ ID NO: 36
KDHLIHNVHKEEHAHAHNK

SEQ ID NO: 37
H2A1_HUMAN

SEQ ID NO: 38
H2A1P_MOUSE

SEQ ID NO: 39
SAWSHPQFEKGIAGFKGEQGPKGEPSGGGS

SEQ ID NO: 40
H$_2$AC tag

SEQ ID NO: 41
6xHis

SEQ ID NO: 42
7xHis

SEQ ID NO: 43
HKAKGK

The invention claimed is:

1. A method of treating a chronic inflammatory disease in a human patient comprising administering to the patient a composition comprising recombinant HLA-DR/CII peptide complexes comprising (a) an extracellular region of an HLA-DR alpha chain comprising at least an alpha 1 domain;

(b) an extracellular region of an HLA-DR beta chain comprising at least a beta 1 domain;

(c) a collagen II peptide (CII peptide), optionally fused to the N-terminus of the HLA-DR alpha chain or the HLA-DR beta chain by a linker peptide; and (d) a chondroitin-binding peptide at the C-terminal end of the polypeptide comprising the HLA-DR alpha chain and/or the HLA-DR beta chain, wherein the CII peptide comprises the amino acid sequence selected from the group consisting of AGFKGEQGPKG (SEQ ID NO: 1), AGFKGEQGPXG (SEQ ID NO: 2), AGFKGEXGPKG (SEQ ID NO: 3), AGFKGXQGPKG (SEQ ID NO: 4), AGFKXEQGPKG (SEQ ID NO: 5), AGFKGEXGPXG (SEQ ID NO: 6), AGFKGXQGPXG (SEQ ID NO: 7), and AGFKXEQGPXG (SEQ ID NO: 8), and wherein at least the alpha 1 domain is from DRA*0101, and at least the beta 1 domain is from an HLA-DR allele selected from the group consisting of DRB1*0401, DRB1*0404, DRB1*0405, DRB1*0408, DRB1*0409, DRB1*0101, DRB1*0102, DRB1*1001, DRB1*1402, and DRB1*1303.

2. The method according to claim 1, wherein (a) the chondroitin-binding peptide is in its free form;

(b) the recombinant HLA-DR/CII peptide complexes are not multimerized via the chondroitin-binding peptide in the composition; and/or (c) the recombinant HLA-DR/CII peptide complexes are not bound to a further molecule via the chondroitin-binding peptide in the composition.

3. The method according to claim 1, wherein (a) the extracellular region of the HLA-DR alpha chain comprises an alpha 1 domain and an alpha 2 domain; and/or (b) the extracellular region of the HLA-DR beta chain comprises a beta 1 domain and a beta 2 domain.

4. The method according to claim 1, wherein at least the alpha 1 domain is from DRA*0101 and at least the beta 1 domain is from DRB1*0401.

5. The method according to claim 1, wherein the CII peptide is fused to the N-terminus of the HLA-DR alpha chain or the HLA-DR beta chain by a linker peptide.

6. The method of claim 5, wherein the CII peptide is fused to the N-terminus of the HLA-DR beta chain by a linker peptide.

7. The method according to claim 1, wherein the CII peptide comprises the amino acid sequence of AGFKGEQGPKG (SEQ ID NO: 1).

8. The method according to claim 1, wherein the chondroitin-binding peptide comprises 5 to 20 amino acids.

9. The method according to claim 1, wherein the chondroitin-binding peptide is a polyhistidine tag.

10. The method of claim 9, wherein the chondroitin-binding peptide is a hexahistidine tag.

11. The method according to claim 1, wherein the extracellular region of the HLA-DR alpha chain comprising at least an alpha 1 domain and the extracellular region of the HLA-DR beta chain comprising at least a beta 1 domain are expressed as a single fusion polypeptide.

12. The method according to claim 1, wherein the recombinant HLA-DR/CII peptide complexes comprise (a) a first polypeptide comprising the extracellular region of the HLA-DR alpha chain comprising at least an alpha 1 domain; and (b) a second polypeptide comprising the extracellular region of the HLA-DR beta chain comprising at least a beta 1 domain, wherein the HLA-DR alpha chain is fused at its C-terminal end to a first functional domain of a leucine zipper heterodimerisation motif, and the HLA-DR beta chain is fused at its C-terminal end to a second complementary functional domain of a leucine zipper heterodimerisation motif.

13. The method according to claim 12, wherein the first functional domain and the second complementary functional domain are (a) an acidic and a basic leucine zipper heterodimerisation domain; and/or (b) a jun-fos leucine zipper motif.

14. The method according to claim 1, wherein the recombinant HLA-DR/CII peptide complexes comprise a mixture of CII peptides with unmodified and/or one or more post-translationally modified lysine residue(s); wherein (a) the mixture of CII peptides consists of CII peptides with unmodified lysine residues;

(b) the mixture of CII peptides consists of CII peptides with the first lysine being hydroxylysine (Hyl);

(c) the mixture of CII peptides consists of CII peptides with the first lysine being galactosyl-hydroxylysine;

(d) the mixture of CII peptides consists of CII peptides with unmodified lysine residues and CII peptides with the first lysine being galactosyl-hydroxylysine;

(e) the mixture of CII peptides comprises CII peptides with the first lysine being galactosyl-hydroxylysine;

(f) the mixture of CII peptides comprises CII peptides with unmodified lysine residues and CII peptides with the first lysine being galactosyl-hydroxylysine;

(g) the mixture of CII peptides comprises CII peptides with unmodified lysine residues and CII peptides with the first lysine being galactosyl-hydroxylysine and/or hydroxylysine (Hyl); or (h) the mixture of CII peptides comprises CII peptides with unmodified lysine residues and CII peptides with the first lysine being O-glycosylated hydroxylysine and/or hydroxylysine (Hyl); and wherein the optional second lysine, if present, in the post-translationally modified CII peptide is unmodified, hydroxylysine, galactose-hydroxylysine and/or glucosyl-galactosyl-hydroxylysine.

15. The method of claim 14, wherein the optional second lysine, if present, in the post-translationally modified CII peptide is (a) unmodified, hydroxylysine and/or galactose hydroxylysine, or (b) unmodified.

16. The method according to claim 14, wherein the composition does not contain HLA-DR/CII peptide complexes comprising a mixture of CII peptides with a glucosyl-galactosyl-hydroxylysine modification.

17. The method according to claim 1, wherein the chronic inflammatory disease is selected from the group consisting of rheumatoid arthritis, osteoarthritis, psoriatic arthritis, non-radiographic axial spondyloarthritis, ankylosing spondylitis, juvenile idiopathic arthritis, relapsing polychondritis, systemic lupus erythematosus, Lyme disease, Meniere diseases, autoimmune inner ear disease (AIED), and Still's disease.

* * * * *